United States Patent
Jarrell

(10) Patent No.: US 12,110,524 B2
(45) Date of Patent: Oct. 8, 2024

(54) GENERATION OF ACYL ALCOHOLS

(71) Applicant: Modular Genetics, Inc., Woburn, MA (US)

(72) Inventor: Kevin A. Jarrell, Lincoln, MA (US)

(73) Assignee: Modular Genetics, Inc., Lincoln, MA (US)

(*) Notice: Subject to any disclaimer, the term of this patent is extended or adjusted under 35 U.S.C. 154(b) by 6 days.

(21) Appl. No.: 17/750,276

(22) Filed: May 20, 2022

(65) Prior Publication Data

US 2023/0039639 A1 Feb. 9, 2023

Related U.S. Application Data

(62) Division of application No. 15/744,574, filed as application No. PCT/US2016/042157 on Jul. 13, 2016, now Pat. No. 11,371,066.

(60) Provisional application No. 62/191,571, filed on Jul. 13, 2015.

(51) Int. Cl.
| | | |
|---|---|---|
| C12N 9/90 | (2006.01) | |
| C12P 7/6418 | (2022.01) | |
| C12P 13/00 | (2006.01) | |
| C12P 13/04 | (2006.01) | |

(52) U.S. Cl.
CPC ............ *C12P 13/001* (2013.01); *C12N 9/90* (2013.01); *C12P 7/6418* (2013.01); *C12P 13/04* (2013.01); *C12Y 501/01011* (2013.01)

(58) Field of Classification Search
CPC ....... C12P 7/6418; C12P 13/001; C12P 13/04; C12Y 501/01011; C12Y 301/010001; C12N 9/90; C12N 9/80
USPC ...................................................... 435/252.2
See application file for complete search history.

(56) References Cited

U.S. PATENT DOCUMENTS

| | | | |
|---|---|---|---|
| 5,652,116 | A | 7/1997 | Grandi et al. |
| 5,795,738 | A | 8/1998 | Grandi et al. |
| 6,060,051 | A | 5/2000 | Heins et al. |
| 6,103,228 | A | 8/2000 | Heins et al. |
| 6,291,426 | B1 | 9/2001 | Heins et al. |
| 6,417,163 | B1 | 7/2002 | Heins et al. |
| 6,638,910 | B2 | 10/2003 | Heins et al. |
| 7,981,685 | B2 | 7/2011 | Jarrell et al. |
| 8,101,785 | B2 | 1/2012 | Krull et al. |
| 8,318,950 | B2 | 11/2012 | Nebolsin et al. |
| 9,493,800 | B2 | 11/2016 | Jarrell et al. |
| 9,970,036 | B2 | 5/2018 | Jarrell et al. |
| 10,093,935 | B2 | 10/2018 | Jarrell et al. |
| 10,640,799 | B2 | 5/2020 | Jarrell et al. |
| 10,738,125 | B2 | 8/2020 | Goubier et al. |
| 10,745,485 | B2 | 8/2020 | Goubier et al. |
| 10,752,691 | B2 | 8/2020 | Goubier et al. |
| 11,371,066 | B2 | 6/2022 | Jarrell |
| 2004/0170626 | A1 | 9/2004 | Schuurman et al. |
| 2004/0180400 | A1 | 9/2004 | Rosazza et al. |
| 2005/0027113 | A1 | 2/2005 | Miao et al. |
| 2007/0053589 | A1 | 3/2007 | Gering |
| 2008/0025947 | A1 | 1/2008 | Gillies et al. |
| 2008/0154118 | A1 | 6/2008 | Dale et al. |
| 2010/0297751 | A1 | 11/2010 | Marahiel et al. |
| 2011/0030102 | A1 | 2/2011 | Jarrell et al. |
| 2011/0030103 | A1 | 2/2011 | Reznik et al. |
| 2012/0128603 | A1 | 5/2012 | Tanaka |
| 2013/0071885 | A1 | 3/2013 | Jarrell et al. |
| 2014/0099254 | A1 | 4/2014 | Chang et al. |
| 2016/0076065 | A1 | 3/2016 | Jarrell et al. |
| 2016/0135925 | A1 | 5/2016 | Mason et al. |
| 2017/0016006 | A1 | 1/2017 | Jarrell et al. |
| 2018/0201962 | A1 | 7/2018 | Jarrell |
| 2018/0340198 | A1 | 11/2018 | Jarrell et al. |
| 2019/0062759 | A1 | 2/2019 | Jarrell et al. |
| 2019/0135925 | A1 | 5/2019 | Quezada et al. |
| 2019/0284287 | A1 | 9/2019 | Goubier et al. |
| 2019/0300613 | A1 | 10/2019 | Goubier et al. |
| 2019/0322752 | A1 | 10/2019 | Goubier et al. |
| 2020/0010554 | A1 | 1/2020 | Goubier et al. |
| 2020/0283535 | A1 | 9/2020 | Merchiers et al. |

FOREIGN PATENT DOCUMENTS

| | | | |
|---|---|---|---|
| JP | 2005-508622 | A | 4/2005 |
| WO | WO-02/059322 | A2 | 8/2002 |
| WO | WO-03/014297 | A2 | 2/2003 |
| WO | WO-2004/045512 | A2 | 6/2004 |
| WO | WO-2004/074437 | A2 | 9/2004 |
| WO | WO-2005/115451 | A2 | 12/2005 |
| WO | WO-2005/123780 | A2 | 12/2005 |
| WO | WO-2006/050172 | A2 | 5/2006 |
| WO | WO-2006/108670 | A2 | 10/2006 |
| WO | WO-2008/131002 | A2 | 10/2008 |
| WO | WO-2008/131014 | A1 | 10/2008 |
| WO | WO-2012/068195 | A1 | 5/2012 |

(Continued)

OTHER PUBLICATIONS

Aguilar et al., A Bacillus subtilis gene induced by cold shock encodes a membrane phospholipid desaturase., Journal of Bacteriology., 180(8): 2194-2200 (1998).

(Continued)

*Primary Examiner* — Tekchand Saidha
*Assistant Examiner* — Mohammad Y Meah
(74) *Attorney, Agent, or Firm* — Choate, Hall & Stewart LLP; Brenda Herschbach Jarrell; Rolando Medina

(57) ABSTRACT

Methods, compositions, and cells for generating acyl alcohols. Compositions comprising acyl alcohols. Methods of cleaving acyl amino acids and/or acyl alcohols to generate free fatty acids, free amino acids, and/or free alcohols.

15 Claims, 25 Drawing Sheets

Specification includes a Sequence Listing.

(56) References Cited

FOREIGN PATENT DOCUMENTS

| WO | WO-2014/144649 A1 | 9/2014 |
| WO | WO-2014/145907 A1 | 9/2014 |
| WO | WO-2016/011264 A1 | 1/2016 |
| WO | WO-2016/021720 A1 | 2/2016 |

OTHER PUBLICATIONS

Andersson, M.A. et al., Acrebol, a novel toxic peptaibol produced by an Acremonium exuviarum indoor isolate, J. Appl. Microbiol., 106: 909-923 ( 2009).

Aron et al., FenF: Servicing the Mycosubtilin Synthetase Assembly Line in trans, ChemBioChem, 8: 613-616 (2007).

Assie et al., Insecticide activity of surfactins and iturins from a biopesticide *Bacillus subtilis* Cohn (S499 strain), Meded Rijksuvin Gent Fak Landbouwkd Toegep Biol Wet., 67(3):647-655 (2002) Abstract only.

ATCC8185, printed 2011 [http://www.atcc.orq/ATC-CAdvancedCataloqSearch/ProductDetails/tabid/452/Default.aspx?ATCCNum=8185&Template=bacteria].

Badadani, M. et al., Optimum conditions of autoclaving for hydrolysis of proteins and urinary peptides of prolyl and hydroxyprolyl residues and HPLC analysis, J. Chromatogr. B. Analyt. Technol. Biomed. Life Sci., 847(2): 267-74 (2007).

Balaban, A. T. et al., Structure-property analysis of octane numbers for hydrocarbons (alkanes, cycloalkanes, alkenes), MATCH Commun. Math Comput. Chem., 28:13-27 (1992).

Beasley et al., Mutation of L-2, 3-diaminopropionic acid synthase genes blocks staphyloferrin B synthesis in *Staphyloccus aureus.*, BMC Microbilogy., 11:199 (2011).

Bruner et al., Structural Basis for the Cyclization of the Lipopeptide Antibiotic Surfactin by the Thioesterase Domain SrfTE, Structure, 10:301-310 (2002).

Challis, G. L. et al., Predictive, structure-based model of amino acid recognition by nonribosomal peptide synthetase adenylation domains, Chemistry & Biology, 7(3): 211-224 (2000).

Chhabra, A. et al., Nonprocessive [2+2]e offloading reductase domains from mycobacterial nonribosomal peptide synthetases, *PNAS*, 109(15):5681-5686 (2012).

Choi et al., β-ketoacyl-acyl carrier protein synthase III (FabH) is a determining factor in branched-cahin fatty acid biosynthesis., Journal of Bacteriology., 182(2): 365-370 (2000).

Coque, J.J. et al., The cephamycin biosynthetic genes pcbAB, encoding a large multidomain peptide synthetase, and pcbC of Nocardia lactamdurans are clustered together in an organization different from the same genes in Acremonium chrysogenum and Penicillium chrysogenum, Mol. Microbiol., 5(5): 1125-33 (1991).

Cosmina, P. et al., Sequence and analysis of the genetic locus responsible for surfactin synthesis in Bacillus subtilis, Mol. Microbiol., 8(5): 821-31 (1993).

Dantal, J. et al., Cluster-Function Relationship of Rat-Antimouse P55 IL-2 Receptor Monoclonal Antibodies, Transplantation, 52: 110-115 (1991).

De Ferra et al., Engineering of Peptide Synthetases, Journal of Biological Chemistry 272(40):25304-25309 (1997).

Degenkolb et al., The *Trichoderma brevicompactum* clade: a separate lineage with new species, new peptaibiotics, and mycotoxins, Mycol Progress, 7(3):177-219 (2008).

Devos, D. and Valencia, A., Practical Limits of Function Prediction, Proteins: Structure, Function, and Genetics, 41: 98-107 (2000).

Diez, B. et al, The cluster of penicillin biosynthetic genes. Identification and characterization of the pcbAB gene encoding the alpha-aminoadipyl-cysteinyl-valine synthetase and linkage to the pcbC and penDE genes, J. Biol Chem., 265(27): 16358-65 (1990).

Du, L. and Lou, L., PKS and NRPS release mechanisms, Nat. Prod. Rep., 27: 255-278 (2010).

Duitman et al., The Mycosubtilin synthetase of Bacillus subtilis ATCC6633: A multifunctional hybrid between a peptide synthetase, an amino transferase, and a fatty acid synthase. PNAS, 96(23): 13294-13299 (1999).

Felnagle et al., Identification of the biosynthetic gene cluster and an additional gene for resistance to the antituberculosis drug capreomycin., Applied and Environmental Microbiology., 73(13): 4162-4170 (2007).

Ferrini, S. et al., Regulatory T cell depletion/blockade in combination with IL-21-based immunotherapy: a pre-clical[ sic] study, Cancer Immunol Immunother., 57 (Suppl 1): S1-S53, p. 16 P050 (2008).

Fields et al., A Novel Genetic System To Detect Protein-Protein Interactions, Nature, 340:245-246 (1989).

Furness, A.J.S. et al., Impact of tumour microenvironment and Fc receptor on the activity of immunomodulatory antibodies, Trends in Immunology, 35(7): 290-298 (2014).

GenBank Accession No. AAX31555.1, acyl-CoA ligase [Streptomyces roseosporus NRRL 11379], 2 pages (Jul. 26, 2016). [Retrieved Apr. 21, 2017].

GenBank Accession No. AAX31556.1, probable acyl carrier protein [Streptomyces roseosporus NRRL 11379], 1 page (Jul. 26, 2016). [Retrieved Apr. 21, 2017].

Goudin, N. et al., Depletion of Regulatory T Cells Induces High Numbers of Dendritic Cells and Unmasks a Subset of Anti-tumour CD8+CD11c+ PD-1lo Effector T Cells, PLOS ONE, 11(6): 1-11 (2016).

Grauer et al., CD41FoxP31 regulatory T cells gradually accumulate in gliomas during tumor growth and efficiently suppress antiglioma immune responses in vivo, Int. J. Cancer, 121:95-105 (2007).

Hansen et al., The Loading Module of Mycosubtilin: An adenylation Domain with fatty Acid Selectivity., J Am Chem Soc., 129(20): 6366-6367 (2007).

Hojati, Z. et al., Structure, biosynthetic origin, and engineered Biosynthesis of calcium-Dependent Antibiotics from Streptomyces coelicolor., Chemistry & Biology, 9: 1175-1187 (2002).

Ibsen, K. et al., Review of market for octane enhancers, Final Report for NREL prepared under subcontract No. TXE-0-29113-01, 1-54 (2000).

International Preliminary Report on Patentability from PCT/US08/060474, dated Oct. 20, 2009.

International Search Report for PCT/US2014/029150, 5 pages (Aug. 7, 2014).

International Search Report for PCT/US2016/042157, 5 pages (Dec. 28, 2016).

International Search Report from PCT/US08/60474, dated Oct. 21, 2008.

Kaneda and Smith., Relationship of primer specificity of fatty acid de novo synthetase to fatty acid composition in 10 species of bacteria and yeasts., Can. J. Microbiol, 26(8): 893-898 (1980).

Kaneda, Iso- and anteiso-fatty acids in bacteria: biosynthesis, function, and taxonomic significance., Microbiological Reviews., 55(2): 288-302 (1991).

Kaneda., Fatty Acids of the Genus *Bacillus*: an example of branched-chain preference, Bacteriological Review., 41(2): 391-418 (1977).

Kessler, N. et al., The linear pentadecapeptide gramicidin is assembled by four multimodular nonribosomal peptide synthetases that comprise 16 modules with 56 catalytic domains, J. Biol. Chem. 279(9):7413-7429 (2004).

Khandekar et al., Identification, substrate specificity, and inhibition of the *Streptococcus pneumonia* β-ketoacyl-acyl carrier protein synthase III (FabH)., Journal of Biological Chemistry 276(32): 30024-30030 (2001).

Kisselev, L., Polypeptide release factors in prokaryotes and eukaryotes: same function, different structure, Structure, 10: 8-9 (2002).

Kleinkauf et al., A nonribosomal system of peptide biosynthesis., Eur J. Biochem., 236: 335-351 (1996).

Kleinkauf, H. and Döhren, H. V., Biosynthesis of Peptide Antibiotics, Ann. Rev. Microbio., 41: 259-89 (1987).

Komiyama et al., A new antibiotic, cypemycin taxonomy, fermentation, isolation and biological characteristics., The Journal of Antibiotics., 46(11): 1666-1671 (1993).

(56) References Cited

OTHER PUBLICATIONS

Kraas, F. I. et al., Functional Dissection of Surfactin Synthetase Initiation Module Reveals Insights into the Mechanism of Lipoinitiation, Chemistry and Biology, 17: 872-880 (2010). Supplemental Information appended, 7 pages.
Krätzschmar, J. et al, Gramicidin S biosynthesis operon containing the structural genes grsA and grsB has an open reading frame encoding a protein homologous to fatty acid thioesterases, J. Bacteriol., 171(10): 5422-9 (1989).
Lait et al., Rapid biosynthesis of N-linolenoyl-L-glutamine, an elicitor of plant volatiles, by membrane-associated enzyme(s) in Manduca sexta, PNAS USA, 100(12):7027-7032 (2003).
Lee et al., Clothing of srfA operon from Bacillus subtillis C9 and its expression E.coli., Appl Microbiol Biotechnol., 75(3): 567-572 (2007).
Lee, S. J. et al., Isolation and sequence analysis of new peptaibol, boletusin, from Boletus spp., J Pept Sci 5(8):374-378 (1999).
Li et al., Alteration of the fatty acid profile of Streptomyces coelicolor by replacement of the initiation enzyme 3-ketoacyl acyl carrier protein synthase III (FabH). Journal of Bacteriology, 187(11): 3795-3799 (2005).
Li et al., Identification and functional expression of a 9-fatty acid desaturase from Psychorobacter urativorans in Escherichia coli., Lipids., 43(3): 207-213 (2008).
Liang, F. et al., The organic composition of diesel particulate matter, diesel fuel and engine oil of a non-road diesel generator, J. Environ. Monit., 7:983-988 (2005).
Maccabe, A.P. et al., Delta-(L-alpha-aminoadipyl)-L-cysteinyl-D-valine synthetase from Aspergillus nidulans. Molecular characterization of the acvA gene encoding the first enzyme of the penicillin biosynthetic pathway, J. Biol. Chem., 266(19): 12646-54 (1991).
Manavalan, B. et al, Molecular modeling of the reductase domain to elucidate the reaction mechanism of reduction of peptidyl thioester into its corresponding alcohol in non-ribosomal peptide synthetases, BMC Struct. Biol, 10(1): 1-14 (2010).
Marinangeli, R. et al., Opportunities for biorenewables in oil refineries, Submitted to U.S. Department of Energy, 1-43 (2005).
Martin et al., A lipA (yutB) mutant, encoding lipoic acid synthase, provides insight into the interplay between branched-chain and unsaturated fatty acid biosynthesis in Bacillus subtilis., Journal of Bacteriology., 191(24): 7447-7455 (2009).
Miao et al., Daptomycin biosynthesis in Streptomyces roseosporus: cloning and analysis of the gene cluster and revision of peptide stereochemisty., Microbiology., 151: 1507-1523 (2005).
Mitz, M.A. and Schlueter, R.J., Direct spectrophotometric measurement of the peptide bond; application to the determination of acylase I, Biochimica Biophysica Acta, 27(1):168-172 (1958).
Morris, J. et al., Receptor-Directed Therapy of T-Cell Leukemias and Lymphomas, Journal of Immunotoxicology, 5:235-248 (2008).
Nagai et al., Study On Surfactin, A Cyclic Depsipeptide. II. Synthesis of Surfactin B2 Produced by Bacillus Natto KMD 2311, Chemical and Pharmaceutical Bulletin (Tokyo) 44(1):5-10 (1996).
Nimmerjahn, F. et al., Fc[gammag]R dependent mechanisms of cytotoxic, agonistic, and neutralizing antibody activities, Trends in Immunology, 36(6): 325-336 (2015).
Ortega, G. et al., The murine IL 2 receptor. I. Monoclonal antibodies that define distinct functional epitopes on activated T cells and react with activated B cells, Journal of Immunology, 133: 1970-1975 (1984).
Ötvös, L. et al, Investigation on the mechanism of acylase-l-catalyzed acylamino acid hydrolysis, Biochem. Bipophys. Res. Commun., 44(5):1056-1064 (1971).
Perdih, A. and Perdih, F., Chemical Interpretation of Octane Number., Acta. Chim. Slov., 53: 306-315 (2006).
Phillips, K. et al., IL-2Rα-Directed Monoclonal Antibodies Provide Effective Therapy in a Murine Model of Adult T-Cell Leukemia by a Mechanism Other than Blockade of IL-2/IL-2Rα Interaction, Cancer Research, 60(24):6977-84 (2000).
Quadri et al., Characterization of Sfp, A Bacillus subtilis phosphopantetheinyl transferase for peptididyl carrier domains in peptide synthetases, Biochemistry., 37(6): 1585-1595 (1998).
Rausch, C. et al., Phylogenetic analysis of condensation domains in NRPS sheds light on their functional evolution, BMC Evolutionary Biology, 7(78): 1-15 (2007).
Rausch, C. et al., Specificity prediction of adenylation domains in nonribosomal peptide synthetases (NRPS) using transductive support vector machines (TSVMs), Nucleic Acids Research, 33(18): 5799-5808 (2005).
Reznik et al., Use of sustainable chemistry to produce an acyl amino acid surfactant., Appl Microbiol. Biotechnol., Online (2010).
Richardt, A. et al., Ebony, a novel nonribosomal peptide synthetase for beta-alanine conjugation with biogenic amines in Drosophila, J. Biol. Chem., 278( 42):41160-6 (2003).
Roongsawang, N. et al, Diversity of Nonribosomal Peptide Synthetases Involved in the Biosynthesis of Lipopeptide Biosurfactants, International J. Mol. Sci., 12: 141-172 (2011).
Roongsawang, N. et al., Phylogenetic analysis of condensation domains in the nonribosomal peptide synthetases, FEMS Microbiology Letters, 252: 143-151 (2005).
Sakuradani et al., A9-fatty acid desaturase from arachidonic acid-producting fungus unique gene sequence and its heterologus expression in a fungus, Aspergillus., Biochem., 260: 208-219 (1999).
Schracke et al., Synthesis of linear gramicidin requires the cooperation of two independent reductases, Biochemistry, 44:8507-8513 (2005).
Segolene et al., NORINE: a database of nonribosomal peptides, Nucleic Acid Research., 36: D327-D331 (2008).
Simon and Shokat., A method to site-specifically incorporate methyl-lysine analogues into recombinant proteins., Methods in Enzymology., 512: Nucleosomes: Histones & Chromatin, Part A (2012).
Smith, D. J. et al., Beta-lactam antibiotic biosynthetic genes have been conserved in clusters in prokaryotes and eukaryotes, EMBO J., 9(3): 741-7 (1990).
Smith, D. J. et al, The multifunctional peptide synthetase performing the first step of penicillin biosynthesis in Penicillium chrysogenum is a 421,073 dalton protein similar to Bacillus brevis peptide antibiotic synthetases, EMBO J., 9(9): 2743-50 (1990).
Stachelhaus, T. et al., Biochemical characterization of peptidyl carrier protein (PCP) the thiolation domain of mulifunctional peptide synthetases, Chemistry & Biology, 3(11): 913-921 (1996).
Stellar et al., Initiation of Surfactin Biosynthesis and the Role of the SrfD-Thioesterase Protein., Biochemistry, 43: 11331-11343 (2004).
Symmank, H. et al., Analysis of engineered multifunctional peptide synthetases. Enzymatic characterization of surfactin synthetase domains in hybrid bimodular systems, Journal of Biological Chemistry, 274(31): 21581-21588 (1999).
Tatham, E. et al., Production of mycobacterial cell wall glycopeptidolipids requires a member of the MbtH-like protein family, BMC Microbiology, 12:118:1-14 (2012).
Tsay, J-T. et al., Isolation and characterization of the -ketoacyl-acyl carrier protein synthatse III gene (fabH) from Escherichia coli K-12., JBC., 267(10): 6807-6814 (1992).
Tseng, C.C. et al., Characterization of the surfactin synthetase C-terminal thioesterase domain as a cyclic depsipeptide synthase, Biochemistry, 41(45):13350-13359 (2002).
Van Wagoner, R.M. and Clardy, J., FeeM, an N-acyl amino acid synthase from an uncultured soil microbe: structure, mechanism, and acyl carrier protein binding, Structure, 14(9):1425-1435 (2006).
Wang et al., The primary structure of branched-chain a-oxo acid dehydrogenase from Bacillus subtilis and its similarity to other a-oxo acid dehydrogenases., Eur. J. Biochem., 213: 1091-1099 (1993).
Weckermann, R. et al., Complete nucleotide sequence of the tycA gene coding the tyrocidine synthetase 1 from Bacillus brevis, Nucleic Acids Res., 16(24): 11841 (1988).
Welch., Applications of cellular fatty acid analysis., Clinical Microbiology Reviews, 4(4):422-438 (1991).
Whisstock, J. C. and Lesk, A. M., Prediction of protein function from protein sequence and structure, Quaterly Reviews of Biophysics, 36(3): 307-340 (2003).

(56) References Cited

OTHER PUBLICATIONS

Wiest et al., Identification of peptaibols from *Trichoderma virens* and cloning of a peptaibol synthetase, *JBC*, 277(23): 20862-20868 (2002).
Willecke et al., Fatty acid-requiring mutant of bacillus subtilis defective in branched chain α-keto acid dehydrogenase., The Journal of Biological Chemistry., 246(17): 5264-5272 (1971).
Witkowski, A. et al., Conversion of a β-ketoacyl synthase to a malonyl decarboxylase by replacement of the active-site cysteine with glutamine, Biochemistry, 38: 11643-11650 (1999).
Wittmann et al., Role of DptE and DptF in the lipidation reaction of daptomycin., FEBS Journal., 275: 5343-5353 (2008).
Written Opinion for PCT/US2014/029150, 5 pages (Aug. 7, 2014).
Written Opinion for PCT/US2016/042157, 9 pages (Dec. 28, 2016).
Written Opinion of the ISA from PCT/US08/60474, dated Oct. 21, 2008.
Yuan et al., Fatty Acid Biosynthsis in Pseudomonas aeruginosa Is Initiated by the FabY Class of β-Ketoacyl Acyl Carrier Protein Synthases, Journal of Bacteriology, 194(19): 5174-5184 (2012).
Zhang et al., Catalytic promiscuity of a bacterial α-N-methyltransferase., FEBS Letters., 586(19): 3391-3397 (2012).

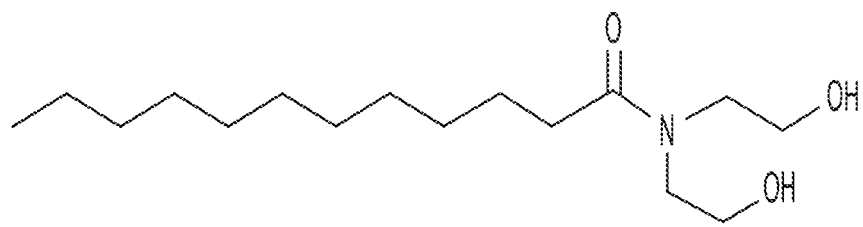
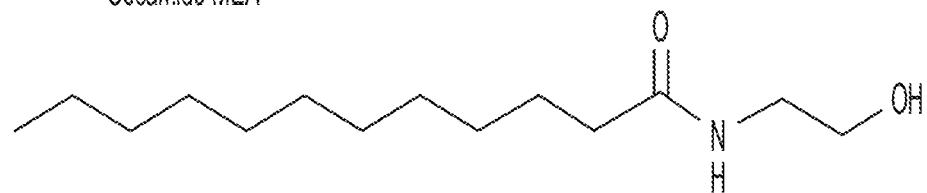
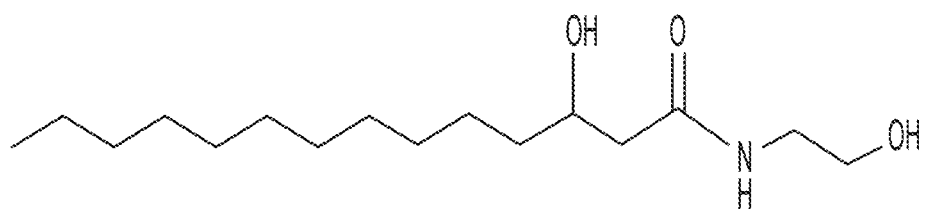
Fig. 1

Condensation, adenylation, and reductase domains of module 16
of the Bacillus brevis gramicidin synthetase complex (glycine module)

DVSVSEIWQALLSGGTLVIEDRESLLPGPDLVRTLRERRISKVSMASSLLASLPVAEYPD
LAVLEVGGDACSRELVARYATGRKFFNCYGPTEATVGTVIKQLTLDDDTPTIGRPFPNTK
LYVLDQNRKPVPVGVPGELYIGGECLARGYWNRPELTAERFVANPFGQPGERLYRTGDLV
RYLPDGNVDYLGRFDDQVKIRGYRIELGEIAEALRQHAAIREAVVLAREVRPGDKRLAAY
LTSAAEQELSVDEIKQWLKEKLPDYMVPASYTWLPAIPLNVNGKVDRKALPAPDWGQITA
AYVAPRNPLEEMIANVFAEVLAVEKVGIDDNFFELGGHSLLATQTVSRLREIVGVELQLR
TLFEHPTVAGLGEQLELLTKQSSRKLAPPIGKVSRKEPLPLSFTQQRLWFLEQFTQNSSI
NNIPSFLRIQGELDVAAWEASFSAIILRHESLRTSFEVRDGRPVQVIQPHGDWAMTRIDL
RALEPAEREAEIKRLAEQAIVQPFDLTKGLLLRASLVQLDANDFVFLFVMHHIASDGWSM
GILLSELMTNYKAFRQGEASPLGELPIQYADFAVWQREWLSGEVLAEQLGYWREKLKGSE
PLLQLPTDRPRPPVQTYEGEKMSVQFGAELLKQLQSLSRKEGATLFMTLFAAFQTLLYRY
TNQDDILVGTPIAGRNKQETEQLIGYFINTLVLRTDMSGHPSFRELLARVRETALEAYAH
QDVPFEKLLDELQLERSMSYSPLFQVMFILQNIPVQ AEPAGDIQLSSFDLELGAVTSKFD
MTVTMVETPDGLLATLEYNKALFDSSTITRMVEHFHKLMEEIVANPDQSITLLPLMREEE
EQLLITEWNRTEVPYSREKCVHEMIEEMVSKAPDSIALIVGEQRVTYGELNRQANQLAHY
LRKQGVGPEVLVGICAERTVEMMIGLLAILKAGGAYVPIDPAYPAERIAYIIGHSQIPVL
LTQEHLLPTLPEHQAKVICLDRDWATVAVESEENPGKLATSDNLIYVIYTSGSTGNPKGV
ALEHRSVIYFLSWAHDTYTPEEMSGVLFSTSICFDLSVYEMFATLTMGGKVIMAENALQL
PALPAADQVTLVNTVPSAATELVRMKGIPASVRVINLCGEPLSNRLAQELYAFPHVEKVF
NLYGPTEDTVYSTHAIVTKGATNEPLIGRPQFNTHVFVLDSHRKPVPVGVPGELYLSGSG
LARGYLHRPDLTAERFVQNPFREPGARMYRTGDLVRYLPDGNLQFVGRVDYQVKIRGYRI
ELGEIESVLNRFPGVKEVVLLAREDREGDKCLVAYIVFEADCTSKIHDLNHFLADKLPAY
MIPQHYMILDSLPKTPNGKLDRKALPKPEYDRSEAGVEYVAPQTPVEIMLHAHWAAVLEM
ETIGVHDNFFEIGGHSLLATQLIFKVREELQLEVPLRILFETPTIAGMAKTIEEIIKHGL
TSVSQEIDAKGLQDEVALDPAILAEQPYEGDP SQFQAALLTGATGFLGAFLLRDLLQMTD
ADIYCLVRASGEEEGLARLRKTLQLYELWDEAQAHRIIPVIGDLAQPRLGLSAGQFDALA
ATVDVIYHNGALVNFVYPYAALKKANVIGTEEIIR reLAAAKKTKPVHFV[S]TIFTFASEEGE
ESVAVREEDMPENSRILTSG[Y]TQS[K]WVAEHIVNLARQRGIPTAIYRCGRMTGDSETGACQ
KD[D]LMWRIAAGIIDLGKAPDMSGDLDMMPVDFASKGIVHLSMTEHSVNSNFHLLNPNATD
YDDLIAAIENKGFELERVTMDEWIEAVQEDAKDKGMDANSAAPLGNLFSDGHSSRGSVVY
VGNKTTRLLRQADIECPEIDEEVFAKVLDYFARTGQLRVTQNTRN (SEQ ID NO: 3)

Fig. 4

Adenylation domain of module 16 of the *Bacillus brevis* gramicidin synthetase complex (glycine module)

VHEMIEEMVSKAPDSIALIVGEQRVTYGELNRQANQLAHY
LRKQGVGPEVLVGICAERTVEMMIGLLAILKAGGAYVPIDPAYPAERIAYIIGHSQIPVL
LTQEHLLPTLPEHQAKVICLDRDWATVAVESEENPGKLATSDNLIYVIYTSGSTGNPKGV
ALEHRSVIYFLSWAHDTYTPEEMSGVLFSTSICFDLSVYEMFATLTMGGKVIMAENALQL
PALPAADQVTLVNTVPSAATELVRMKGIPASVRVINLCGEPLSNRLAQELYAFPHVEKVF
NLYGPTEDTVYSTHAIVTKGATNEPLIGRPQFNTHVFVLDSHRKPVPVGVPGELYLSGSG
LARGYLHRPDLTAERFVQNPFREPGARMYRTGDLVRYLPDGNLQFVGRVDYQVKIRGYRI
ELGEIESVLNRFPGVKEVVLLAREDREGDKCLVAYIVFEADCTSKIHDLNHFLADKLPAY
MIPQHYMILDSLPKTPNGKLDRKALPKPEYDRSEAGVEYVAPQT (SEQ ID NO: 4)

Fig. 5A

GTCCATGAAATGATCGAGGAAATGGTGAGCAAAGCACCGGACAGCATCGCCCTGATCGTGGGTG
AGCAGCGCGTAACGTACGGCGAGTTGAACAGGCAGGCGAACCAACTGGCGCATTATTTGCGCAA
GCAGGGAGTTGGCCCGGAAGTGCTCGTCGGCATATGCGCAGAGCGGACGGTCGAAATGATGATC
GGACTTTTGGCGATCCTCAAGGCTGGCGGCGCTTATGTGCCCATCGATCCGGCGTATCCGGCAG
AGCGGATTGCCTACATCATCGGGCATTCGCAAATTCCGGTTCTGCTTACGCAAGAACATCTGCT
GCCGACGCTGCCTGAGCACCAGGCGAAAGTGATTTGCCTGGATCGCGATTGGGCAACGGTAGCG
GTTGAGTCCGAGGAAAATCCAGGCAAGCTTGCGACCTCCGACAATTTGATCTACGTCATTTACA
CATCAGGCTCTACCGGCAATCCAAAAGGGGTGGCACTGGAACACCGCAGCGTTATTTACTTCCT
CTCTTGGGCGCATGACACTTATACGCCTGAGGAGATGAGCGGCGTCCTGTTCTCCACATCGATC
TGCTTCGACTTGTCTGTGTACGAGATGTTTGCCACCTTGACCATGGGCGGCAAAGTGATCATGG
CGGAAAATGCCTTGCAACTGCCAGCCTTGCCAGCAGCCGATCAGGTGACGCTCGTCAATACAGT
GCCATCGGCCGCGACAGAGCTTGTCCGCATGAAGGGCATACCGGCTTCGGTGCGTGTCATCAAC
TTGTGCGGCGAGCCGCTTTCCAACCGATTGGCACAAGAGCTGTACGCCTTCCCGCACGTGGAAA
AAGTGTTCAATCTGTACGGGCCGACGGAGGATACCGTTTACTCCACACACGCGATCGTGACAAA
AGGAGCGACGAACGAGCCGCTAATCGGCAGACCGCAGTTCAATACGCACGTCTTCGTGCTGGAC
AGCCACCGCAAGCCTGTGCCAGTAGGGGTGCCGGGGGAATTGTACCTCAGCGGTTCCGGCTTGG
CGCGCGGCTACTTGCACCGTCCCGATCTGACCGCAGAACGTTTTGTGCAAAATCCGTTCCGCGA
ACCGGGAGCGAGAATGTACCGGACTGGCGACCTCGTGCGCTACTTGCCGGACGGAAATCTCCAG
TTTGTCGGCCGCGTCGATTACCAGGTGAAAATCCGCGGCTACCGCATCGAGCTGGGCGAAATCG
AGTCCGTGCTGAACCGCTTCCCGGGCGTCAAGGAGGTCGTGCTGCTCGCCCGTGAAGATCGGGA
AGGCGACAAGTGCCTGGTTGCGTACATCGTGTTCGAGGCCGATTGCACAAGCAAGATTCACGAT
CTGAATCACTTTTTGGCCGACAAGCTGCCAGCGTACATGATTCCGCAGCATTACATGATTTTGG
ACAGCTTGCCCGAAGACGCCAAACGGCAAACTGGACCGCAAAGCGCTGCCGAAGCCGGAATACGA
CCGCTCGGAAGCAGGAGTCGAATACGTCGCGCCGCAAACG (SEQ ID NO: 5)

Fig. 5B

LgrE amino acid sequence

MQKTHVSPSRWLLSPKMTAEAEVLLFSFHYAGGHAGIYREWQKKLPVQIGVCPVQLPGRSNRFM
EPYYTDLSVMIRELAEALLPHLNRPFAFFGHSMGALVSFELARYLRNQYGIKPRHMFASGRHAP
HLPDPGEATHHLPDAEFLKGLRTLNGTPKELFENEENEEILQMLLPMLRADFTICEQYQYQEEE
PLGCGLTAIGGWQDPDITVAHMEAWRKHTSASFQMHMLQGDHFFLHSEQEQLLAIIESTLQSYL
VGYRGIG        (SEQ ID NO: 6)

Fig. 6A

LgrE nucleotide sequence

ATGCAAAAGACACACGTTTCCCCGAGCCGTTGGCTGCTTTCCCCGAAAATGACGGCGGAGGCAG
AGGTGCTTTTATTCAGCTTTCACTATGCAGGCGGACATGCTGGCATCTATCGCGAGTGGCAAAA
AAAGCTGCCTGTGCAGATCGGGGTGTGCCCCGTGCAGCTGCCAGGCAGGAGCAATCGGTTTATG
GAGCCGTACTACACCGACTTGTCCGTGATGATCCGCGAGCTGGCGGAAGCGCTTTTGCCCCATC
TGAATCGCCCGTTTGCCTTTTTTGGACATAGCATGGGAGCGCTGGTCAGCTTCGAGCTGGCCAG
ATATTTGCGCAACCAGTACGGTATCAAGCCGCGGCATATGTTCGCTTCAGGACGGCATGCGCCC
CATCTGCCTGATCCGGGTGAAGCGATCCATCACTTGCCTGACGCCGAGTTTCTGAAAGGGCTGC
GCACGCTGAACGGCACGCCGAAGGAGCTTTTTGAAAACGAGGAAAACGAAGAGATCTTGCAAAT
GCTTCTGCCGATGCTGCGGGCAGATTTCACCATCTGCGAGCAGTATCAATACCAGGAGGAAGAG
CCGCTCGGTTGCGGATTGACGGCGATTGGCGGTTGGCAGGACCCCGACATTACCGTGGCGCACA
TGGAAGCATGGAGAAAGCACACCAGTGCTTCGTTCCAGATGCACATGCTGCAAGGCGACCATTT
CTTTCTCCATTCGGAACAGGAACAACTTTTGGCGATCATCGAATCAACATTACAAAGCTATCTG
GTTGGGTACAGGGGGATCGGATGA  (SEQ ID NO: 7)

Fig. 6B

A
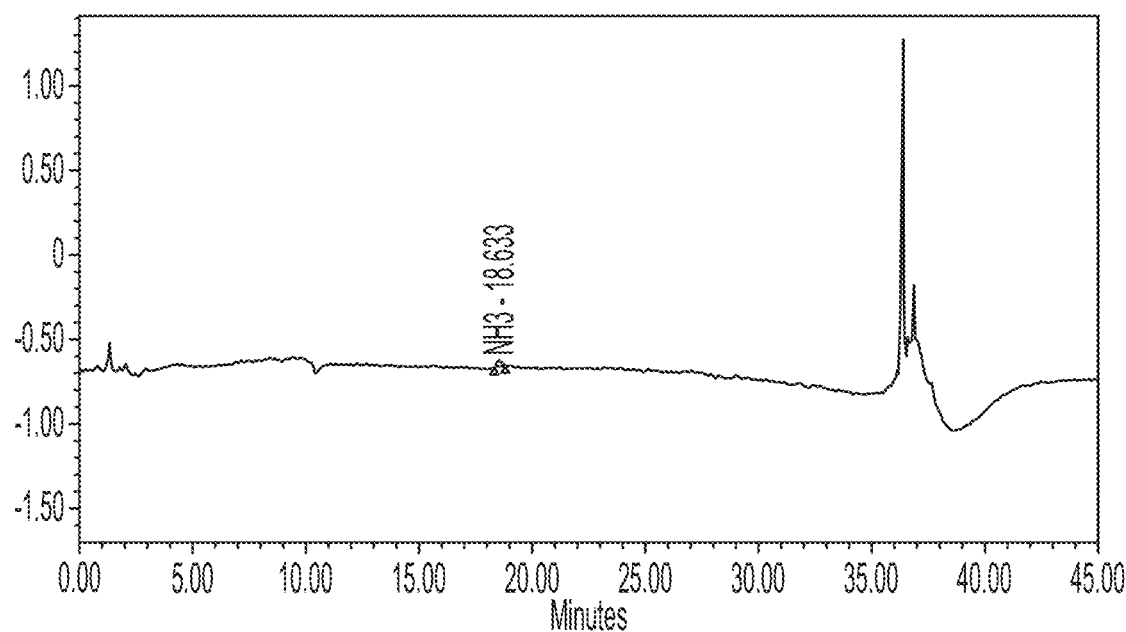
B
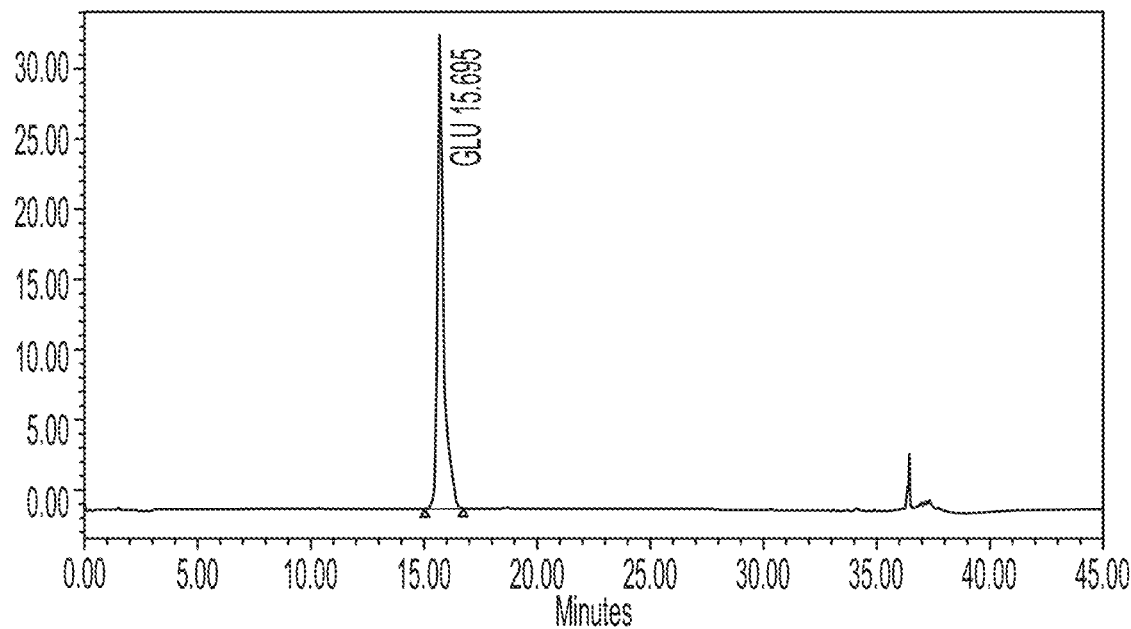
Fig. 8

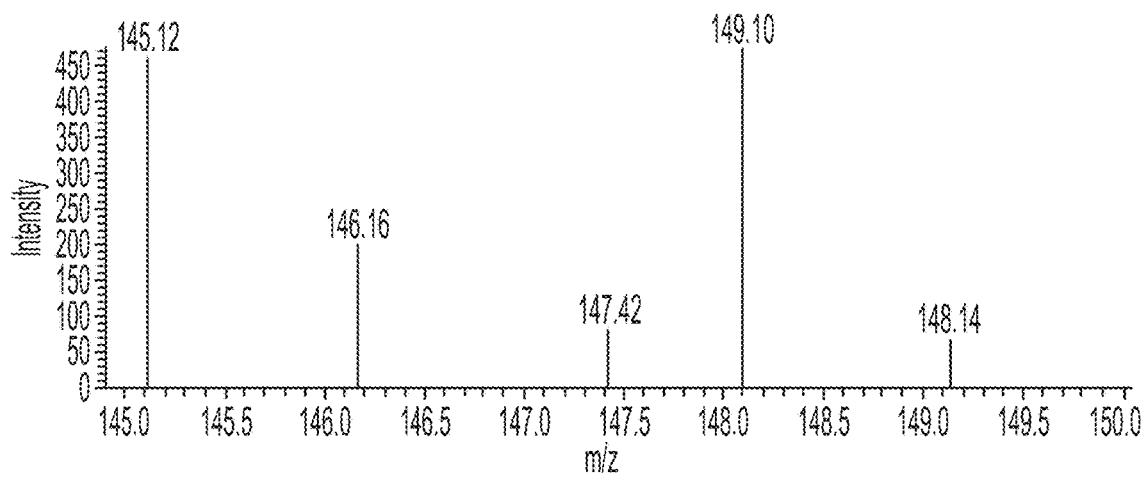
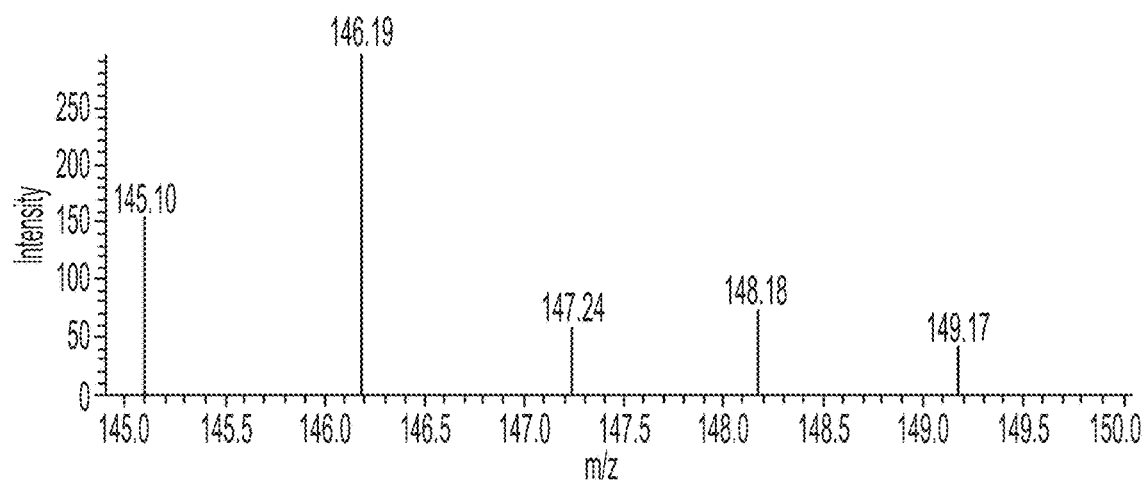
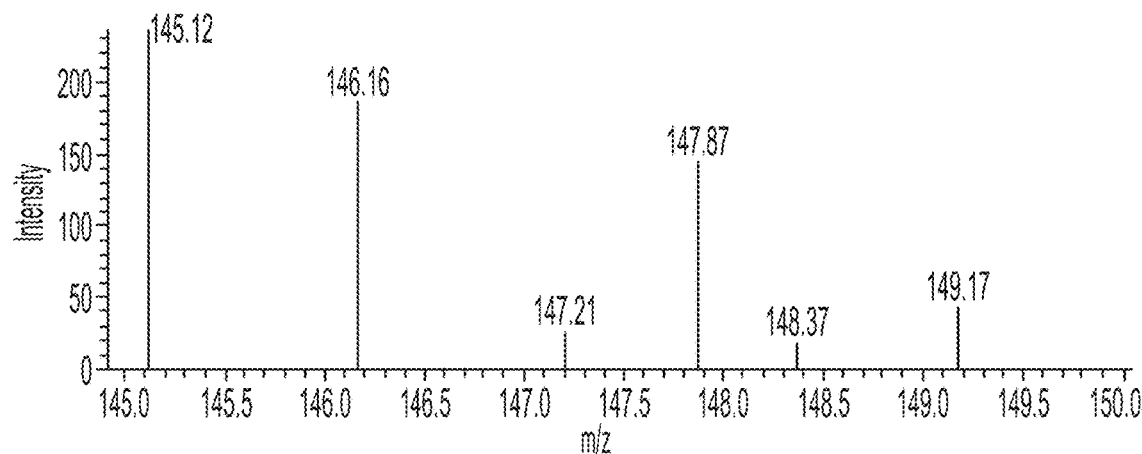
Fig. 14

SEQUENCE LISTING

```
<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ile, Val, Ser, Pro, Ala, Asp, Asn, or Lys
<220> FEATURE:
<221> NAME/KEY: MOD_RES
<222> LOCATION: (2)..(10)
<223> OTHER INFORMATION: Any amino acid
<220> FEATURE:
<221> NAME/KEY: SITE
<222> LOCATION: (2)..(10)
<223> OTHER INFORMATION: May or may not be present
<220> FEATURE:
<221> NAME/KEY: MOD_RES
<222> LOCATION: (11)..(11)
<223> OTHER INFORMATION: Any amino acid except Pro
<220> FEATURE:
<221> NAME/KEY: MOD_RES
<222> LOCATION: (12)..(13)
<223> OTHER INFORMATION: Any amino acid
<220> FEATURE:
<221> NAME/KEY: SITE
<222> LOCATION: (12)..(13)
<223> OTHER INFORMATION: May or may not be present
<220> FEATURE:
```

```
<221> NAME/KEY: MOD_RES
<222> LOCATION: (15)..(15)
<223> OTHER INFORMATION: Pro, Ser, Thr, Ala, Gly, Asn, Cys, or Val
<220> FEATURE:
<221> NAME/KEY: MOD_RES
<222> LOCATION: (16)..(16)
<223> OTHER INFORMATION: Ser, Thr, Ala, Gly, Asn, Gln, Cys, Ile, Val, or
      Met
<220> FEATURE:
<221> NAME/KEY: MOD_RES
<222> LOCATION: (17)..(17)
<223> OTHER INFORMATION: Ser, Thr, Ala, Gly, or Cys
<220> FEATURE:
<221> NAME/KEY: MOD_RES
<222> LOCATION: (19)..(19)
<223> OTHER INFORMATION: Any amino acid except Pro or Cys
<220> FEATURE:
<221> NAME/KEY: MOD_RES
<222> LOCATION: (20)..(20)
<223> OTHER INFORMATION: Ser, Ala, Gly, Phe, Tyr, or Arg
<220> FEATURE:
<221> NAME/KEY: MOD_RES
<222> LOCATION: (21)..(21)
<223> OTHER INFORMATION: Leu, Ile, Val, Met, Ser, Thr, Ala, Gly, or Asp
<220> FEATURE:
<221> NAME/KEY: MOD_RES
<222> LOCATION: (22)..(22)
<223> OTHER INFORMATION: Any amino acid
<220> FEATURE:
<221> NAME/KEY: SITE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Any amino acid except Lys
<220> FEATURE:
<221> NAME/KEY: MOD_RES
<222> LOCATION: (24)..(24)
<223> OTHER INFORMATION: Leu, Ile, Val, Met, Phe, Tyr, or Trp
<220> FEATURE:
<221> NAME/KEY: MOD_RES
<222> LOCATION: (25)..(25)
<223> OTHER INFORMATION: Any amino acid except Asp
<220> FEATURE:
<221> NAME/KEY: MOD_RES
<222> LOCATION: (26)..(26)
<223> OTHER INFORMATION: Any amino acid
<220> FEATURE:
<221> NAME/KEY: SITE
<222> LOCATION: (26)..(26)
<223> OTHER INFORMATION: May or may not be present
<220> FEATURE:
<221> NAME/KEY: MOD_RES
<222> LOCATION: (27)..(27)
<223> OTHER INFORMATION: Any amino acid except Tyr or Arg
<220> FEATURE:
<221> NAME/KEY: MOD_RES
<222> LOCATION: (28)..(28)
<223> OTHER INFORMATION: Leu, Ile, Val, Met, Phe, Tyr, Trp, Gly, Ala,
      Pro, Thr, His, or Gln
<220> FEATURE:
<221> NAME/KEY: MOD_RES
<222> LOCATION: (29)..(29)
<223> OTHER INFORMATION: Gly, Ser, Ala, Cys, Gln, Arg, His, or Met

<400> SEQUENCE: 1

Xaa Xaa Xaa Xaa Xaa Xaa Xaa Xaa Xaa Xaa Xaa Xaa Xaa Tyr Xaa Xaa
1               5                   10                  15

Xaa Lys Xaa Xaa Xaa Xaa Xaa Xaa Xaa Xaa Xaa Xaa Xaa
            20                  25

<210> SEQ ID NO 2
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Conserved sequence in adenylation domains

<400> SEQUENCE: 2

Thr Ser Gly Ser Thr Gly Asn Pro Lys Gly
1               5                   10

<210> SEQ ID NO 3
<211> LENGTH: 1847
<212> TYPE: PRT
<213> ORGANISM: Brevibacillus brevis

<400> SEQUENCE: 3

Asp Val Ser Val Ser Glu Ile Trp Gln Ala Leu Leu Ser Gly Gly Thr
1               5                   10                  15

Leu Val Ile Glu Asp Arg Glu Ser Leu Leu Pro Gly Pro Asp Leu Val
                20                  25                  30

Arg Thr Leu Arg Glu Arg Ile Ser Lys Val Ser Met Ala Ser Ser
            35                  40                  45

Leu Leu Ala Ser Leu Pro Val Ala Glu Tyr Pro Asp Leu Ala Val Leu
        50                  55                  60

Glu Val Gly Gly Asp Ala Cys Ser Arg Glu Leu Val Ala Arg Tyr Ala
65                  70                  75                  80

Thr Gly Arg Lys Phe Phe Asn Cys Tyr Gly Pro Thr Glu Ala Thr Val
                85                  90                  95

Gly Thr Val Ile Lys Gln Leu Thr Leu Asp Asp Thr Pro Thr Ile
            100                 105                 110

Gly Arg Pro Phe Pro Asn Thr Lys Leu Tyr Val Leu Asp Gln Asn Arg
        115                 120                 125

Lys Pro Val Pro Val Gly Val Pro Gly Glu Leu Tyr Ile Gly Gly Glu
        130                 135                 140

Cys Leu Ala Arg Gly Tyr Trp Asn Arg Pro Glu Leu Thr Ala Glu Arg
145                 150                 155                 160

Phe Val Ala Asn Pro Phe Gly Gln Pro Gly Glu Arg Leu Tyr Arg Thr
                165                 170                 175

Gly Asp Leu Val Arg Tyr Leu Pro Asp Gly Asn Val Asp Tyr Leu Gly
            180                 185                 190

Arg Phe Asp Asp Gln Val Lys Ile Arg Gly Tyr Arg Ile Glu Leu Gly
        195                 200                 205

Glu Ile Ala Glu Ala Leu Arg Gln His Ala Ala Ile Arg Glu Ala Val
    210                 215                 220

Val Leu Ala Arg Glu Val Arg Pro Gly Asp Lys Arg Leu Ala Ala Tyr
225                 230                 235                 240

Leu Thr Ser Ala Ala Glu Gln Glu Leu Ser Val Asp Glu Ile Lys Gln
                245                 250                 255

Trp Leu Lys Glu Lys Leu Pro Asp Tyr Met Val Pro Ala Ser Tyr Thr
            260                 265                 270

Trp Leu Pro Ala Ile Pro Leu Asn Val Asn Gly Lys Val Asp Arg Lys
        275                 280                 285

Ala Leu Pro Ala Pro Asp Trp Gly Gln Ile Thr Ala Ala Tyr Val Ala
    290                 295                 300

Pro Arg Asn Pro Leu Glu Glu Met Ile Ala Asn Val Phe Ala Glu Val
305                 310                 315                 320
```

```
Leu Ala Val Glu Lys Val Gly Ile Asp Asp Asn Phe Phe Glu Leu Gly
            325                 330                 335
Gly His Ser Leu Leu Ala Thr Gln Thr Val Ser Arg Leu Arg Glu Ile
            340                 345                 350
Val Gly Val Glu Leu Gln Leu Arg Thr Leu Phe Glu His Pro Thr Val
            355                 360                 365
Ala Gly Leu Gly Glu Gln Leu Glu Leu Thr Lys Gln Ser Ser Arg
            370                 375             380
Lys Leu Ala Pro Pro Ile Gly Lys Val Ser Lys Glu Pro Leu Pro
385                 390                 395                 400
Leu Ser Phe Thr Gln Gln Arg Leu Trp Phe Leu Glu Gln Phe Thr Gln
            405                 410                 415
Asn Ser Ser Ile Asn Asn Ile Pro Ser Phe Leu Arg Ile Gln Gly Glu
            420                 425                 430
Leu Asp Val Ala Ala Trp Glu Ala Ser Phe Ser Ala Ile Ile Leu Arg
            435                 440                 445
His Glu Ser Leu Arg Thr Ser Phe Glu Val Arg Asp Gly Arg Pro Val
            450                 455                 460
Gln Val Ile Gln Pro His Gly Asp Trp Ala Met Thr Arg Ile Asp Leu
465                 470                 475                 480
Arg Ala Leu Glu Pro Ala Glu Arg Glu Ala Glu Ile Lys Arg Leu Ala
            485                 490                 495
Glu Gln Ala Ile Val Gln Pro Phe Asp Leu Thr Lys Gly Leu Leu Leu
            500                 505                 510
Arg Ala Ser Leu Val Gln Leu Asp Ala Asn Asp Phe Val Phe Leu Phe
            515                 520                 525
Val Met His His Ile Ala Ser Asp Gly Trp Ser Met Gly Ile Leu Leu
            530                 535                 540
Ser Glu Leu Met Thr Asn Tyr Lys Ala Phe Arg Gln Gly Glu Ala Ser
545                 550                 555                 560
Pro Leu Gly Glu Leu Pro Ile Gln Tyr Ala Asp Phe Ala Val Trp Gln
            565                 570                 575
Arg Glu Trp Leu Ser Gly Glu Val Leu Ala Glu Gln Leu Gly Tyr Trp
            580                 585                 590
Arg Glu Lys Leu Lys Gly Ser Glu Pro Leu Leu Gln Leu Pro Thr Asp
            595                 600                 605
Arg Pro Arg Pro Val Gln Thr Tyr Glu Gly Glu Lys Met Ser Val
            610                 615                 620
Gln Phe Gly Ala Glu Leu Leu Lys Gln Leu Gln Ser Leu Ser Arg Lys
625                 630                 635                 640
Glu Gly Ala Thr Leu Phe Met Thr Leu Phe Ala Ala Phe Gln Thr Leu
            645                 650                 655
Leu Tyr Arg Tyr Thr Asn Gln Asp Asp Ile Leu Val Gly Thr Pro Ile
            660                 665                 670
Ala Gly Arg Asn Lys Gln Glu Thr Glu Gln Leu Ile Gly Tyr Phe Ile
            675                 680                 685
Asn Thr Leu Val Leu Arg Thr Asp Met Ser Gly His Pro Ser Phe Arg
            690                 695                 700
Glu Leu Leu Ala Arg Val Arg Glu Thr Ala Leu Glu Ala Tyr Ala His
705                 710                 715                 720
Gln Asp Val Pro Phe Glu Lys Leu Leu Asp Glu Leu Gln Leu Glu Arg
            725                 730                 735
Ser Met Ser Tyr Ser Pro Leu Phe Gln Val Met Phe Ile Leu Gln Asn
```

```
                    740             745                 750
Ile Pro Val Gln Ala Glu Pro Ala Gly Asp Ile Gln Leu Ser Ser Phe
                755                 760                 765

Asp Leu Glu Leu Gly Ala Val Thr Ser Lys Phe Asp Met Thr Val Thr
770                 775                 780

Met Val Glu Thr Pro Asp Gly Leu Leu Ala Thr Leu Glu Tyr Asn Lys
785                 790                 795                 800

Ala Leu Phe Asp Ser Ser Thr Ile Thr Arg Met Val Glu His Phe His
                805                 810                 815

Lys Leu Met Glu Glu Ile Val Ala Asn Pro Asp Gln Ser Ile Thr Leu
                820                 825                 830

Leu Pro Leu Met Arg Glu Glu Glu Gln Leu Leu Ile Thr Glu Trp
                835                 840                 845

Asn Arg Thr Glu Val Pro Tyr Ser Arg Glu Lys Cys Val His Glu Met
                850                 855                 860

Ile Glu Glu Met Val Ser Lys Ala Pro Asp Ser Ile Ala Leu Ile Val
865                 870                 875                 880

Gly Glu Gln Arg Val Thr Tyr Gly Glu Leu Asn Arg Gln Ala Asn Gln
                885                 890                 895

Leu Ala His Tyr Leu Arg Lys Gln Gly Val Gly Pro Glu Val Leu Val
                900                 905                 910

Gly Ile Cys Ala Glu Arg Thr Val Glu Met Met Ile Gly Leu Leu Ala
                915                 920                 925

Ile Leu Lys Ala Gly Gly Ala Tyr Val Pro Ile Asp Pro Ala Tyr Pro
                930                 935                 940

Ala Glu Arg Ile Ala Tyr Ile Ile Gly His Ser Gln Ile Pro Val Leu
945                 950                 955                 960

Leu Thr Gln Glu His Leu Leu Pro Thr Leu Pro Glu His Gln Ala Lys
                965                 970                 975

Val Ile Cys Leu Asp Arg Asp Trp Ala Thr Val Ala Val Glu Ser Glu
                980                 985                 990

Glu Asn Pro Gly Lys Leu Ala Thr Ser Asp Asn Leu Ile Tyr Val Ile
                995                 1000                1005

Tyr Thr Ser Gly Ser Thr Gly Asn Pro Lys Gly Val Ala Leu Glu
                1010                1015                1020

His Arg Ser Val Ile Tyr Phe Leu Ser Trp Ala His Asp Thr Tyr
                1025                1030                1035

Thr Pro Glu Glu Met Ser Gly Val Leu Phe Ser Thr Ser Ile Cys
                1040                1045                1050

Phe Asp Leu Ser Val Tyr Glu Met Phe Ala Thr Leu Thr Met Gly
                1055                1060                1065

Gly Lys Val Ile Met Ala Glu Asn Ala Leu Gln Leu Pro Ala Leu
                1070                1075                1080

Pro Ala Ala Asp Gln Val Thr Leu Val Asn Thr Val Pro Ser Ala
                1085                1090                1095

Ala Thr Glu Leu Val Arg Met Lys Gly Ile Pro Ala Ser Val Arg
                1100                1105                1110

Val Ile Asn Leu Cys Gly Glu Pro Leu Ser Asn Arg Leu Ala Gln
                1115                1120                1125

Glu Leu Tyr Ala Phe Pro His Val Glu Lys Val Phe Asn Leu Tyr
                1130                1135                1140

Gly Pro Thr Glu Asp Thr Val Tyr Ser Thr His Ala Ile Val Thr
                1145                1150                1155
```

```
Lys Gly Ala Thr Asn Glu Pro Leu Ile Gly Arg Pro Gln Phe Asn
    1160            1165            1170

Thr His Val Phe Val Leu Asp Ser His Arg Lys Pro Val Pro Val
    1175            1180            1185

Gly Val Pro Gly Glu Leu Tyr Leu Ser Gly Ser Gly Leu Ala Arg
    1190            1195            1200

Gly Tyr Leu His Arg Pro Asp Leu Thr Ala Glu Arg Phe Val Gln
    1205            1210            1215

Asn Pro Phe Arg Glu Pro Gly Ala Arg Met Tyr Arg Thr Gly Asp
    1220            1225            1230

Leu Val Arg Tyr Leu Pro Asp Gly Asn Leu Gln Phe Val Gly Arg
    1235            1240            1245

Val Asp Tyr Gln Val Lys Ile Arg Gly Tyr Arg Ile Glu Leu Gly
    1250            1255            1260

Glu Ile Glu Ser Val Leu Asn Arg Phe Pro Gly Val Lys Glu Val
    1265            1270            1275

Val Leu Leu Ala Arg Glu Asp Arg Glu Gly Asp Lys Cys Leu Val
    1280            1285            1290

Ala Tyr Ile Val Phe Glu Ala Asp Cys Thr Ser Lys Ile His Asp
    1295            1300            1305

Leu Asn His Phe Leu Ala Asp Lys Leu Pro Ala Tyr Met Ile Pro
    1310            1315            1320

Gln His Tyr Met Ile Leu Asp Ser Leu Pro Lys Thr Pro Asn Gly
    1325            1330            1335

Lys Leu Asp Arg Lys Ala Leu Pro Lys Pro Glu Tyr Asp Arg Ser
    1340            1345            1350

Glu Ala Gly Val Glu Tyr Val Ala Pro Gln Thr Pro Val Glu Ile
    1355            1360            1365

Met Leu His Ala His Trp Ala Ala Val Leu Glu Met Glu Thr Ile
    1370            1375            1380

Gly Val His Asp Asn Phe Phe Glu Ile Gly Gly His Ser Leu Leu
    1385            1390            1395

Ala Thr Gln Leu Ile Phe Lys Val Arg Glu Glu Leu Gln Leu Glu
    1400            1405            1410

Val Pro Leu Arg Ile Leu Phe Glu Thr Pro Thr Ile Ala Gly Met
    1415            1420            1425

Ala Lys Thr Ile Glu Glu Ile Ile Lys His Gly Leu Thr Ser Val
    1430            1435            1440

Ser Gln Glu Ile Asp Ala Lys Gly Leu Gln Asp Glu Val Ala Leu
    1445            1450            1455

Asp Pro Ala Ile Leu Ala Glu Gln Pro Tyr Glu Gly Asp Pro Ser
    1460            1465            1470

Gln Phe Gln Ala Ala Leu Leu Thr Gly Ala Thr Gly Phe Leu Gly
    1475            1480            1485

Ala Phe Leu Leu Arg Asp Leu Leu Gln Met Thr Asp Ala Asp Ile
    1490            1495            1500

Tyr Cys Leu Val Arg Ala Ser Gly Glu Glu Gly Leu Ala Arg
    1505            1510            1515

Leu Arg Lys Thr Leu Gln Leu Tyr Glu Leu Trp Asp Glu Ala Gln
    1520            1525            1530

Ala His Arg Ile Ile Pro Val Ile Gly Asp Leu Ala Gln Pro Arg
    1535            1540            1545
```

-continued

```
Leu Gly Leu Ser Ala Gly Gln Phe Asp Ala Leu Ala Ala Thr Val
    1550            1555                1560

Asp Val Ile Tyr His Asn Gly Ala Leu Val Asn Phe Val Tyr Pro
    1565            1570                1575

Tyr Ala Ala Leu Lys Lys Ala Asn Val Ile Gly Thr Glu Glu Ile
    1580            1585                1590

Ile Arg Arg Glu Leu Ala Ala Ala Lys Lys Thr Lys Pro Val His
    1595            1600                1605

Phe Val Ser Thr Ile Phe Thr Phe Ala Ser Glu Glu Gly Glu Glu
    1610            1615                1620

Ser Val Ala Val Arg Glu Glu Asp Met Pro Glu Asn Ser Arg Ile
    1625            1630                1635

Leu Thr Ser Gly Tyr Thr Gln Ser Lys Trp Val Ala Glu His Ile
    1640            1645                1650

Val Asn Leu Ala Arg Gln Arg Gly Ile Pro Thr Ala Ile Tyr Arg
    1655            1660                1665

Cys Gly Arg Met Thr Gly Asp Ser Glu Thr Gly Ala Cys Gln Lys
    1670            1675                1680

Asp Asp Leu Met Trp Arg Ile Ala Ala Gly Ile Ile Asp Leu Gly
    1685            1690                1695

Lys Ala Pro Asp Met Ser Gly Asp Leu Asp Met Met Pro Val Asp
    1700            1705                1710

Phe Ala Ser Lys Gly Ile Val His Leu Ser Met Thr Glu His Ser
    1715            1720                1725

Val Asn Ser Asn Phe His Leu Leu Asn Pro Asn Ala Thr Asp Tyr
    1730            1735                1740

Asp Asp Leu Ile Ala Ala Ile Glu Asn Lys Gly Phe Glu Leu Glu
    1745            1750                1755

Arg Val Thr Met Asp Glu Trp Ile Glu Ala Val Gln Glu Asp Ala
    1760            1765                1770

Lys Asp Lys Gly Met Asp Ala Asn Ser Ala Ala Pro Leu Gly Asn
    1775            1780                1785

Leu Phe Ser Asp Gly His Ser Ser Arg Gly Ser Val Val Tyr Val
    1790            1795                1800

Gly Asn Lys Thr Thr Arg Leu Leu Arg Gln Ala Asp Ile Glu Cys
    1805            1810                1815

Pro Glu Ile Asp Glu Glu Val Phe Ala Lys Val Leu Asp Tyr Phe
    1820            1825                1830

Ala Arg Thr Gly Gln Leu Arg Val Thr Gln Asn Thr Arg Asn
    1835            1840                1845

<210> SEQ ID NO 4
<211> LENGTH: 504
<212> TYPE: PRT
<213> ORGANISM: Brevibacillus brevis

<400> SEQUENCE: 4

Val His Glu Met Ile Glu Glu Met Val Ser Lys Ala Pro Asp Ser Ile
1               5                   10                  15

Ala Leu Ile Val Gly Glu Gln Arg Val Thr Tyr Gly Glu Leu Asn Arg
            20                  25                  30

Gln Ala Asn Gln Leu Ala His Tyr Leu Arg Lys Gln Gly Val Gly Pro
        35                  40                  45

Glu Val Leu Val Gly Ile Cys Ala Glu Arg Thr Val Glu Met Met Ile
    50                  55                  60
```

```
Gly Leu Leu Ala Ile Leu Lys Ala Gly Gly Ala Tyr Val Pro Ile Asp
 65                  70                  75                  80

Pro Ala Tyr Pro Ala Glu Arg Ile Ala Tyr Ile Ile Gly His Ser Gln
                 85                  90                  95

Ile Pro Val Leu Leu Thr Gln Glu His Leu Leu Pro Thr Leu Pro Glu
                100                 105                 110

His Gln Ala Lys Val Ile Cys Leu Asp Arg Asp Trp Ala Thr Val Ala
                115                 120                 125

Val Glu Ser Glu Glu Asn Pro Gly Lys Leu Ala Thr Ser Asp Asn Leu
130                 135                 140

Ile Tyr Val Ile Tyr Thr Ser Gly Ser Thr Gly Asn Pro Lys Gly Val
145                 150                 155                 160

Ala Leu Glu His Arg Ser Val Ile Tyr Phe Leu Ser Trp Ala His Asp
                165                 170                 175

Thr Tyr Thr Pro Glu Glu Met Ser Gly Val Leu Phe Ser Thr Ser Ile
                180                 185                 190

Cys Phe Asp Leu Ser Val Tyr Glu Met Phe Ala Thr Leu Thr Met Gly
                195                 200                 205

Gly Lys Val Ile Met Ala Glu Asn Ala Leu Gln Leu Pro Ala Leu Pro
210                 215                 220

Ala Ala Asp Gln Val Thr Leu Val Asn Thr Val Pro Ser Ala Ala Thr
225                 230                 235                 240

Glu Leu Val Arg Met Lys Gly Ile Pro Ala Ser Val Arg Val Ile Asn
                245                 250                 255

Leu Cys Gly Glu Pro Leu Ser Asn Arg Leu Ala Gln Glu Leu Tyr Ala
                260                 265                 270

Phe Pro His Val Glu Lys Val Phe Asn Leu Tyr Gly Pro Thr Glu Asp
                275                 280                 285

Thr Val Tyr Ser Thr His Ala Ile Val Thr Lys Gly Ala Thr Asn Glu
                290                 295                 300

Pro Leu Ile Gly Arg Pro Gln Phe Asn Thr His Val Phe Val Leu Asp
305                 310                 315                 320

Ser His Arg Lys Pro Val Pro Val Gly Val Pro Gly Glu Leu Tyr Leu
                325                 330                 335

Ser Gly Ser Gly Leu Ala Arg Gly Tyr Leu His Arg Pro Asp Leu Thr
                340                 345                 350

Ala Glu Arg Phe Val Gln Asn Pro Phe Arg Glu Pro Gly Ala Arg Met
                355                 360                 365

Tyr Arg Thr Gly Asp Leu Val Arg Tyr Leu Pro Asp Gly Asn Leu Gln
                370                 375                 380

Phe Val Gly Arg Val Asp Tyr Gln Val Lys Ile Arg Gly Tyr Arg Ile
385                 390                 395                 400

Glu Leu Gly Glu Ile Glu Ser Val Leu Asn Arg Phe Pro Gly Val Lys
                405                 410                 415

Glu Val Val Leu Leu Ala Arg Glu Asp Arg Glu Gly Asp Lys Cys Leu
                420                 425                 430

Val Ala Tyr Ile Val Phe Glu Ala Asp Cys Thr Ser Lys Ile His Asp
                435                 440                 445

Leu Asn His Phe Leu Ala Asp Lys Leu Pro Ala Tyr Met Ile Pro Gln
                450                 455                 460

His Tyr Met Ile Leu Asp Ser Leu Pro Lys Thr Pro Asn Gly Lys Leu
465                 470                 475                 480
```

Asp Arg Lys Ala Leu Pro Lys Pro Glu Tyr Asp Arg Ser Glu Ala Gly
            485                 490                 495

Val Glu Tyr Val Ala Pro Gln Thr
            500

<210> SEQ ID NO 5
<211> LENGTH: 1512
<212> TYPE: DNA
<213> ORGANISM: Brevibacillus brevis

<400> SEQUENCE: 5

| | | | | | |
|---|---|---|---|---|---|
| gtccatgaaa | tgatcgagga | aatggtgagc | aaagcaccgg | acagcatcgc | cctgatcgtg | 60 |
| ggtgagcagc | gcgtaacgta | cggcgagttg | aacaggcagg | cgaaccaact | ggcgcattat | 120 |
| ttgcgcaagc | agggagttgg | cccggaagtg | ctcgtcggca | tatgcgcaga | gcggacggtc | 180 |
| gaaatgatga | tcggactttt | ggcgatcctc | aaggctggcg | gcgcttatgt | gcccatcgat | 240 |
| ccggcgtatc | cggcagagcg | gattgcctac | atcatcgggc | attcgcaaat | tccggttctg | 300 |
| cttacgcaag | aacatctgct | gccgacgctg | cctgagcacc | aggcgaaagt | gatttgcctg | 360 |
| gatcgcgatt | gggcaacggt | agcggttgag | tccgaggaaa | atccaggcaa | gcttgcgacc | 420 |
| tccgacaatt | tgatctacgt | catttacaca | tcaggctcta | ccggcaatcc | aaaaggggtg | 480 |
| gcactggaac | accgcagcgt | tatttacttc | ctctcttggg | cgcatgacac | ttatacgcct | 540 |
| gaggagatga | gcgcgtcct | gttctccaca | tcgatctgct | tcgacttgtc | tgtgtacgag | 600 |
| atgtttgcca | ccttgaccat | gggcggcaaa | gtgatcatgg | cggaaaatgc | cttgcaactg | 660 |
| ccagccttgc | cagcagccga | tcaggtgacg | ctcgtcaata | cagtgccatc | ggccgcgaca | 720 |
| gagcttgtcc | gcatgaaggg | cataccggct | tcggtgcgtg | tcatcaactt | gtgcggcgag | 780 |
| ccgcttttcca | accgattggc | acaagagctg | tacgccttcc | cgcacgtgga | aaaagtgttc | 840 |
| aatctgtacg | ggccgacgga | ggataccgtt | tactccacac | acgcgatcgt | gacaaaagga | 900 |
| gcgacgaacg | agccgctaat | cggcagaccg | cagttcaata | cgcacgtctt | cgtgctggac | 960 |
| agccaccgca | agcctgtgcc | agtaggggtg | ccgggggaat | tgtacctcag | cggttccggc | 1020 |
| ttggcgcgcg | gctacttgca | ccgtcccgat | ctgaccgcag | aacgttttgt | gcaaaatccg | 1080 |
| ttccgcgaac | cgggagcgag | aatgtaccgg | actggcgacc | tcgtgcgcta | cttgccggac | 1140 |
| ggaaatctcc | agtttgtcgg | ccgcgtcgat | taccaggtga | aaatccgcgg | ctaccgcatc | 1200 |
| gagctgggcg | aaatcgagtc | cgtgctgaac | cgcttcccgg | gcgtcaaaga | ggtcgtgctg | 1260 |
| ctcgcccgtg | aagatcggga | aggcgacaag | tgcctggttg | cgtacatcgt | gttcgaggcc | 1320 |
| gattgcacaa | gcaagattca | cgatctgaat | cacttttttgg | ccgacaagct | gccagcgtac | 1380 |
| atgattccgc | agcattacat | gattttggac | agcttgccga | agacgccaaa | cggcaaactg | 1440 |
| gaccgcaaag | cgctgccgaa | gccggaatac | gaccgctcgg | aagcaggagt | cgaatacgtc | 1500 |
| gcgccgcaaa | cg | | | | | 1512 |

<210> SEQ ID NO 6
<211> LENGTH: 263
<212> TYPE: PRT
<213> ORGANISM: Brevibacillus brevis

<400> SEQUENCE: 6

Met Gln Lys Thr His Val Ser Pro Ser Arg Trp Leu Leu Ser Pro Lys
1               5                   10                  15

Met Thr Ala Glu Ala Glu Val Leu Leu Phe Ser Phe His Tyr Ala Gly
            20                  25                  30

Gly His Ala Gly Ile Tyr Arg Glu Trp Gln Lys Lys Leu Pro Val Gln
            35                  40                  45

Ile Gly Val Cys Pro Val Gln Leu Pro Gly Arg Ser Asn Arg Phe Met
        50                  55                  60

Glu Pro Tyr Tyr Thr Asp Leu Ser Val Met Ile Arg Glu Leu Ala Glu
65                  70                  75                  80

Ala Leu Leu Pro His Leu Asn Arg Pro Phe Ala Phe Phe Gly His Ser
                85                  90                  95

Met Gly Ala Leu Val Ser Phe Glu Leu Ala Arg Tyr Leu Arg Asn Gln
            100                 105                 110

Tyr Gly Ile Lys Pro Arg His Met Phe Ala Ser Gly Arg His Ala Pro
        115                 120                 125

His Leu Pro Asp Pro Gly Glu Ala Ile His His Leu Pro Asp Ala Glu
130                 135                 140

Phe Leu Lys Gly Leu Arg Thr Leu Asn Gly Thr Pro Lys Glu Leu Phe
145                 150                 155                 160

Glu Asn Glu Glu Asn Glu Glu Ile Leu Gln Met Leu Leu Pro Met Leu
                165                 170                 175

Arg Ala Asp Phe Thr Ile Cys Glu Gln Tyr Gln Tyr Gln Glu Glu Glu
            180                 185                 190

Pro Leu Gly Cys Gly Leu Thr Ala Ile Gly Gly Trp Gln Asp Pro Asp
        195                 200                 205

Ile Thr Val Ala His Met Glu Ala Trp Arg Lys His Thr Ser Ala Ser
210                 215                 220

Phe Gln Met His Met Leu Gln Gly Asp His Phe Phe Leu His Ser Glu
225                 230                 235                 240

Gln Glu Gln Leu Leu Ala Ile Ile Glu Ser Thr Leu Gln Ser Tyr Leu
                245                 250                 255

Val Gly Tyr Arg Gly Ile Gly
            260

<210> SEQ ID NO 7
<211> LENGTH: 792
<212> TYPE: DNA
<213> ORGANISM: Brevibacillus brevis

<400> SEQUENCE: 7
atgcaaaaga cacacgtttc cccgagccgt tggctgcttt ccccgaaaat gacggcggag      60
gcagaggtgc tttattcag ctttcactat gcaggcggac atgctggcat ctatcgcgag     120
tggcaaaaaa agctgcctgt gcagatcggg gtgtgccccg tgcagctgcc aggcaggagc     180
aatcggttta tggagccgta ctacaccgac ttgtccgtga tgatccgcga gctggcggaa     240
gcgcttttgc cccatctgaa tcgcccgttt gccttttttg gacatagcat gggagcgctg     300
gtcagcttcg agctggccag atatttgcgc aaccagtacg gtatcaagcc gcggcatatg     360
ttcgcttcag gacggcatgc gccccatctg cctgatccgg gtgaagcgat ccatcacttg     420
cctgacgccg agtttctgaa agggctgcgc acgctgaacg gcacgccgaa ggagcttttt     480
gaaaacgagg aaaacgaaga gatcttgcaa atgcttctgc cgatgctgcg ggcagatttc     540
accatctgcg agcagtatca ataccaggag gaagagccgc tcggttgcgg attgacggcg     600
attggcggtt ggcaggaccc cgacattacc gtggcgcaca tggaagcatg gagaaagcac     660
accagtgctt cgttccagat gcacatgctg caaggcgacc atttctttct ccattcggaa     720

```
caggaacaac ttttggcgat catcgaatca acattacaaa gctatctggt tgggtacagg    780
gggatcggat ga                                                        792
```

GENERATION OF ACYL ALCOHOLS

CROSS-REFERENCE TO RELATED APPLICATIONS

The present application is a division of U.S. application Ser. No. 15/744,574 filed Jan. 12, 2018, U.S. Pat. No. 11,371,066, which is a 371 national stage entry of International Application No. PCT/US16/42157 filed July 13, 2016. which claims priority to and benefit of U.S. provisional patent application No. 62/191,571, filed Jul. 13, 2015, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on May 20, 2022, is named 2003320-0178_SL.txt and is 28,901 bytes in size.

BACKGROUND

Surfactants are currently manufactured from nonrenewable feedstocks (such as petroleum) or are manufactured from seed oils (such as palm oil), which contributes to rainforest destruction, as land is cleared to support palm plantation expansion. Use of raw materials to make surfactants also increases greenhouse gas pollution. In addition, current surfactant manufacturing methods require enormous quantities of heat, depend on hazardous processing steps (such as chlorination) and produce toxic byproducts and carcinogens.

For example, cocamide monoethanolamine (NEA) and cocamide diethanolamine (DEA) are widely used commercially as nonionic surfactants. These surfactants are typically produced by reacting fatty acid derived from coconut oil or palm oil with ethanolamine or diethanolamine. Ethanolamine and diethanolamine are produced on an industrial scale by reacting ethylene oxide with ammonia. The ethoxylation processes used to manufacture cocamide MEA and cocamide DEA result in the generation of the carcinogen 1,4-dioxane as a contaminant.

SUMMARY

In one aspect, the present disclosure encompasses the recognition that there is a need for "greener" methods of producing surfactants (including non-ionic surfactants), e.g., methods that do not lead to the formation of toxic substances. In one aspect, the present disclosure provides methods of generating acyl alcohols.

In certain embodiments, provided are methods comprising steps of: providing an acyl amino acid and treating the acyl amino acid with a reductase polypeptide so that an acyl alcohol is released. In some embodiments, both the providing and treating stems are performed in a cell expressing a reductase polypeptide that acts on the acyl amino acid. In some embodiments, the acyl amino acid is generated in the cell.

In some embodiments, the cell expresses an engineered polypeptide comprising a fatty acid linkage domain, a peptide synthetase domain, and a first reductase polypeptide. In some embodiments, the fatty acid linkage domain and the peptide synthetase domain are covalently linked. In some embodiments, the reductase polypeptide is covalently linked to the fatty acid linkage domain and the peptide synthetase domain. In some embodiments, the fatty acid linkage domain is a beta-hydroxy fatty acid linkage domain, e.g., a beta-hydroxy myristic acid linkage domain.

In some embodiments, the peptide synthetase domain comprises an adenylation domain and a thiolation domain, which adenylation domain and thiolation domain are covalently linked. In some embodiments, the adenylation domain is specific for glycine. In some embodiments, the adenylation domain is at least 70% identical at the amino acid level to the terminal adenylation domain of the gramicidin peptide synthetase from *Bacillus brevis*.

In some embodiments, the cell expresses a second reductase polypeptide distinct from the first reductase polypeptide. In some embodiments, the second reductase polypeptide is at least 70% identical at the amino acid level to the polypeptide produced from *Bacillus brevis* LgrE gene.

In some embodiments, the acyl alcohol is acyl ethanolamine, e.g., β-hydroxy myristoyl ethanolamine.

In some embodiments, the adenylation domain is specific for alanine. In some embodiments, the adenylation domain is at least 70% identical at the amino acid level to the reductase domain of the terminal mycobacterial glycopeptidedolipid peptide synthetase domain.

In some embodiments, the acyl alcohol is acyl alaninol.

In some embodiments, the adenylation domain is specific for serine.

In some embodiments, the acyl alcohol is acyl serinol.

In some embodiments, the cells are grown in a liquid media. In some embodiments, the acyl alcohol is secreted into the liquid media.

In some embodiments, the cell is a microbial cell, e.g., a *Bacillus* cell. In some embodiments, the *Bacillus* cell is a *Bacilus subtilis* cell.

In one aspect, the present disclosure compasses the recognition that, although acyl amino acids and acyl amino alcohols have commercial value, it may be desirable to produce derivative products from acyl amino acids or acyl amino alcohols, which may have commercial value in a wider market. In one aspect, the present disclosure provides methods of cleaving an acyl amino acid and/or acyl alcohol.

In certain embodiments, provided methods comprise steps of providing an acyl amino acid and/or an acyl alcohol and treating the acyl amino acid or acyl alcohol so that i) free fatty acid and ii) free amino acid and/or free alcohol is released.

In some embodiments, the treating step comprises incubating the acyl amino acid or acyl alcohol in acid. In some embodiments, the acyl amino acid or acyl alcohol is incubated in acid with heat.

In some embodiments, the treating step comprises incubating the acyl amino acid with an enzyme.

In some embodiments, methods further comprise a step of separating the released free fatty acid from the released free amino acid or free alcohol.

In some embodiments, methods further comprise a step of treating the free fatty acid so as to reduce the oxygen content of the free fatty acid.

In some embodiments, the free fatty acid is myristic acid.

In one aspect, provided are compositions comprising an acyl alcohol comprising a fatty acid covalently and directly linked to an alcohol. In some embodiments, the fatty is linked to the alcohol via an amide bond. In some embodiments, the a alcohol is an amino alcohol.

In one aspect, provided are compositions comprising an acyl alcohol and one or more components of an engineered microbial cell. In some embodiments, the one or more components comprise an intact microbial cell.

In one aspect, provided are engineered microbial cells comprising one or more polypeptides collectively comprising: a fatty acid linkage domain, a peptide synthetase domain, and one or more reductase polypeptides, which fatty acid linkage domain is covalently linked to the peptide synthetase domain, which fatty acid linkage domain and peptide synthetase domain collectively can produce an acyl amino acid, and which one or more reductase polypeptides are collectively capable of reducing the acyl amino acid to an acyl alcohol. In some embodiments, the engineered microbial cell lacks a thioesterase domain. In some embodiments, the microbial cell is a bacterial cell. In some embodiments, the bacterial cell is a *Bacillus* cell. In some embodiments, the *Bacillus* cell is a *Bacillus subtilis* cell.

BRIEF DESCRIPTION OF THE DRAWING

FIG. 1 depicts the structures of cocamide diethanolamine (DEA), cocamide monoethanolamine (MEA), and beta-hydroxyl myristoyl monoethanolamine (MEA).

FIG. 4 shows the amino acid sequence of SEQ ID NO: 3, corresponding to a portion of module 16 of the *Bacillus brevis* linear gramicidin synthetase complex. This sequence was obtained as described in Example 1 and includes the condensation, adenylation, thiolation and reductase domains of module 16. Underlining marks the beginning of the reductase domain according to Manavalan et al. ("Molecular modeling of the reductase domain to elucidate the reaction mechanism of reduction of peptidyl thioester into its corresponding alcohol in non-ribosomal peptide synthetases." *BMC Structural Biology*. 2010, 10:1. DOI: 10.1186/1472-6807-10-1, (the entire contents of which are herein incorporated by reference)), bold marks the NADPH-binding domain, and square boxes marks catalytic residues. A conserved adenylation domain sequence is bolded and underlined.

FIGS. 5A and 5B show the amino acid sequence (SEQ ID NO: 4) and nucleotide (coding) sequence (SEQ ID NO: 5), respectively, of the adenylation domain within SEQ ID NO: 3. In FIG. 5A, a conserved adenylation domain sequence is bolded and underlined.

FIGS. 6A and 6B show the amino acid sequence (SEQ ID NO: 6) and nucleotide sequence (SEQ ID NO: 7), respectively, of the IgrE gene from *Bacillus brevis*.

FIG. 7, panel A depicts LC/MS results, in which peaks corresponding to C12, C14, and C16 are visible. FIG. 7, panel B (inset) depicts the LC/MS signal plotted as a function of the amount of surfactant.

FIG. 8, comprising panels A and B, depicts results from the LC/MS experiment described in Example 3 analyzing derivative products from a reaction in which FA-Glu (an acyl amino acid) was treated with acid. FIG. 8, panel A, shows the results when FA-Glu was injected into the analyzer without any treatment. FIG. 8, panel B shows that a strong glutamate peak was detected after FA-Glu had been incubated with acid.

FIGS. 9, 10, 11, 12, and 13 show chromatograms for the detection of beta-hydroxy fatty acid compounds and FA-Glu for m/z rations of between 200 to 900, between 190 to 300, between 440 to 558, between 320 to 430, and between 682 to 848, respectively. FIG. 14 shows chromatograms for the detection of glutamate. Panel A in each figure depicts LC/MS data for FA-Glu incubated with porcine kidney acylase 1, panel B in each figure depicts LC/MS data for porcine kidney acylase 1 incubated without FA-Glu, and panel C in each figure depicts LC/IS data for FA-Glu incubated without porcine kidney acylase 1.

DEFINITIONS

Figure 2:
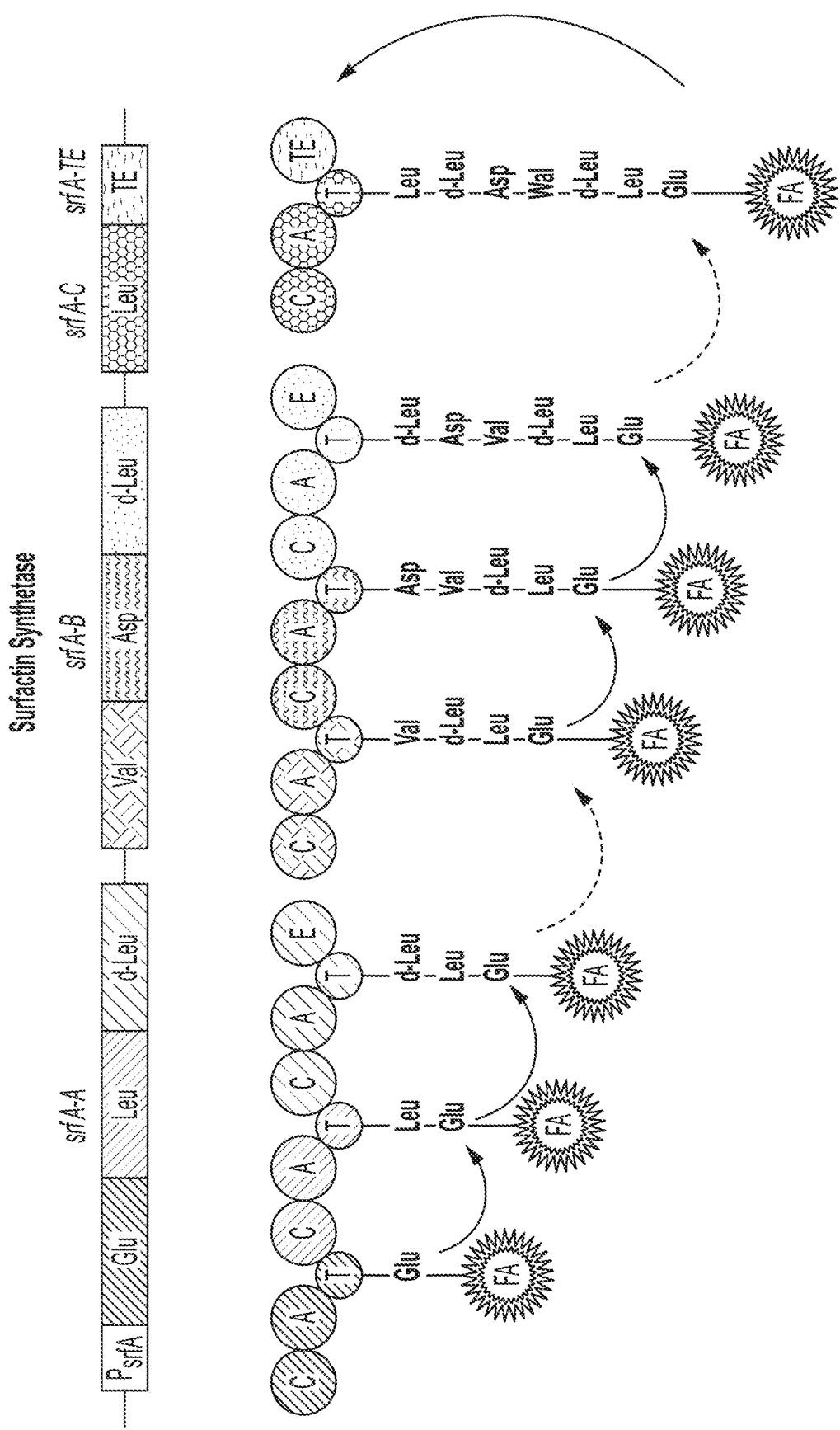
FIG. 2 depicts a schematic showing domains involved in the synthesis of surfactin by the surfactin synthetase from *Bacillus subtilis*.
Figure 3:
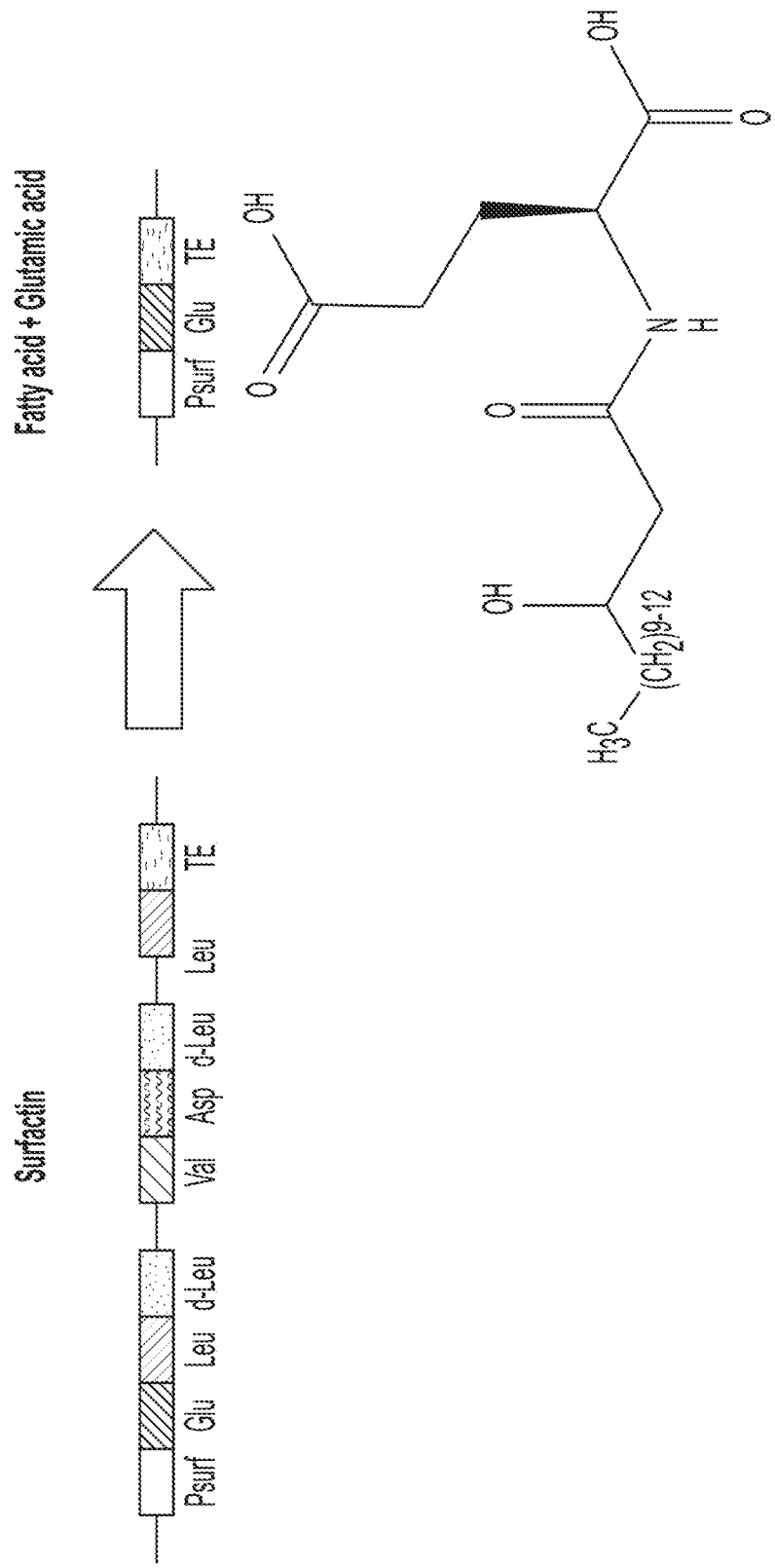
FIG. 3 depicts a schematic showing a mini-synthetase that links fatty acid to glutamic acid.

In this application, unless otherwise clear from context, (i) the term "a" may be understood to mean "at least one": (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "acyl amino acid" refers to an amino acid that is covalently linked to a fatty acid. In certain embodiments, acyl amino acids produced by compositions and methods as described, e.g., in U.S. Pat. No. 7,981,685, the entire contents of which are incorporated by reference herein. In certain embodiments, acyl amino acids are produced by employing engineered polypeptides comprising a peptide synthetase domain covalently linked to a fatty acid linkage domain. In certain embodiments, the fatty acid linkage domain is a beta-hydroxy fatty acid linkage domain. Typically, the identity of the amino acid moiety of the acyl amino acid is determined by the amino acid specificity of the peptide synthetase domain, and in particular by the adenylation domain within the peptide synthetase domain. For example, the peptide synthetase domain may specify any one of the naturally occurring amino acids known by those skilled the art to be used in ribosome-mediated polypeptide synthesis. Alternatively, the peptide synthetase domain may specify a non-naturally occurring amino acid, e.g. a modified amino acid. Similarly, the identity of the fatty acid moiety of the acyl amino acid is determined by the fatty acid specificity of the fatty acid linkage domain, such as for example a fatty acid linkage domain that is specific for a beta-hydroxy fatty acid. For example, the beta-hydroxy fatty acid may be any of a variety of naturally occurring or non-naturally occurring beta-hydroxy fatty acids.

As used herein, the term "acyl alcohol" refers to a compound in which an alcohol is covalently and directly linked to a fatty acid. As used herein, the term "acyl amino alcohol" refers to a type of acyl alcohol in which the alcohol that is covalently and directly linked to the fatty acid is an amino alcohol. In accordance with certain methods disclosed herein, an acyl alcohol is generated by treating an acyl amino acid with one or more reductase polypeptides such that an acyl alcohol is released. The acyl amino acid from which the acyl alcohol is generated and released can contain a naturally occurring amino acid or a non-naturally occurring amino acid. Possible fatty acid moieties of an acyl alcohol or an acyl amino alcohol include any fatty acid that can be specified by a fatty acid linkage domain (whether naturally occurring or engineered) of a peptide synthetase complex. In some embodiments, the fatty acid moiety is a beta-hydroxy fatty acid moiety, e.g., beta-myristic acid.

As used herein, the term "beta-hydroxy fatty acid" refers to a fatty acid chain comprising a hydroxy group at the beta position of the fatty acid chain. As is understood by those skilled in the art, the beta position corresponds to the third carbon of the fatty acid chain, the first carbon being the carbon of the carboxylate group. Thus, when used in reference to an acyl amino acid of the present disclosure, where the carboxylate moiety of the fatty acid has been covalently attached to the nitrogen of the amino acid, the beta position corresponds to the carbon two carbons removed from the carbon having the ester group. A beta-hydroxy fatty acid to be used in accordance with the present disclosure may contain any number of carbon atoms in the fatty acid chain. As non-limiting examples, a beta-hydroxy fatty acid may contain 3, 4, 5, 6, 7, 8.9, 10, 11, 12, 3, 14, 15, 15, 16, 17, 18, 19, 20 or more carbon atoms. Beta-hydroxy fatty acids to be used in accordance with the present disclosure may contain linear carbon chains, in which each carbon of the chain, with the exception of the terminal carbon atom and the carbon attached to the nitrogen of the amino acid, is directly covalently linked to two other carbon atoms. Additionally or alternatively, beta-hydroxy fatty acids to be used in accordance with the present disclosure may contain branched carbon chains, in which at least one carbon of the chain is directly covalently linked to three or more other carbon atoms. Beta-hydroxy fatty acids to be used in accordance with the present disclosure may contain one or more double bonds between adjacent carbon atoms. Alternatively, beta-hydroxy fatty acids to be used in accordance with the present disclosure may contain only single-bonds between adjacent carbon atoms. A non-limiting exemplary beta-hydroxy fatty acid that may be used in accordance with the present disclosure is beta-hydroxy myristic acid, which contains 13 to 15 carbons in the fatty acid chain. Those of ordinary skill in the art will be aware of various beta-hydroxy fatty acids that can be used in accordance with the present disclosure. Different beta-hydroxy fatty acid linkage domains that exhibit specificity for other beta-hydroxy fatty acids (e.g., naturally or non-naturally occurring beta-hydroxy fatty acids) may be used in accordance with the present disclosure to generate any acyl amino acid of the practitioner's choosing.

As used herein, the term "covalently linked" refers to its ordinary meaning in the art, and unless otherwise specified, encompasses both direct and indirect linkages.

As used herein, the terms "domain" and "polypeptide domain" generally refer to polypeptide moieties that naturally occur in longer polypeptides, or to engineered polypeptide moieties that are homologous to such naturally occurring polypeptide moieties, which polypeptide moieties have a characteristic structure (e.g., primary structure such as the amino acid sequence of the domain, although characteristic structure of a given domain also encompasses secondary, tertiary, quaternary, etc. structures) and exhibit one or more distinct functions. As will be understood by those skilled in the art, in many cases, polypeptides are modular and are comprised of one or more polypeptide domains, each domain exhibiting one or more distinct functions that contribute to the overall function of the polypeptide. The structure and function of many such domains are known to those skilled in the art. For example, Fields and Song (Nature, 340(6230): 245-6, 1989) showed that transcription factors are comprised of at least two polypeptide domains: a DNA binding domain and a transcriptional activation domain, each of which contributes to the overall function of the transcription factor to initiate or enhance transcription of a particular gene that is under control of a particular promoter sequence. A polypeptide domain, as the term is used herein, also refers an engineered polypeptide that is homologous to a naturally occurring polypeptide domain. "Homologous", as the term is used herein, refers to the characteristic of being similar at the nucleotide or amino acid level to a reference nucleotide or polypeptide. For example, a polypeptide domain that has been altered at one or more positions such that the amino acids of the reference polypeptide have been substituted with amino acids exhibiting similar biochemical characteristics (e.g., hydrophobicity, charge, bulkiness) will generally be homologous to the reference polypeptide. Percent identity and similarity at the nucleotide or amino acid level are often useful measures of whether a given nucleotide or polypeptide is homologous to a reference nucleotide or amino acid. Those skilled in the art will understand the concept of homology and will be able to determine whether a given nucleotide or amino acid sequence is homologous to a reference nucleotide or amino acid sequence.

As used herein, the term "engineered" refers to a non-naturally occurring moiety that has been created by the hand of man. For example, in reference to a polypeptide, an "engineered polypeptide" refers to a polypeptide that has been designed and/or manipulated to comprise a polypeptide that does not exist in nature. In various embodiments, an engineered polypeptide comprises two or more covalently linked polypeptide domains. Typically such domains will be linked via peptide bonds, although the present disclosure is not limited to engineered polypeptides comprising polypeptide domains linked via peptide bonds, and encompasses other covalent linkages known to those skilled in the art. One or more covalently linked polypeptide domains of engineered polypeptides may be naturally occurring. Thus, in certain embodiments, engineered polypeptides of the present disclosure comprise two or more covalently linked domains, at least one of which is naturally occurring. In certain embodiments, two or more naturally occurring polypeptide domains are covalently linked to generate an engineered polypeptide. For example, naturally occurring polypeptide domains from two or more different polypeptides may be covalently linked to generate an engineered polypeptide. In certain embodiments, naturally occurring polypeptide domains of an engineered polypeptide are covalently linked in nature, but are covalently linked in the engineered polypeptide in a way that is different from the way the domains are linked nature. For example, two polypeptide domains that naturally occur in the same polypeptide but which are separated by one or more intervening amino acid residues may be directly covalently linked (e.g., by removing the intervening amino acid residues) to generate an engineered polypeptide of the present disclosure. Additionally or alternatively, two polypeptide domains that naturally occur in the same polypeptide which are directly covalently linked together (e.g., not separated by one or more intervening amino acid residues) may be indirectly covalently linked (e.g., by inserting one or more intervening amino acid residues) to generate an engineered polypeptide of the present disclosure. In certain embodiments, one or more covalently linked polypeptide domains of an engineered polypeptide may not exist naturally. For example, such polypeptide domains may be engineered themselves.

As used herein, the term "fatty acid linkage domain" refers to a polypeptide domain that covalently links a fatty acid to an amino acid to form an acyl amino acid. In certain embodiments, a fatty acid linkage domain is covalently linked to one or more subdomains of a peptide synthetase domain to generate an engineered polypeptide useful in the synthesis of an acyl amino acid. A variety of fatty acids are known to those of ordinary skill in the art, as are a variety of fatty acid linkage domains, such as for example, fatty acid linkage domains present in various peptide synthetase complexes that produce lipopeptides. In certain embodiments, a fatty acid linkage domain of the present disclosure comprises a beta-hydroxy fatty acid linkage domain.

As used herein, the term "identity," refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 6%, at least 70%, at least 80%, at least 90%, at least 95%, or substantially 100% of the length of a reference sequence. The nucleotides or amino acid residues at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

As used herein, the term "isolated" refers to a substance and/or entity that has been (I) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

As used herein, the term "naturally occurring", as used herein when referring to an amino acid, refers to one of the standard group of twenty amino acids that are the building blocks of polypeptides of most organisms, including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain embodiments, the term "naturally occurring" also refers to amino acids that are used less frequently and are typically not included in this standard group of twenty but are nevertheless still used by one or more organisms and incorporated into certain polypeptides. For example, the codons UAG and UGA normally encode stop codons in most organisms. However, in some organisms the codons UAG and UGA encode the amino acids selenocysteine and pyrrolysine. Thus, in certain embodiments, selenocysteine and pyrrolysine are naturally occurring amino acids. The term "naturally occurring", as used herein when referring to a polypeptide or polypeptide domain, refers to a polypeptide or polypeptide domain that occurs in one or more organisms. In certain embodiments, engineered polypeptides of the present disclosure comprise one or more naturally occurring polypeptide domains that naturally exist in different polypeptides. In certain embodiments, engineered polypeptides of the present disclosure comprise two or more naturally occurring polypeptide domains that are covalently linked (directly or indirectly) in the polypeptide in which they occur, but are linked in the engineered polypeptide in a non-natural manner. As a non-limiting example, two naturally occurring polypeptide domains that are directly covalently linked may be separated in the engineered polypeptide by one or more intervening amino acid residues. Additionally or alternatively, two naturally occurring polypeptide domains that are indirectly covalently linked may be directly covalently linked in the engineered polypeptide, e.g. by removing one or more intervening amino acid residues. Such engineered polypeptides are not naturally occurring, as the term is used herein.

As used herein, the term "operably linked" refers to a relationship between two nucleic acid sequences wherein the expression of one of the nucleic acid sequences is controlled by, regulated by or modulated by the other nucleic acid sequence. In some embodiments, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species.

As used herein, the term "peptide synthetase domain" refers to a polypeptide domain that typically comprises three domains: an adenylation (A) domain, responsible for selectively recognizing and activating a specific amino acid, a thiolation (T) domain, which tethers the activated amino acid to a cofactor via thioester linkage, and condensation (C) domain, which links amino acids joined to successive units of the peptide synthetase by the formation of amide bonds. A peptide synthetase domain typically recognizes and activates a single, specific amino acid, and in the situation where the peptide synthetase domain is not the first domain in the pathway, links the specific amino acid to a growing peptide chain. In certain embodiments, a peptide synthetase domain is covalently linked to a fatty acid linkage domain such as a beta-hydroxy fatty acid linkage domain, which construct may be advantageously used to generate an acyl amino acid. In certain embodiments, the peptide synthetase domain comprises fewer than the three typical domains. For example, a peptide synthetase domain in accordance with certain methods and compositions of the disclosure may include the adenylation and thiolation domains covalently linked to each other, but may lack a condensation domain. In certain engineered polypeptides of the disclosure, for example, the condensation domain of the peptide synthetase is not present, and/or a different domain (e.g., a fatty acid linkage domain) is covalently linked to the adenylation and thiolation domains. In certain embodiments, a peptide synthetase domain is also covalently linked to a reductase domain that acts on the acyl amino acid so produced, as described herein. A variety of peptide synthetase domains are known to those skilled in the art, e.g. such as those present in a variety of nonribosomal peptide synthetase complexes. Those skilled in the art will be aware of methods to determine whether a give polypeptide domain is a peptide synthetase domain. Different peptide synthetase domains often exhibit specificity for one or more amino acids. As one non-limiting example, the last peptide synthetase domain from the gramicidin peptide synthetase is specific for glycine. Thus, the last peptide synthetase domain from gramicidin peptide synthetase can be used in methods known in the art (e.g., as described in U.S. Pat. No. 7,981,685) to construct an engineered polypeptide useful in the generation of an acyl amino acid that comprises a glycine moiety, which, in accordance with certain methods of the present disclosure, can be treated with one or more reductase polypeptides so that acyl ethanolamine (FA-ethanolamine), a non-ionic surfactant is released. Different peptide synthetase domains that exhibit specificity for other amino acids (e.g., naturally or non-naturally occurring amino acids) may be used in accordance with methods known in the art to generate any acyl amino acid, which acyl amino acid can then be treated in accordance with methods of the disclosure to generate any of a variety of acyl alcohols of the practitioner's choosing.

As used herein, the term "polypeptide" refers to a series of amino acids joined together in peptide linkages, such as polypeptides synthesized by ribosomal machinery in naturally occurring organisms. The term "polypeptide" also refers to a series of amino acids joined together by non-ribosomal machinery, such as by way of non-limiting example, polypeptides synthesized by various peptide synthetases, including both naturally occurring and engineered peptide synthetases. Such non-ribosomally produced polypeptides exhibit a greater diversity in covalent linkages than polypeptides synthesized by ribosomes (although those skilled in the art will understand that the amino acids of ribosomally-produced polypeptides may also be linked by covalent bonds that are not peptide bonds, such as the linkage of cysteines via di-sulfide bonds). For example, surfactin is a lipopeptide synthesized by the surfactin synthetase complex (a schematic of which is depicted in FIG. 2). Surfactin comprises seven amino acids, which are initially joined by peptide bonds, as well as a beta-hydroxy fatty acid covalently linked to the first amino acid, glutamate. However, upon addition the final amino acid (leucine), the polypeptide is released and the thioesterase domain of the SRFC protein catalyzes the release of the product via a nucleophilic attack of the beta-hydroxy of the fatty acid on the carbonyl of the C-terminal Leu of the peptide, cyclizing the molecule via formation of an ester, resulting in the C-terminus carboxyl group of leucine attached via a lactone bond to the b-hydroxyl group of the fatty acid. Polypeptides can be two or more amino acids in length, although most polypeptides produced by ribosomes and peptide synthetases are longer than two amino acids. For example, polypeptides may be 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 or more amino acids in length.

As used herein, the term "reductase polypeptide" refers to any polypeptide that 1) catalyzes reduction of an amino acid, or reduction product of an amino acid (e.g., an amino aldehyde) attached by a peptide synthetase complex and/or 2) releases a product of the peptide synthetase complex with the terminal residue as a reduction product of an amino acid (e.g., an amino aldehyde or an alcohol such as an amino alcohol) from the peptide synthetase complex. In certain embodiments, a reductase polypeptide is a polypeptide domain that is covalently linked to one or more other domains, e.g., it is a "reductase domain" within a larger polypeptide comprising more than one polypeptide domain. In some embodiments, the reductase polypeptide and the one or more other domains to which it is covalently linked form an engineered polypeptide. For example, in some embodiments, the reductase polypeptide is a reductase domain that is covalently linked to one or more subdomains of a peptide synthetase domain and a fatty acid linkage domain such as a beta-hydroxy fatty acid linkage domain to generate an engineered polypeptide useful in the synthesis of an acyl alcohol, e.g., an acyl amino alcohol. Accordingly, in some embodiments, a reductase polypeptide catalyzes reduction of an acyl amino acid, or a reduction product thereof, and/or release a reduction product of an acyl amino acid (e.g., an acyl amino aldehyde or an acyl alcohol, e.g., acyl amino alcohol.) A variety of reductase domains are found in nonribosomal peptide synthetase complexes from a variety of species. A non-limiting example of a reductase domain that may be used in accordance with the present disclosure includes the reductase domain from linear gramicidin (ATCC8185). However, any reductase polypeptide that at least partially reduces an acyl amino acid produced by a peptide synthetase complex and/or releases a reduced acyl amino acid from the peptide synthetase complex may be used in accordance with the present disclosure. In some embodiments, reductase polypeptides and reductase domains are characterized by the presence of the consensus sequence: [LIVSPADNK]-x(9)-{P}-x(2)-Y-[PSTAGNCV]-

[STAGNQCIVM]-[STAGC]-K-{PC}-[SAGFYR]-[LIVM-STAGD]-x{K}-[LIVMFYW]-{D}-x-{YR}-[LIVMFYW-GAPTHQ]-[GSACQRHM](SEQ ID NO. 1), where square brackets ("[ ]") indicate amino acids that are typically present at that position, squiggly brackets ("{ }") indicate amino acids that amino acids that are typically not present at that position, and "x" denotes any amino acid or a gap. X(9) for example denotes any amino acids or gaps for nine consecutive positions. Those skilled in the art will be aware of methods to determine whether a give polypeptide domain is a reductase domain. Reductase polypeptides compatible for use in presently disclosed methods include reductase polypeptides with substantially the same sequence as a reductase polypeptide found in nature as well as reductase polypeptides whose sequences are not found in nature. For example, some reductase polypeptides suitable for use with certain of the presently disclosed methods are engineered to have one or more mutations relative to a sequence of a naturally occurring reductase polypeptides.

DETAILED DESCRIPTION OF CERTAIN EMBODIMENTS

The present disclosure provides, in various aspects, methods of generating acyl alcohols, methods of generating free fatty acids, free amino acids, and/or free alcohols from acyl amino acids and/or acyl alcohols, and related compositions and cells therefore.

Methods of Generating Acyl Alcohols

In one aspect, provided are methods comprising steps of providing an acyl amino acid and treating the acyl amino acid with a reductase polypeptide so that an acyl alcohol is released.

In some embodiments, the steps of providing and treating are performed in a cell expressing one or more reductase polypeptides that act on the acyl amino acid. In some embodiments, the acyl amino acid is generated in the cell.

In some embodiments, the cell expresses one or more engineered polypeptides, as described further herein.

In some embodiments, the acyl alcohol is a non-ionic surfactant.

Uses

In certain embodiments, compositions and methods of the present disclosure are useful in large-scale production of acyl alcohols in certain embodiments, acyl alcohols are produced in commercially viable quantities using compositions and methods of the present disclosure. For example, engineered polypeptides of the present disclosure may be used to produce acyl alcohols to a level of at least 5, 6, 7, 8, 9, 10, 11, 12, 13, 14, 15, 16, 17, 18, 19, 20, 30, 40, 50, 60, 70, 80, 90, 100, 110, 120, 130, 140, 150, 150, 200, 250, 300, 400, 500, 600, 700, 800, 900, 1000 mg/L or higher. Biological production of acyl alcohols using engineered polypeptides of the present disclosure achieves certain advantages over other methods of producing acyl alcohols. For example, as compared to chemical production methods, production of acyl alcohols using compositions and methods of the present disclosure utilizes more readily available and starting materials that are easier to store, reduces the necessity of using harsh and sometimes dangerous chemical reagents in the manufacturing process, reduces the difficulty and efficiency of the synthesis itself by utilizing host cells as bioreactors, and reduces the fiscal and environmental cost of disposing of chemical by-products. For example, no oil is needed to produce acyl alcohols according to methods of the present disclosure.

As a non-limiting example, using certain methods of the present disclosure, fatty acids can be linked to ethanolamine, producing an acyl ethanolamine that is a non-ionic surfactant and is similar to cocamide monoethanolamine (MEA). In some embodiments, such an acyl alcohol is produced by generating an acyl amino acid from engineered polypeptide comprising fatty acid linkage domain that is covalently linked to an adenylation domain specific for glycine (e.g., an adenylation domain from or derived from a peptide synthetase domain specific for glycine) and a thiolation domain. The acyl glycine that is produced is then acted upon by one or more reductase polypeptides that may or may not be covalently liked to the fatty acid linkage, adenylation, and thiolation domains, such that a fatty acid-ethanolamine is released from the engineered polypeptide.

As another non-limiting example, fatty acids can be linked to serinol (i.e., 2-amino–1-3-propanediol), producing chemical products similar to cocamide diethanolamine (DEA) In some embodiments, such an acyl alcohol is produced by generating an acyl amino acid from engineered polypeptide comprising fatty acid linkage domain that is covalently linked to an adenylation domain specific for serine (e.g., an adenylation domain from or derived from a peptide synthetase domain specific for serine) and a thiolation domain. The acyl serine that is produced is then acted upon by one or more reductase polypeptides that may or may not be covalently liked to the fatty acid linkage, adenylation, and thiolation domains, such that a fatty acid-serinol is released from the engineered polypeptide.

Methods of Cleaving Acyl Alcohols

In one aspect, provided are methods comprising steps of providing an acyl amino acid or acyl alcohol and treating the acyl amino acid or acyl alcohol so that free fatty acid and tree amino acid or free alcohol is released.

In certain embodiments, the treating step comprises incubating the acyl amino acid or acyl alcohol in acid for a period of time. For example, in some embodiments, the acyl amino acid or acyl alcohol is incubated in acid for at least 30 minutes. In some embodiments, the acyl amino acid or acyl alcohol is incubated for at least 1, at least 2, at least 4, at least 6, at least 8, at least 10, at least 12, at least 14, at least 16, at least 18, at least 20, at least 22, at least 24, at least 30, at least 36, at least 42, or at least 48 hours. In some embodiments, the acyl amino acid or acyl alcohol is incubated in acid for at least or approximately 12 hours. In some embodiments, the acyl amino acid or acyl alcohol is incubated in acid for at least or approximately 24 hours. In some embodiments, the acyl amino acid or acyl alcohol is incubated in acid for at least or approximately 36 hours. In some embodiments, the acyl amino acid or acyl alcohol is incubated in acid for at least or approximately 48 hours.

In some embodiments, the acyl amino acid or acyl alcohol is incubated in acid in the presence of heat, i.e., such that the incubation temperature is higher than that of room temperature (typically at or around 20° C. to at or around 26° C.), for at least a portion of the total acid incubation time. For example, in some embodiments, the acyl amino acid or acyl alcohol is incubated at a temperature of at least 30° C., at least 35° C., at least 40° C., at least 45° C., at least 50° C., at least 55° C., at least 60° C., at least 65° C., at least 70° C., at least 75° C. at least 80° C., at least 85° C., at least 90° C., at least 95° C., at least 100° C., at least 110° C., at least 120°

C., at least 130° C., at least 140° C., at least 150° C., at least 160° C., at least 170° C., at least 180° C., at least 190° C., or at least 200° C. In some embodiments, the acyl amino acid or acyl alcohol is incubated at a temperature of at least or approximately 80° C. In some embodiments, the acyl amino acid or acyl alcohol is incubated at a temperature of at least or approximately 100° C.

The concentration of the acid used may vary depending on the embodiment. In some embodiments, the concentration depends on factors such as any or any combination of the type of acid used, the period of incubation, and the temperature.

In some embodiments, the acid is hydrochloric acid. In some embodiments, the hydrochloric acid is used at a concentration of at least 2 N, at least 2.5 N, at least 3 N, at least 3.5 N, at least 4 N, at least 4.5 N, at least 5 N, at least 5.5 N, at least 6 N, at least 7 N, at least 8 N, at least 9 N, or at least 10 N. In some embodiments, the hydrochloric acid is used at a concentration of at least or approximately 6 N.

In certain embodiments, the treating step comprises incubating the acyl amino acid or acyl alcohol with an enzyme for a period of time. Generally, such an enzyme is capable of cleaving the amide bond within an acyl amino acid or acid alcohol. Examples of such enzymes include, but are not limited to, acylases, many types of which are commercially available. (See also, e.g., Otvos et al, "Investigation on the mechanism of acylase-1-catalyzed acyl amino acid hydrolysis," Biochem Bipophys Res Commun 44(5):1056-1064, 1971, the entire contents of which are incorporated by reference herein.)

In certain embodiments, the treating step comprises incubating the acyl amino acid or acyl alcohol at an elevated pressure (above that of atmosphere) for a period of time. For example, the acyl amino acid or acyl alcohol can be incubating at a pressure of at least or approximately 100 kPa (15 psi). In some embodiments, the acyl amino acid or acyl alcohol is incubated in a vacuum. In some embodiments, the acyl amino acid or acyl alcohol can be incubated at both an elevated pressure and an elevated temperature (optionally also in a vacuum), e.g., as in an autoclave. (See, e.g., Badadani et al., Optimum conditions for autoclaving for hydrolysis of proteins and urinary peptides of prolyl and hydroxyprolyl residues and HPLC analysis," *J Chromatogra B Analyt Technical Biomed Life Sci* 847(2):267-274, 2006, the entire contents of which are incorporated by reference herein.)

Any suitable combination of the above-mentioned treating steps can also be used, either sequentially or concurrently.

In certain embodiments, only an acyl amino acid, or a mixture of acyl amino acids having the same amino acid moiety and the same fatty acid moiety (which can be of variable length), is provided. That is, in such embodiments, no acyl alcohol is provided. In some embodiments, products of cleavage would include free fatty acids and free amino acids.

In certain embodiments, only an acyl alcohol, or a mixture of acyl alcohols having the same alcohol moiety and the same fatty acid moiety (which can be of variable length), is provided. That is, in such embodiments, no acyl amino acid is provided. In some embodiments, products of cleavage would include free fatty acids and free alcohols.

In certain embodiments, a mixture of acyl amino acids and acyl alcohols is provided. In some embodiments, products of cleavage would include free fatty acids, free amino acids, and free alcohols.

In some embodiments, the free fatty acid is myristic acid.

In certain embodiments, provided methods further comprise a step of separating at least one cleavage product from other cleavage products. In some embodiments, provided methods further comprise a step of separating free fatty acids from other cleavage product(s). In some embodiments, provided methods further comprise a step of separating free amino acids from other cleavage product(s). In some embodiments, provided methods further comprise a step of separating free alcohols from other cleavage product(s). In some embodiments, a single step of separating allows the simultaneous recovery of more than one cleavage product. For example, phase separation can be used to separate free fatty acids from free amino acids and/or free alcohols, as fatty acid is not highly soluble in water and forms a separate layer distinct from the aqueous layer.

In certain embodiments, provided methods further comprise a step of treating the fatty acid so as to reduce the oxygen content of the free fatty acid, e.g., by hydrotreatment. (See, e.g., Marinangeli et al., "Opportunities for biorenewables in oil refineries," Submitted to U.S. Department of Energy 1-43, 2005, the entire contents of which are incorporated by reference herein.)

In certain embodiments, provided methods further comprise a step of purifying one or more cleavage products (i.e., free fatty acid, free amino acids, and/or free alcohols) from residual components Uses Cleavage products generated by methods of the present disclosure may have commercial value. For example, purified amino acids can be sold for use in feed or food applications. For example, free fatty acids can be incorporated into personal care products, cosmetics, food, or feed. Alternatively or additionally, free fatty acids can be sold for use in diesel fuel. For example, after hydrotreatment to reduce the oxygen content of free fatty acids, a free fatty acid such as myristic acid will be converted to tetradecane and tridecane. These hydrocarbons have a molecular weight ideal for use as diesel fuel. Alkanes in diesel fuel typically range in size from ten to twenty-five carbons, with main components having a size between 13 to 17 carbons. (See, e.g., Liang et al., "The organic composition of diesel particulate matter, diesel fuel and engine oil of a non-road diesel generator,"*J Environ Monit* 7:983-988, 2005, the entire contents of which are incorporated by reference herein.)

Alternatively or additionally, hydrocarbons obtained from cleavage products generated by methods of the present disclosure can be used as gasoline. Particular peptide synthetase systems that link fatty acids to amino acids have particular preferences in terms of the length of the fatty acid used in the reaction. Certain peptide synthetase enzymes synthesize acyl peptides in which the fatty acid is methylated at one or more positions. Methylated hydrocarbons composed of 4 to 12 carbons are preferred hydrocarbons for use as gasoline (e.g., 2,2,4-trimethylpentane), and are known to have a higher "octane rating" than straight-chain hydrocarbons of similar molecular weight. (See, e.g., Balaban et al., structure-property analysis of octane numbers for hydrocarbons (alkanes, cycloalkanes, alkenes)," MATCH Commun Math Comput Chem 28:13-27, 1992.) The octane rating is as measure of the capacity of gasoline fuel to burn effectively when intentionally ignited (for example, via ignition due to spark from a spark plug in an automobile) and not to explode prematurely when compressed (in the absence of an intentionally created spark). Explosion in the absence of a spark causes engine "knocking", is associated with low octane fuels, and should be avoided. (See, e.g., Perdih et al., "Chemical interpretation of octane number," Acta Chim Slov 53:306-315, 2006.) The Blending Octane Number (BON) is a measure of the octane number of a single component when blended with other components. (See, e.g., Leffler, "Petroleum refining in nontechnical language, fourth edition," Copyright, Penn Well Corporation. Tulas, Okla., 2008.). Use of a peptide synthetase enzyme to link a terminally branched fatty acid such as 4-methyl pentanoic acid to an amino acid or amino alcohol will generate a fermentation product that can be cleaved, by methods as described above, to produce free 4-methyl pentanoic acid. Hydrotreatment of 4-methyl pentanoic acid will generate a mix of 2-methyl pentane (isohexane) and 2-methyl butane (isopentane). Isohexane and isopentane have Blending Octane Numbers (BON) of 99 and 83, respectively. Hydrotreatment would be expected to generate approximately a 50-50 mix of these species, and a 50-50 mix of these species will have an octane rating of about 91 (the average of 99 and 83), which is identical to the octane rating of premium gasoline (91 octane). (See, e.g., Ibsen et al., "Review of market for octane enhancers," Final Report for NREL prepared under subcontract No. TXE-0-29113-01, 1-54, 2000.).

Thus, in some embodiments, certain methods of the present disclosure here can be used to produce hydrocarbons that can be using as gasoline.

Acyl Alcohols

Acyl alcohols generally comprise a fatty acid moiety covalently and directly linked to an alcohol moiety. In some embodiments, acyl alcohols are acyl amino alcohols, e.g., a fatty acid moiety covalently and directly linked to an amino alcohol moiety.

Any of a variety of acyl alcohols may be generated by compositions and methods of the present disclosure or provided in certain methods of the present disclosure. By employing specific peptide synthetase domains, fatty acid linkage domains, and reductase domains in one or more engineered polypeptides, one skilled in the art will be able to generate a specific acyl alcohol following the teachings of the present disclosure.

In certain embodiments, acyl alcohols generated by compositions and methods of the present disclosure are released, by treating with a reductase polypeptide, an acyl amino acid comprising an amino acid selected from one of the twenty amino acids commonly employed in ribosomal peptide synthesis, i.e., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and/or valine. In certain embodiments, acyl alcohols are released, by treating (with one or more reductase polypeptides) an acyl amino acid comprising an amino acid other than the aforementioned twenty, for example, amino acids used less commonly during ribosomal polypeptide synthesis such as, without limitation, selenocysteine and/or pyrrolysine. In certain embodiments, acyl alcohols are released from acyl amino acids that comprise amino acids that are not used during ribosomal polypeptide synthesis such as, without limitation, norleucine, beta-alanine and/or ornithine, and/or D-amino acids.

In certain embodiments, acyl alcohols generated by certain compositions and methods of the present disclosure, or provided in certain methods of the present disclosure, comprise a fatty acid moiety. A fatty acid of acyl alcohols of the present disclosure may be any of a variety of fatty acids known to those of ordinary skill in the art. For example, acyl alcohols of the present disclosure may comprise saturated fatty acids such as, without limitation, butyric acid, caproic acid, caprylic acid, capric acid, lauric acid, myristic acid, palmitic acid, stearic arachidic acid, behenic acid, and/or lignoceric acid. In certain embodiments, acyl alcohols of the present disclosure may comprise unsaturated fatty acids such as, without limitation, myristoleic acid, palmitoleic acid, oliec acid, linoleic acid, alpha-linolenic acid, arachidonic acid, eicosapentaenoic acid, erucic acid, and/or docosahexaenoic acid. Other saturated and unsaturated fatty acids that may be used in accordance with the present disclosure will be known to those of ordinary skill in the art. In certain embodiments, acyl alcohols produced by compositions and methods of the present disclosure comprise beta-hydroxy fatty acids as the fatty acid moiety. As is understood by those of ordinary skill in the art, beta-hydroxy fatty acids comprise a hydroxy group attached to the third carbon of the fatty acid chain, the first carbon being the carbon of the carboxylate group.

In some embodiments, the acyl amino alcohol is a reduction product of an acyl amino acid that comprises a naturally occurring amino acid (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) moiety.

In some embodiments, the acyl amino alcohol is acyl ethanolamine ("FA-ethanolamine), e.g., beta-hydroxyl myristoyl monoethanolamitie (MEA), the structure of which is shown in FIG. 1. As can be seen in FIG. 1, beta-hydroxyl myristoyl MEA is similar in structure to cocamide MEA, a commercially widely used nonionic surfactant.

In some embodiments, the acyl amino alcohol is acyl serinol. In some embodiments, the acyl amino alcohol is acyl alaninol.

In some embodiments, the acyl amino alcohol is a reduction product of an acyl amino acid that comprises a non-naturally occurring amino acid moiety.

Peptide Synthetase Complexes

Peptide synthetase complexes are multienzymatic complexes found in both prokaryotes and eukarvotes comprising one or more enzymatic subunits that catalyze the non-ribosomal production of a variety of peptides (see, for example, Kleinkauf et al., Annu. Rev. Microbiol. 41:259-289, 1987; see also U.S. Pat. Nos. 5,652,116 and 5,795,738). Non-ribosomal synthesis is also known as thiotemplate synthesis (see e.g., Kleinkauf et al.). Peptide synthetase complexes typically include one or more peptide synthetase domains that recognize specific amino acids and are responsible for catalyzing addition of the amino acid to the polypeptide chain.

The catalytic steps in the addition of amino acids include: recognition of an amino acid by the peptide synthetase domain, activation of the amino acid (formation of an amino-acyladenylate), binding of the activated amino acid to the enzyme via a thioester bond between the carboxylic group of the amino acid and an SH group of an enzymatic co-factor, which cofactor is itself bound to the enzyme inside each peptide synthetase domain, and formation of the peptide bonds among the amino acids. A peptide synthetase domain comprises subdomains that carry out specific roles in these steps to form the peptide product. One subdomain, the adenylation (A) domain, is responsible for selectively recognizing and activating the amino acid that is to be incorporated by a particular unit of the peptide synthetase. The activated amino acid is joined to the peptide synthetase through the enzymatic action of another subdomain, the thiolation (T) domain, that is generally located adjacent to the A domain. Amino acids joined to successive units of the peptide synthetase are subsequently linked together by the formation of amide bonds catalyzed by another subdomain, the condensation (C) domain.

Peptide synthetase domains that catalyze the addition of D-amino acids also have the ability to catalyze the racemization of L-amino acids to D-amino acids. Peptide synthetase complexes also typically include a conserved thioesterase domain that terminates the growing amino acid chain and releases the product, or a reductase domain that terminates the growing amino acid chain, reduces the terminal amino acid, and releases the product. However, in accordance with certain embodiments of the present disclosure, peptide synthetase domains only contain certain of their typical subdomains, e.g., in some embodiments, peptide synthetase domains used in accordance with the present disclosure lack thioesterase domains.

The genes that encode peptide synthetase complexes have a modular structure that parallels the functional domain structure of the complexes (see, for example, Cosmina et al., Mol. Microbiol. 8:821, 1993; Kratzxchmar et al., J. Bacteriol. 171:5422, 1989; Weckermann et al., Nuc. Acids res. 16:11841, 1988; Smith et al., EMBO J. 9:741, 1990; Smith et al., EMBO J. 9:2743, 1990; MacCabe et al., J Biol. Chem. 266:12646, 1991; Coque et al., Mol. Microbiol. 5:1125, 1991; Diez et al., J. Biol. Chem. 265:16358, 1990).

Hundreds of peptides are known to be produced by peptide synthetase complexes. Such nonribosomally-produced peptides often have non-linear structures, including cyclic structures exemplified by the peptides surfactin, cyclosporin, tyrocidin, and mycobacillin, or branched cyclic structures exemplified by the peptides polymyxin and bacitracin. Moreover, such nonribosomally-produced peptides may contain amino acids not usually present in ribosomally-produced polypeptides such as for example norleucine, beta-alanine and/or ornithine, as well as D-amino acids. Additionally or alternatively, such nonribosomally-produced peptides may comprise one or more non-peptide moieties that are covalently linked to the peptide. As one non-limiting example, surfactin is a cyclic lipopeptide that comprises a beta-hydroxy fatty acid covalently linked to the first glutamate of the lipopeptide. Other non-peptide moieties that are covalently linked to peptides produced by peptide synthetase complexes are known to those skilled in the art, including for example sugars, chlorine or other halogen groups, N-methyl and N-formyl groups, glycosyl groups, acetyl groups, etc.

Typically, each amino acid of the non ribosomally-produced peptide is specified by a distinct peptide synthetase domain. For example, the surfactin synthetase complex which catalyzes the polymerization of the lipopeptide surfactin consists of three enzymatic subunits. The first two subunits each comprise three peptide synthetase domains, whereas the third has only one. These seven peptide synthetase domains are responsible for the recognition, activation, binding and polymerization of L-Glu, L-Leu, D-Leu, L-Val, L-Asp, D-Leu and L-Leu, the amino acids present in surfactin. (See FIG. 2 for schematic of the surfactin synthetase complex.)

A similar organization in discrete, repeated peptide synthetase domains occurs in various peptide synthetase genes in a variety of species, including bacteria and fungi, for example srfA (Cosmina et al., Mol. Microbiol. 8, 821-831, 1993), grsA and grsB (Kratzxchmar et al., J. Bacterial. 171, 5422-5429, 1989) tycA and tycB (Weckermann et al., Nucl. Acid. Res. 16, 11841-11843, 1988) and ACV from various fungal species (Smith et al., EMBO J. 9, 741-747, 1990; Smith et al., EMBO J. 9, 2743-2750, 1990; MacCabe et al., J. Biol. Chem. 266, 12646-12654, 1991; Coque et al., Mol. Microbiol. 5, 1125-1133, 1991; Diez et al., J. Biol. Chem. 265, 16358-16365, 1990). The peptide synthetase domains of even distant species contain sequence regions with high homology, some of which are conserved and specific for all the peptide synthetases. Additionally, certain sequence regions within peptide synthetase domains are even more highly conserved among peptide synthetase domains which recognize the same amino acid (Cosmina et al., Mol. Microbiol. 8, 821-831, 1992).

Engineered Polypeptides Useful in the Generation of Acyl Alcohols

In one aspect, provided are compositions and methods for the generation of acyl alcohols. In certain embodiments, compositions of the present disclosure comprise engineered polypeptides that are useful in the production of acyl alcohols. In certain embodiments, engineered polypeptides of the present disclosure comprise a peptide synthetase domain covalently linked to a fatty acid linkage domain. In some embodiments, engineered polypeptides further comprise one or more reductase domains covalently linked to the fatty acid linkage domain and the peptide synthetase domain. In certain embodiments, the fatty acid linkage domain is a beta-hydroxy fatty acid linkage domain, for example, a beta-hydroxy myristic acid linkage domain.

In certain embodiments, one or more of a peptide synthetase domain, a fatty acid linkage domain (e.g., a beta-hydroxy fatty acid linkage domain), a reductase domain present in an engineered polypeptide of the present disclosure is naturally occurring, though their presence together on an engineered polypeptide, and/or their ordering, is typically not naturally occurring. Those of ordinary skill in the art will be aware of naturally occurring polypeptides that comprise one or more such domains, which domains can advantageously be used in accordance with the present disclosure. A non-limiting example of a naturally occurring polypeptide synthetase complex that comprises, for example, multiple peptide synthetase domains, a beta-hydroxy fatty acid linkage domain and a thioesterase domain includes surfactin synthetase. Engineered polypeptides of the present disclosure may comprise one or more of these domains that are naturally occurring in the surfactin synthetase complex.

As will be understood by those of ordinary skill in the art after reading this specification, it will typically be the fatty acid linkage domain of engineered polypeptides of the present disclosure that specify the identity of the fatty acid of the acyl amino acid. For example, the beta-hydroxy fatty acid linkage domain of the SRFA protein of the surfactin synthetase complex (described further, for example, in U.S. Pat. No. 7,981,685) recognizes and specifies beta-hydroxy myristic acid, the fatty acid present in surfactin. Thus, in certain embodiments, engineered polypeptides of the present disclosure comprise the beta-hydroxy fatty acid linkage domain of the SRFA protein of the surfactin synthetase complex, such that the acyl alcohol produced by the engineered polypeptide comprises beta-hydroxy myristic acid. The present disclosure encompasses the recognition that engineered polypeptides of the present disclosure may comprise other beta-hydroxy fatty acid linkage domains from other peptide synthetase complexes in order to generate other acyl alcohols.

In certain embodiments, engineered polypeptides of the present disclosure comprise an engineered fatty acid linkage domain (e.g. a beta-hydroxy fatty acid linkage domain) that is similar to a naturally occurring fatty acid linkage domain. For example, such engineered fatty acid linkage domains may comprise one or more amino acid insertions, deletions, substitutions, or transpositions as compared to a naturally occurring fatty acid linkage domain. Additionally or alternatively, such engineered fatty acid linkage domains may exhibit homology to a naturally occurring fatty acid linkage domain, as measured by, for example, percent identity or similarity at the amino acid level, for example, at least 70%, at least 75%, at least 80%, at least 85%, at least 90%, or at least 95%, or at least 98% identity at the amino acid level. Additionally or alternatively, such engineered fatty acid linkage domains may comprise one or more amino acid sequences that conform to a consensus sequence characteristic of a given naturally occurring fatty acid linkage domain. In certain embodiments, an engineered fatty acid linkage domain that is similar to a naturally occurring fatty acid linkage domain retains the fatty acid specificity of the naturally occurring fatty acid linkage domain. For example, the present disclosure encompasses the recognition that one or more amino acid changes may be made to the beta-hydroxy fatty acid linkage domain of the SRFA protein of the surfactin synthetase complex, such that the engineered beta-hydroxy fatty acid linkage domain still retains specificity for beta-hydroxy myristic acid. As will be recognized by those of ordinary skill in the art after reading this specification, engineered polypeptides containing such an engineered beta-hydroxy fatty acid linkage domain will be useful in the generation of acyl alcohols comprising beta-hydroxy myristic acid, such as, without limitation, beta-hydroxyl myristoyl MEA.

Engineered fatty acid linkage domains may exhibit one or more advantageous properties as compared to a naturally occurring fatty acid linkage domain. For example, engineered polypeptides comprising such engineered fatty acid linkage domains may yield an increased amount of the acyl alcohol, may be more stable in a given host cell, may be less toxic to a given host cell, etc. Those of ordinary skill in the art will understand various advantages of engineered fatty acid linkage domains of the present disclosure, and will be able to recognize and optimize such advantages in accordance with the teachings herein.

As will be understood by those of ordinary skill in the art after reading this specification, it will typically be the peptide synthetase domain of engineered polypeptides of the present disclosure that specifies the identity of the amino acid of the acyl amino acid. As one non-limiting example, the last peptide synthetase domain from the gramicidin peptide synthetase is specific for glycine. Thus, the last peptide synthetase domain from gramicidin peptide synthetase can be used in methods known in the art (e.g., as described in U.S. Pat. No. 7,981,685) to construct an engineered polypeptide useful in the generation of an acyl amino acid that comprises a glycine moiety, which, in accordance with certain methods of the present disclosure, can be treated with one or more reductase polypeptides so that acyl ethanolamine (FA-ethanolamine) is released. The present disclosure encompasses the recognition that engineered polypeptides of the present disclosure may comprise other peptide synthetase domains, e.g., other domains from gramicidin peptide synthetase, and/or other domains from other peptide synthetases, such as the surfactin synthetase complex in order to generate certain acyl alcohols. The various domains that are present in a given engineered polypeptide need not be derived from the same species.

In certain embodiments, engineered polypeptides of the present disclosure comprise an engineered peptide synthetase domain that is similar to a naturally occurring peptide synthetase domain. For example, such engineered peptide synthetase domains may comprise one or more amino acid insertions, deletions, substitutions, or transpositions as compared to a naturally occurring peptide synthetase domain. Additionally or alternatively, such engineered peptide synthetase domains may exhibit homology to a naturally occurring peptide synthetase domain, as measured by, for example, percent identity or similarity at the amino acid level, for example, at least 70%, at least 75%, at least 80%, at least 85%, at least 90%, or at least 95%, or at least 98% identity at the amino acid level. Additionally or alternatively, such engineered peptide synthetase domains may comprise one or more amino acid sequences that conform to a consensus sequence characteristic of a given naturally occurring peptide synthetase domain. In certain embodiments, an engineered peptide synthetase domain that is similar to a naturally occurring peptide synthetase domain retains the amino acid specificity of the naturally occurring peptide synthetase domain. For example, the present disclosure encompasses the recognition that one or more amino acid changes may be made to the last peptide synthetase domain of the gramicidin synthetase complex, such that the engineered peptide synthetase domain still retains specificity for glycine. As will be recognized by those of ordinary skill in the art after reading this specification, engineered polypeptides containing such an engineered peptide synthetase domain will be useful in the generation of acyl alcohols comprising ethanolamine such as, without limitation, beta-hydroxyl myristoyl monoethanolamine.

Such engineered peptide synthetase domains may exhibit one or more advantageous properties as compared to a naturally occurring peptide synthetase domain. For example, engineered polypeptides comprising such engineered peptide synthetase domains may yield an increased amount of the acyl alcohol, may be more stable in a given host cell, may be less toxic to a given host cell, etc. Those of ordinary skill in the art will understand various advantages of engineered peptide synthetase domains of the present disclosure, and will be able to recognize and optimize such advantages in accordance with the teachings herein.

Those of ordinary skill in the art will be aware of a variety of naturally occurring polypeptides that comprise a naturally occurring peptide synthetase domain, fatty acid linkage domain, thioesterase domain and/or reductase domain that may advantageously be incorporated into an engineered polypeptide of the present disclosure. For example, any of a variety of naturally occurring peptide synthetase complexes (see section herein entitled "Peptide Synthetase Complexes") may contain one or more of these domains, which domains may be incorporated into an engineered polypeptide of the present disclosure. Other non-limiting examples of peptide synthetase complexes include surfactin synthetase, fengycin synthetase, arthrofactin synthetase, lichenysin synthetase, syringomycin synthetase, syringopeptin synthetase, saframycin synthetase, gramicidin synthetase, cyclosporin synthetase, tyrocidin synthetase, mycobacillin synthetase, polymyxin synthetase and bacitracin synthetase.

In certain embodiments, one or more such domains present in an engineered polypeptide of the present disclosure is not naturally occurring, but is itself an engineered domain. For example, an engineered domain present in an engineered polypeptide of the present disclosure may comprise one or more amino acid insertions, deletions, substitutions or transpositions as compared to a naturally occurring peptide synthetase domain, fatty acid linkage domain (e.g. a beta-hydroxy fatty acid linkage domain), and/or reductase domain. In certain embodiments, an engineered peptide synthetase domain, fatty acid linkage domain (e.g. a beta-hydroxy fatty acid linkage domain), and/or reductase domain present in an engineered polypeptide of the present disclosure comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid insertions as compared to a naturally occurring domain. In certain embodiments, an engineered peptide synthetase domain, fatty acid linkage domain (e.g. a beta-hydroxy fatty acid linkage domain), and/or reductase domain present in an engineered polypeptide of the present disclosure comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid deletions as compared to a naturally occurring domain.

In certain embodiments, an engineered peptide synthetase domain, fatty acid linkage domain (e.g. a beta-hydroxy fatty acid linkage domain), and/or reductase domain present in an engineered polypeptide of the present disclosure comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid substitutions as compared to a naturally occurring domain. In certain embodiments, such amino acid substitutions result in an engineered domain that comprises an amino acid whose side chain contains a structurally similar side chain as compared to the amino acid in a naturally occurring peptide synthetase domain, fatty acid linkage domain, and/or reductase domain. For example, amino acids with aliphatic side chains, including glycine, alanine, valine, leucine, and isoleucine, may be substituted for each other; amino acids having aliphatic-hydroxyl side chains, including serine and threonine, may be substituted for each other; amino acids having amide-containing side chains, including asparagine and glutamine, may be substituted for each other; amino acids having aromatic side chains, including phenylalanine, tyrosine, and tryptophan, may be substituted for each other; amino acids having basic side chains, including lysine, arginine, and histidine, may be substituted for each other; and amino acids having sulfur-containing side chains, including cysteine and methionine, may be substituted for each other.

In certain embodiments, amino acid substitutions result in an engineered domain that comprises an amino acid whose side chain exhibits similar chemical properties to an amino acid present in a naturally occurring peptide synthetase domain, fatty acid linkage domain (e.g. a beta-hydroxy fatty acid-linkage domain), and/or reductase domain. For example, in certain embodiments, amino acids that comprise hydrophobic side chains may be substituted for each other. In some embodiments, amino acids may be substituted for each other if their side chains are of similar molecular weight or bulk. For example, an amino acid in an engineered domain may be substituted for an amino acid present in the naturally occurring domain if its side chains exhibits a minimum/maximum molecular weight or takes up a minimum/maximum amount of space.

In certain embodiments, an engineered peptide synthetase domain, fatty acid linkage domain (e.g. a beta-hydroxy fatty acid linkage domain), and/or reductase domain present in an engineered polypeptide of the present disclosure exhibits homology to a naturally occurring peptide synthetase domain, fatty acid linkage domain, and/or reductase domain. In certain embodiments, an engineered domain of the present disclosure comprises a polypeptide or portion of a polypeptide whose amino acid sequence is 50, 55, 60, 65, 70, 75, 80, 85 or 90 percent identical or similar over a given length of the polypeptide or portion to a naturally occurring domain. In certain embodiments, an engineered domain of the present disclosure comprises a polypeptide or portion of a polypeptide whose amino acid sequence is 91, 92, 93, 94, 95, 96, 97, 98, or 99 percent identical or similar over a given length of the polypeptide or portion to a naturally occurring domain. The length of the polypeptide or portion over which an engineered domain of the present disclosure is similar or identical to a naturally occurring domain may be, for example, 5, 6, 7, 8, 9, 10, 15, 20, 25, 30, 35, 40, 45, 50, 60, 70, 80, 90, 100, 200, 300, 400, 500, 600, 700, 800, 900, 1000 or more amino acids.

In certain embodiments, an engineered peptide synthetase domain, fatty acid linkage domain (e.g. a beta-hydroxy fatty acid linkage domain), and/or reductase domain present in an engineered polypeptide of the present disclosure comprises an amino acid sequence that conforms to a consensus sequence of a class of engineered peptide synthetase domains, fatty acid linkage domains, and/or reductase domains. For example, a reductase domain may comprise the consensus sequence: [LIVSPADNK]-x(9)-{P}-x(2)-Y-[PSTAGNCV]-[STAGNQCIVNI]-[STAGC]-K-{PC}-[SAGFYR]-[LIVMSTAGLD]-x-{K}-[LlIVMFYW]-{D}-x-{YR}-[LIVMFYWGAPTHQ]-[GSACQRHM](SEQ ID NO: 1).

In certain embodiments, an engineered peptide synthetase domain, fatty acid linkage domain (e.g. a beta-hydroxy fatty acid linkage domain), and/or reductase domain present in an engineered polypeptide is both: 1) homologous to a naturally occurring engineered peptide synthetase domain, fatty acid linkage domain, and/or reductase domain, and 2) comprises an amino acid sequence that conforms to a consensus sequence of a class of engineered peptide svnthetase domain, fatty acid linkage domain, and/or reductase domains.

In certain embodiments, engineered polypeptides of the present disclosure comprise two or more naturally occurring polypeptide domains that are covalently linked (directly or indirectly) in the polypeptide in which they occur, but are linked in the engineered polypeptide in a non-natural manner. As a non-limiting example, two naturally occurring polypeptide domains that are directly covalently linked may be separated in the engineered polypeptide by one or more intervening amino acid residues. Additionally or alternatively, two naturally occurring polypeptide domains that are indirectly covalently linked may be directly covalently linked in the engineered polypeptide, e.g. by removing one or more intervening amino acid residues.

In certain embodiments, two naturally occurring peptide domains that are from different peptide synthetases are covalently joined to generate an engineered polypeptide of the present disclosure. As a non-limiting example, engineered polypeptides of the present disclosure may comprise a beta-hydroxy fatty acid linkage domain from the SRFA protein, and a peptide synthetase and reductase domain from the gramicidin synthetase complex, which peptide synthetase domain and beta-hydroxy fatty acid linkage domain are covalently linked to each other (e.g. via peptide bonds); in some embodiments, the reductase domain is also covalently linked to the peptide synthetase and fatty acid linkage domains.

The present disclosure encompasses engineered polypeptides comprised of these and other peptide synthetase domains, fatty acid linkage domains, and reductase domains from a variety of peptide synthetase complexes. In certain embodiments, engineered polypeptides of the present disclosure comprise at least one naturally occurring polypeptide domain and at least one engineered domain.

in certain embodiments, engineered polypeptides of the present disclosure comprise one or more additional peptide synthetase domains, fatty acid linkage domains, and/or reductase domains, and still produce an acyl alcohol of interest.

Reductase Polypeptides

A reductase polypeptide for use in accordance with the present disclosure may be any polypeptide that 1) catalyzes reduction of an amino acid, or reduction product of an amino acid (e.g., an amino aldehyde) attached by a peptide synthetase complex and/or 2) releases a product of the peptide synthetase complex with the terminal residue as a reduction product of an amino acid (e.g., an amino aldehyde or an alcohol such as an amino alcohol) from the peptide synthetase complex.

In some embodiments, a reductase polypeptide releases the product of the engineered polypeptide as an acyl aldehyde (e.g., an acyl amino aldehyde) or an acyl alcohol (e.g., an acyl amino alcohol). Generally, in many embodiments, the reduction from an amino acid to any amino alcohol is a two-step reduction.

In some embodiments, a reductase polypeptide catalyzes both steps of the two-step reduction, e.g., the reductase polypeptide catalyzes both a reduction of an acyl amino acid to an acyl amino aldehyde and a subsequent reduction of the acyl amino aldehyde to an acyl alcohol, e.g., acyl amino alcohol, and releases an acyl amino alcohol from the peptide synthetase from which the acyl amino acid had been produced In some embodiments, a first reductase polypeptide catalyzes one step of a the two-step reduction, and a second reductase polypeptide catalyzes the second step of the two-step reduction. For example, in some embodiments, a first reductase polypeptide catalyzes a reduction of the acyl amino acid to an acyl amino aldehyde, and a second reductase polypeptide catalyzes a reduction of the acyl amino aldehyde to an acyl alcohol, e.g., acyl amino alcohol. In some embodiments, the first reductase polypeptide releases an acyl amino aldehyde, which is subsequently reduced by the second reductase polypeptide to an acyl alcohol, e.g., acyl amino alcohol. In some embodiments, the first reductase polypeptide does not release the acyl amino aldehyde, and instead, the second reductase polypeptide both catalyzes a reduction of the acyl amino aldehyde to an acyl alcohol (e.g., acyl amino alcohol) and releases the acyl alcohol product.

In some embodiments, a reductase polypeptide has an amino acid sequence that is identical to that of a reductase polypeptide found in nature. In some embodiments, a reductase polypeptide has an amino acid sequence that differs from but shows an overall level of sequence identity with and/or includes one or more characteristic sequence elements of a reductase polypeptide found in nature.

In some embodiments, a reductase polypeptide is an engineered polypeptide, for example, in that it has an amino acid sequence that has been selected and/or generated by the hand of man. For example, such engineered reductase polypeptides may comprise one or more amino acid insertions, deletions, substitutions, or transpositions as compared to a naturally occurring reductase polypeptide. Additionally or alternatively, such engineered reductase domains may exhibit homology to a naturally occurring reductase polypeptide, as measured by, for example, percent identity or similarity at the amino acid level, for example, at least 70%0, at least 75%, at least 80%, at least 85%, at least 90%, at least 95%0, or at least 98% identity at the amino acid level. Additionally or alternatively, such engineered reductase polypeptides may comprise one or more amino acid sequences that conform to a consensus sequence characteristic of a given naturally occurring reductase polypeptide.

In certain embodiments, an engineered reductase polypeptide that is similar to a naturally occurring reductase polypeptide retains the ability of the naturally occurring reductase polypeptide to act on an amino acid (or an amino acid residue within an acyl amino acid) that is incorporated into a product by a peptide synthetase, catalyze a reduction reaction, and/or release a reduced product (e.g., acyl aldehyde or acyl alcohol) from the peptide synthetase.

Engineered reductase polypeptides may exhibit one or more advantageous properties as compared to a naturally occurring reductase domain. For example, engineered reductase polypeptides, or engineered polypeptides comprising such engineered reductase polypeptides, may yield an increased amount of an acyl alcohol, may be more stable in a given host cell, may be less toxic to a given host cell, etc. Those of ordinary skill in the art will understand various advantages of engineered reductase polypeptides of the present disclosure, and will be able to recognize and optimize such advantages in accordance with the teachings herein.

In some embodiments, a reductase polypeptide (whether having the same or different sequence than that of a naturally occurring reductase polypeptide) is expressed from a heterologous promoter. In some embodiments, a reductase polypeptide is linked with one or more domains or sequences with which not it is not linked in nature, and/or it is linked with one more domains or sequences with an ordering that is not found in nature. In certain embodiments, reductase polypeptide is part of a larger polypeptide that includes a reductase domain and one or more other domains or sequences. The larger polypeptide may itself be an engineered polypeptide or a naturally occurring polypeptide.

In some embodiments, an engineered reductase polypeptide may comprise a reductase domain that has been engineered to be covalently linked with one or more other domains or sequences.

In some embodiments, a reductase polypeptide is not covalently linked to any other polypeptide domains or sequences.

As noted above, in some embodiments, a reductase polypeptide catalyzes both steps of the two-step reduction and releases an acyl alcohol, e.g., an acyl amino alcohol. As a non-limiting example of such a reductase polypeptide, the final amino acid incorporated by the peptide synthetase system that produces mycobacterial glycopeptidedolipid is alanine. Subsequent to alanine incorporation, a reductase domain catalyzes a two-electron reduction that can use either NADH or NADPH as a cofactor (Chlabra et al., "Nonprocessive [2+2]e off-loading reductase domains from mycobacterial nonribosomal peptide synthetases," PNAS 109(15):5681-5686, 2012, the entire contents of which are herein incorporated by reference), thereby reducing alanine to an aldehyde, alaninal. NAD(P) then dissociates, and the reductase domain is re-loaded with NAD(P)H and reduces alaninal to alaninol. The product, having alaninol as the terminal residue, dissociates from the peptide synthetase complex, followed by dissociation of NAD(P).

As noted above, in some embodiments, a first reductase polypeptide catalyzes the first step of the two-step reduction and a second reductase polypeptide catalyzes the second step of the two-step reduction. As a non-limiting example, the final amino acid incorporated by the gramicidin peptide synthetase is glycine. Subsequent to glycine incorporation, a first reductase domain catalyzes a two-electron reduction that can use either NADH or NADPH as a cofactor, thereby converting glycine into glycinaldehyde. A separate (second) reductase polypeptide, the product of the LgrE gene, converts glycinaldehyde into ethanolamine by an NADPH-dependent reduction reaction (Schracke et al., "Synthesis of linear gramicidin requires the cooperation of two independent reductases," *Biochemistry* 44:8507-8513, 2005, the contents of which are herein incorporated in their entirety).

In some embodiments in which at least two reductase polypeptides are used, at least one is covalently linked to one or more domains within an engineered polypeptide, and at least one is not covalently linked one or more domains within an engineered polypeptide. For example, a first reductase polypeptide may be covalently linked one or more domains within an engineered polypeptide, while a second reductase polypeptide may be not covalently linked to one or more domains within an engineered polypeptide.

In some embodiments in which at least two reductase polypeptides are used, at least two reductase polypeptides are covalently linked to one or more domains within an engineered polypeptide. For example, a first reductase polypeptide and second reductase polypeptide may be covalently linked to other polypeptide domains (such as a fatty acid linkage domain and one or more subdomains of a peptide synthetase module) of an engineered polypeptide, and the first and second reductase polypeptides are covalently linked to one another either directly (with no other polypeptide domains intervening) or indirectly (with at least one other polypeptide domain intervening).

In some embodiments in which at least two reductase polypeptides are used, at least two reductase polypeptides are not covalently linked to any other polypeptide domain. For example, in some embodiments, an engineered polypeptide that is useful in producing an acyl amino acid is provided, and a first reductase polypeptide and a second reductase polypeptide are both separate from the engineered polypeptide.

In some embodiments in which at least two reductase polypeptides are used, at least two reductase polypeptides are covalently linked to one another, but are not covalently linked to any other type of polypeptide domain, e.g., a fatty acid linkage domain or any subdomain of a peptide synthetase module. For example, a first reductase polypeptide may be covalently linked to a second reductase polypeptide, and the first and second reductase polypeptides are not covalently linked to any other type of polypeptide domain.

Table 1 provides a non-limiting list amino alcohols that are present at the terminal ends of products known to be synthesized by peptide synthetases. References that describe the corresponding peptide synthetases or relevant modules are also listed in Table 1. Accordingly, Table 1 represents a non-limiting list of amino alcohols for which there is a corresponding naturally occurring reductase domain (which would reduce an amino acid into the amino alcohol and/or release it) within various peptide synthetase complexes or modules known in the art. However, it should be noted that while the naturally occurring versions of such amino alcohols are present at the ends of peptide chains (i.e. linked to an amino acid), such amino alcohols are never directly linked to fatty acids (i.e., without any intervening moieties).

TABLE 1 amino alcohols in products synthesized by peptide synthetase enzymes

| Amino alcohol | Reference (the entire contents of each of the below references are incorporated by reference herein) |
|---|---|
| alaninol | Tatham et al., "production of mycobacterial cell wall glycopeptidolipids requires a member of the MbtH-like protein family," *BMC Microbiology* 12: 118: 1-14, 2012. |
| valinol | Wiest et al., "Identification of peptaibols from *Trichoderma virens* and cloning of a peptaibol synthetase," JBC 277(23): 20862-20868, 2002. |
| phenylalaninol | Wiest et al., "Identification of peptaibols from *Trichoderma virens* and cloning of a peptaibol synthetase," JBC 277(23): 20862-20868, 2002. |
| leucinol | Wiest et al., "Identification of peptaibols from *Trichoderma virens* and cloning of a peptaibol synthetase," JBC 277(23): 20862-20868, 2002. |
| serinol | Andersson et al., "Acrebol, a novel toxic peptaibol produced by an Acremonium exuviarum indoor isolate," *J. Appl. Microbiol* 21: 1-15, 2009. |
| leucinol or isoleucinol | Degenkolb et al., "The *Trichoderma brevicompacium* clade: a separate lineage with new species, new peptaibiotics, and mycotoxins," Mycol Progress 7(3): 177-219, 2008. |
| tryptophanol | Lee et al., "Isolation and sequence analysis of new peptaibol, boletusin, from *Boletus* spp.," J Pept Sci 5(8): 374-378, 1999. |
| ethanolamine | Kessler et al., "The linear pentadecapeptide gramicidin is assembled by four multimodular nonribosomal peptide synthetases that comprise 16 modules with 56 catalytic domains," J Biol Chem 279(9): 7413-7429, 2004. |

However, as previously mentioned, the acyl alcohols of the present disclosure are not limited to acylated versions of the alcohols listed in Table 1. For example, additional reductase polypeptides may be known in the art that act on additional amino acids, and/or additional reductase polypeptides may be engineered to act on additional amino acids.

In some embodiments, a reductase polypeptide is at least 70%, at least 75%, at least 80%, at least 85%, at least 90%, at least 950%, or at least 98%-0 identical at the amino acid level to the reductase domain of the terminal peptide synthetase domain (module 16) of the gramicidin peptide synthetase, e.g., that from *Bacillus brevis*.

In some embodiments, a reductase polypeptide is at least 70%, at least 75%, at least 80%, at least 85%, at least 90%, at least 95%, or at least 98% identical at the amino acid level to the reductase domain of the terminal mycobacterial glycopeptidedolipid peptide synthetase domain, such as, by way of non-limiting example, the glycopeptidedolipid peptide synthetase domain from *Mycobacterium smegmatis*.

In some embodiments, a reductase polypeptide is at least 70%, at least 75%, at least 80%, at least 85%, at least 90%, at least 95%, or at least 98% identical at the amino acid level to the polypeptide produced from the *Bacillus brevis* LgrE gene. (See, e.g., FIGS. 6A and 6B).

In some embodiments, such as reductase polypeptide is the "second" reductase polypeptide in which both a first and a second reductase polypeptide is used.

In some embodiments, a reductase polypeptides is characterized by the presence of the consensus sequence: [LIVS-PADNK]-x(9)-{P}-x(2)-Y-[PSTAGNCV]-[STAGNQ-CIVM]-[STAGC]-K-{PC}-[SAGFYR]-[LIVMSTAGD]-x-{K}-[LIVMFYW]-{D}-x-{YR}-[LIVMFYWGAPTHQ]-[GSACQRHM](SEQ ID NO: 1), where square brackets ("[ ]") indicate amino acids that are typically present at that position, squiggly brackets ("{ }") indicate amino acids that amino acids that are typically not present at that position, and "x" denotes any amino acid or a gap. X(9) for example denotes any amino acids or gaps for nine consecutive positions.

Compositions

In one aspect, provided are compositions comprising an acyl alcohol (such as those made by methods of the present disclosure) comprising a fatty acid covalently and directly linked to an alcohol. By "directly linked," it is meant that there are no intervening moieties (such as amino acids) between the fatty acid and the alcohol.

In some embodiments, the fatty acid is linked to the alcohol via an amide bond.

In some embodiments, the alcohol is an amino alcohol.

In some embodiments, compositions of the present disclosure further comprise one or more components of an engineered microbial cell, for example, but not limited to, intact microbial cells, macromolecules present in the cell wells of such cells, and/or polypeptide endogenously expressed by the engineered microbial cell. In some embodiments, the one or more components comprise an intact microbial cell.

Host Cells and Engineered Cells

Engineered polypeptides of the present disclosure may be introduced in any of a variety of host cells for the production of acyl amino acids. As will be understood by those skilled in the art, engineered polypeptides will typically be introduced into a host cell in one or more expression vectors. So long as a host cell is capable of receiving and propagating such an expression vector(s), and is capable of expressing the engineered polypeptide(s), such a host cell is encompassed by the present disclosure. An engineered polypeptide of the present disclosure may be transiently or stably introduced into a host cell of interest. For example, an engineered polypeptide of the present disclosure may be stably introduced by integrating the engineered polypeptide into the chromosome of the host cell. Additionally or alternatively, an engineered polypeptide of the present disclosure may be transiently introduced by introducing one or more vectors comprising the engineered polypeptide(s) into a host cell, which vector is not integrated into the genome of the host cell, but is nevertheless propagated by the host cell.

In certain embodiments, a host cell is a microbial cell. In some embodiments, the microbial cell is a bacterium. Non-limiting examples of bacteria that are useful as host cells of the present disclosure include bacteria of the genera *Escherichia*, *Streptococcus*, *Bacillus*, and a variety of other genera known to those skilled in the art. In certain embodiments, an engineered polypeptide of the present disclosure is introduced into a host cell of the species *Bacillus subtilis*.

Microbial host cells of the present disclosure may be wild type. Alternatively, microbial host cells of the present disclosure may comprise one or more genetic changes as compared to wild type species. In certain embodiments, such genetic changes are beneficial to the production of products such as acyl amino acids and/or acyl alcohols in the microbial host. For example, such genetic changes may result in increased yield or purity of the acyl amino acid or acyl alcohol, and/or may endow the microbial host cell with various advantages useful in the production of acyl amino acids or acyl alcohols (e.g., increased viability, ability to utilize alternative energy sources, etc.).

In certain embodiments, the present disclosure provides an engineered microbial cell (e.g., an engineered bacterial cell) comprising one or more polypeptides of the present disclosure. In some embodiments, the engineered microbial cell also expresses one or more expression vectors from which one or more polypeptides can be expressed. For example, in certain embodiments, the engineered microbial cell expresses an engineered polypeptide of the present disclosure. For example, the engineered microbial cell can comprise an engineered polypeptide comprising a fatty acid linkage domain, a peptide synthetase domain, and a first reductase polypeptide. In some embodiments, the engineered microbial cell also includes a second reductase polypeptide distinct form the first reductase polypeptide.

In some embodiments, the present disclosure provides an engineered microbial cell comprising one or more engineered polypeptides collectively comprising: a fatty acid linkage domain, a peptide synthetase domain, and one or more reductase polypeptides, which fatty acid linkage domain and peptide synthetase domain collectively can produce an acyl amino acid, and which one or more reductase polypeptides are collectively capable of reducing the acyl amino acid to any acyl alcohol. In some embodiments, the engineered microbial cell lacks a thioesterase domain, described in further detail, for example, in U.S. Pat. No. 7,981,685. In some embodiments, the engineered microbial cell is a bacterial cell, e.g., a *Bacillus* cell. In some embodiments, the *Bacillus* cell is a *Bacillus subtilis* cell.

Engineered bacterial cells can be grown in liquid media for a period of time. For example, for at least or about one day, at least or about two days, at least or about three days, or at least or about four days. Typical culture volumes include, for example, about 2 mL, about 5 mL, about 10 mL, or about 25 mL, or more than about 25 mL. In some embodiments, cells are grown for about 4 days in 10 mL cultures.

In some embodiments, products (e.g., acyl alcohols such as FA-Eth) from the one or more polypeptides in the engineered bacterial cell are secreted into the liquid media. Cells can be removed from the liquid medium, e.g., by centrifugation, thus facilitating the analysis and/or isolating of any products secreted into the liquid medium. Culture media or subsequently processed liquids can then be analyzed by methods known in the art, including LC-MS.

In certain embodiments, the host cell is a plant cell. Those skilled in the art are aware of standard techniques for introducing an engineered polypeptide of the present disclosure into a plant cell of interest such as, without limitation, gold bombardment and *agrobacterium* transformation. In certain embodiments, the present disclosure provides a transgenic plant that comprises an engineered polypeptide that produces an acyl amino acid of interest. Any of a variety of plants species may be made transgenic by introduction of an engineered polypeptide of the present disclosure, such that the engineered polypeptide is expressed in the plant and produces an acyl amino acid of interest. The engineered polypeptide of transgenic plants of the present disclosure may be expressed systemically (e.g. in each tissue at all times) or only in localized tissues and/or during certain periods of time. Those skilled in the art will be aware of various promoters, enhancers, etc. that may be employed to control when and where an engineered polypeptide is expressed.

Insects, including insects that are threats to agriculture crops, produce acyl amino acids that are likely to be important or essential for insect physiology. For example, an enzyme related to peptide synthetases produces the product of the Drosophila Ebony genes, which product is important for proper pigmentation of the fly, but is also important for proper function of the nervous system (see e.g., Richardt et al., Ebony, a novel nonribosomal peptide synthetase for beta-alanine conjugation with biogenic amines in Drosophila, J. Biol. Chem., 278(42):41160-6, 2003). Acyl amino acids are also produced by certain Lepidoptera species that are a threat to crops. Thus, compositions and methods of the present disclosure may be used to produce transgenic plants that produce an acyl alcohol of interest that kills such insects or otherwise disrupts their adverse effects on crops. For example, an engineered polypeptide that produces an acyl alcohol that is toxic to a given insect species may be introduced into a plant such that insects that infest such a plant are killed. Additionally or alternatively, an engineered polypeptide that produces an acyl alcohol that disrupts an essential activity of the insect (e.g., feeding, mating, etc.) may be introduced into a plant such that the commercially adverse effects of insect infestation are minimized or eliminated. In certain embodiments, an acyl alcohol of the present disclosure that mitigates an insect's adverse effects on a plant is an acyl alcohol that is naturally produced by such an insect. In certain embodiments, an acyl alcohol of the present disclosure that mitigates an insect's adverse effects on a plant is a structural analog of an acyl alcohol that is naturally produced by such an insect. Compositions and methods of the present disclosure are extremely powerful in allowing the construction of engineered polypeptides that produce any of a variety of acyl amino acids, which acyl amino acids can be used in controlling or eliminating harmful insect infestation of one or more plant species.

EXAMPLES

Example 1—Engineering a Bacterial Strain to Produce Fa-Ethanolamine

The present Example describes the design of an engineered bacterial strain for use in certain methods of the disclosure to generate an acyl alcohol, in this case, FA-ethanolamine. FA-ethanolamine can be used as a nonionic surfactant, and its cleavage will produce ethanolamine and fatty acids as separate products.

The final amino acid incorporated by the *Bacillus brevis* gramicidin peptide synthetase is glycine. (See, e.g., Kessler et al., "The linear pentadecapeptide gramicidin is assembled by four multimodular nonribosomal peptide synthetases that comprise 16 modules with 56 catalytic domains."*J Bio Chem.* 2004 Feb 27: 279(9); 7413-9, the entire contents of which are herein incorporated by reference.) The reductase domain of the gramicidin peptide synthetase catalyzes a two electron reduction that can use either NADH or NADPH as a cofactor, which converts glycine into glycinaldehyde. Aldehyde can be converted into ethanolamine by an NADPH-dependent reduction reaction catalyzed by a second enzyme such as that encoded by the LgrE gene. (See, e.g., Schracke et al., "Synthesis of linear gramicidin requires the cooperation of two independent reductases." *Biochemistry.* 2005 Jun 14: 44(23);8507-13, the entire contents of which are herein incorporated by reference.)

Expression Construct to Generate FA-Glycine and Reduce it to FA-Glycinaldehyde

In the present Example, a fusion construct driven by the psrf promoter is generated that includes, in the following order, the condensation domain of the first module of the *Bacillus subtilis* srfAA peptide synthetase complex and the adenylation, thiolation, and reductase domains of module 16 (the last module) of the *Bacillus brevis* gramicidin synthetase. In use in accordance to certain methods of the present disclosure, the condensation domain will attach a fatty acid onto glycine (which is specified by the adenylation domain of module 16), which will then be reduced by the reductase domain of module 16 to glycinaldehyde.

The lgr gene cluster is responsible for production of gramicidin in the *Bacillus brevis* ATCC 8185 strain. The complete nucleotide sequence of this gene cluster is available in GenBank under accession number AJ566197. The LgrD gene encodes a synthetase with four modules, the last of which is "module 16" of the *Bacillus brevis* gramicidin synthetase mentioned above.

The sequence of module 16 was analyzed and annotated using information from Manavalan et al. "Molecular modeling of the reductase domain to elucidate the reaction mechanism of reduction of peptidyl thioester into its corresponding alcohol in non-ribosomal peptide synthetases." *BMC Structural Biology.* 2010, 10:1. DOI: 10.1186/1472-6807-10-1, (the entire contents of which are herein incorporated by reference).

To define the adenylation domain, a conserved sequence in adenylation domains, TSGSTGNPKG (SEQ ID NO: 2), was identified near the end of the module 16 sequence. Because the adenylation domains of peptide synthetase modules are specific for a given amino acid, the adenylation domain in module 16 was further defined by iteratively performing sequence comparisons with various other known peptide synthetase domains specific for different amino acids, and discarding regions of sequence similarity. Sequence comparisons were performed using the ClustalW2 sequence alignment tool at the EMBL-EBI website (http://www.ebi.ac.uk/Tools/msa/clustalw2/).

After initial analyses, the amino acid sequence of the condensation, adenylation, and reductase domains of module 16 (glycine module) of the *Bacillus brevis* gramicidin synthetase complex was identified (SEQ ID NO: 3). This sequence is depicted in FIG. 4.

After further analysis, the adenylation domain of module 16 (glycine module) of the Bacillus brevis gramicidin synthetase complex was identified. This sequence is depicted in FIG. 5A (amino acid sequence, SEQ ID NO: 4) and 5B (nucleotide coding sequence, SEQ ID NO: 5).

To identify fusion points to replace the condensation domain of the gramicidin synthetase glycine module (module 16) with the condensation domain of srfAA module 1, the amino acid sequences of module 1 of the srfAA subunit (the "FA-Glu module) from Bacillus subtilis and of the IgrD glycine module from Bacillus brevis were compared. This comparison identified eight potential fusion regions for replacement of the condensation domain.

Using molecular cloning techniques known in the art, various expression constructs ("Construct 1") with different fusion points are made in which the psrf promoter drives expression of a fusion polypeptide containing, in order, the condensation domain of the first module of the srfAA subunit of Bacillus subtilis, followed by the adenylation, thiolation, and reductase domains of Bacillus brevis Expression Construct to Reduce FA-Glycinaldehyde and Release it as FA-Ethanolamine An expression construct ("Construct 2") in which an IgrE gene encoding the polypeptide of SEQ ID NO: 6 (depicted in FIG. 6A) is driven by the prsf promoter. LgrE is a reductase that will reduce glycinaldehyde to ethanolamine.

Generation of Engineered Cells Producing FA-Ethanolamine

Construct 1 and Construct 2 are both introduced into Bacillus subtilis cells and co-expressed. The cells are then grown, and production of FA-eth from such cells is measured by methods described herein and/or in U.S. Pat. No. 7,981,685.

Example 2—Validation of Quantitative Liquid Chromatography (Lc/Ms) Method

The present Example demonstrates the validity of a quantitative method developed by the present inventor. The method had been used by the present inventor to quantify FA-Glu, FA-Gly, surfactin, surfactin analogs, and other surfactants. This same method can also be used to quantify acyl alcohols such as FA-ethanolamine (FA-Eth). Details of the LC/MS method and representative data can be found in Tseng et al., "Characterization of the surfactin synthetase C-terminal thioesterase domain as a cyclic depsipeptide synthase," Biochemistry 41(45):13350-13359, 2002, the entire contents of which are incorporated by reference herein.

Figure 7:
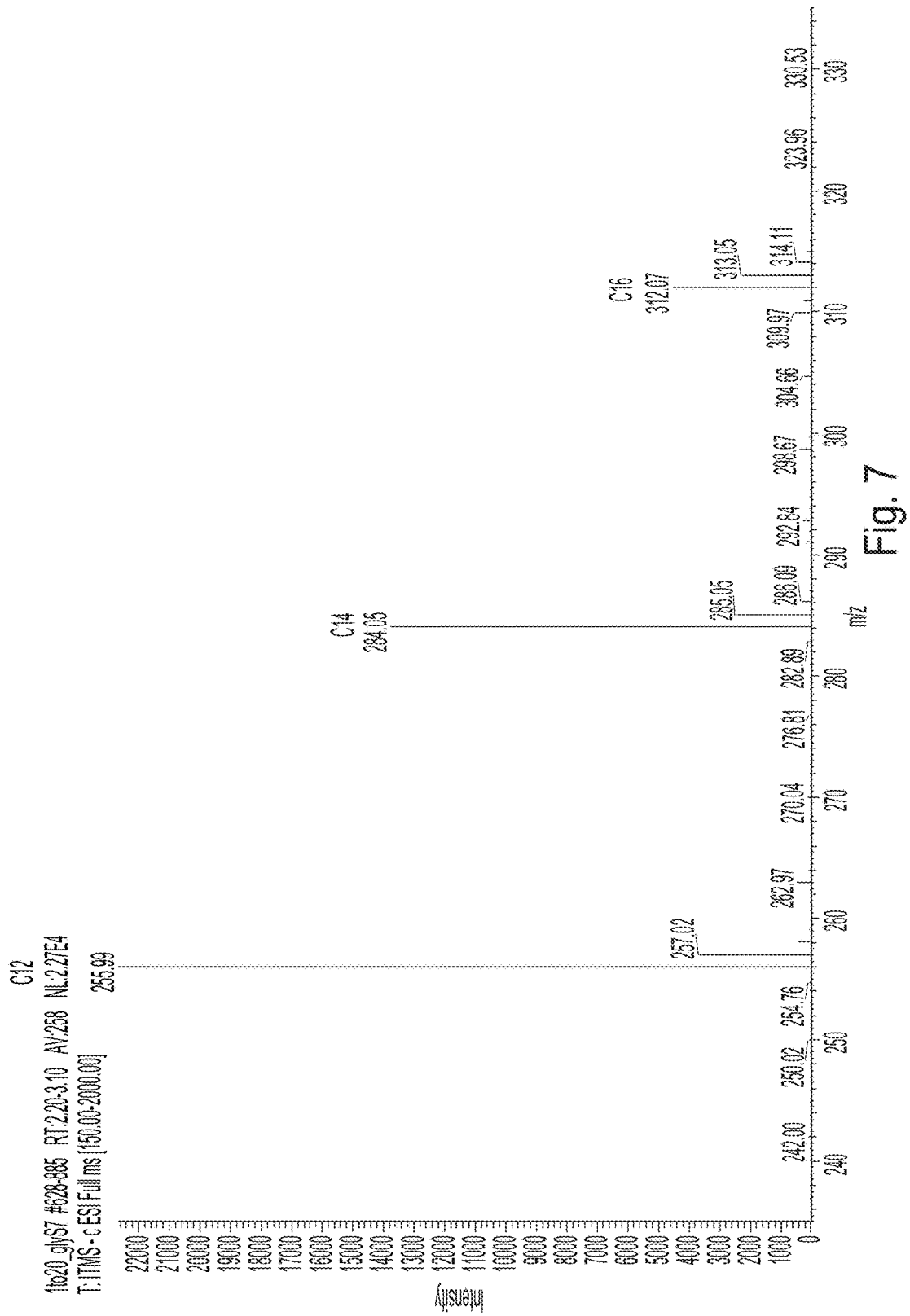
FIG. 7, comprising panels A and B, depict results from experiments validating a quantitative LCMS method to analyze a commercial preparation of cocoyl glycinate.
Figure 7:
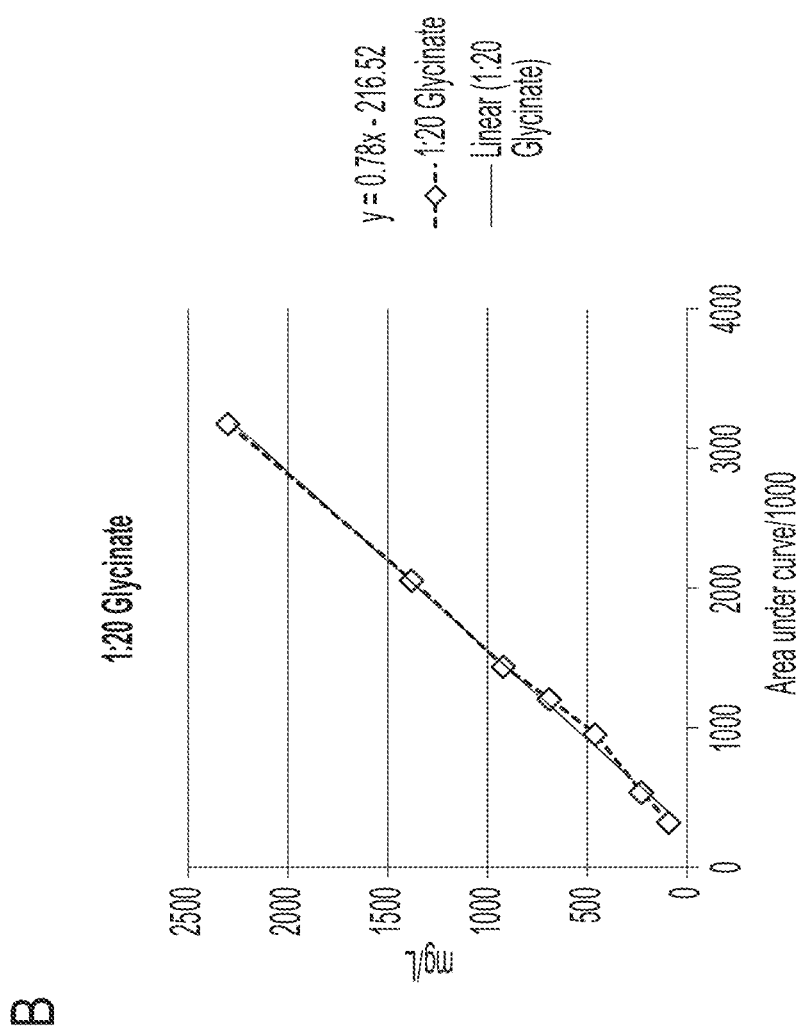

In the present Example, this quantitative method was used to analyze a commercial preparation of cocoyl glycinate. It was confirmed that the cocoyl glycinate surfactant is primarily composed of glycine linked to lauric acid (a 12 carbon fatty acid (C12)). In particular, it was found that the surfactant is composed of glycine linked to: C12 (60%), C14 (33%), and C16 (7%) (FIG. 7, panel A). It was also found that the LC/MS signal increased linearly as increasing amounts of the surfactant were measured (FIG. 7, panel B), and it was possible to generate a standard curve.

Example 3—Cleavage of an Acyl Amino Acid Using Acid

The present Example illustrates cleavage of an acyl amino acid into free fatty acids and free amino acids using a method of the present disclosure. In the present Example, the acyl amino acid beta-myristic glutamate (FA-Glu) was successfully cleaved using acid and heat, thereby obtaining glutamate and a beta-hydroxylated fatty acids.

FA-Glu was produced by an engineered polypeptide comprising a peptide synthetase complex by methods described in U.S. Pat. No. 7,981,685 (issued on Jul. 19, 2011), the entire contents of which are herein incorporated by reference. One thousand ng of one sample of FA-Glu was not treated. Nine-hundred ng of a second sample of FA-Glu was treated with 6N HCl at 100° C. for 24 hours. The untreated and treated samples of FA-Glu were analyzed using an amino acid analyzer.

In the untreated sample, no amino acids were detected (FIG. 8, panel A). A small ammonia peak was observed and was due to the use of ammonium hydroxide during preparation of the surfactant. In addition, a standard that was co-injected with the sample eluted at a time of approximately 37 minutes.

In the HCl-treated sample, a very strong glutamate peak was detected (FIG. 8, panel B). Significantly, no other amino acids were detected, indicating that the sample was very pure (free of protein contamination) and that the engineered polypeptide that produced the FA-Glu had high specificity, exclusively linking fatty acids to glutamate (and not to other amino acids). About 250 ng of free glutamate was detected. Thus, approximately 26.320% of the injected material was detected as glutamate. On a weight basis, glutamate represents about 40% of the mass of FA-Glu. Thus, complete hydrolysis of FA-Glu is expected to release about 380 ng of glutamate.

These data suggest that about 66% of the input FA-Glu was converted to free fatty acid plus free glutamate by treating FA-Glu with acid and heat.

Example 4—Cleavage of an Acyl Amino Acid Using an Enzyme

The present Example illustrates cleavage of an acyl amino acid into free fatty acids and free amino acids using a method of the present disclosure. In the present Example, the acyl amino acid beta-myristic glutamate (FA-Glu) was successfully cleaved using an enzyme, thereby obtaining glutamate and beta-hydroxylated fatty acids.

Preparation of FA-Glu Substrates

The compound FA-Glu was produced by an engineered Bacillus subtilis strain based on Bacillus subtilis strain OKB105 Δ(upp)Spect$^R$ and engineered to encode the wild-type module 1 (with specificity for glutamic acid) and an engineered module 2 with specificity for leucine. FA-Glu was produced by this engineered strain during fermentation in 19-salts media (6 g/L $Na_2HPO_4$, 3 g/L $KH_2PO_4$, 0.5 g/L NaCl, 1 g/L $NH_4Cl$) with a final concentration of 30 g/L glycerol and 18 g/L corn-steep liquor.

Cells were removed from the fermentation broth by centrifugation. FA-Glu was purified from the fermentation broth using a C18-derivatized silica reverse phase column (Millipore, 3 mL Sep-Pak C18 Column). The C18 reverse-phase purification of FA-Glu was performed manually under vacuum, After the addition of 10 mL fermentation broth to the column, the column was washed once with water and once with 10% methanol:water. FA-Glu was eluted in 100% methanol and then dried under vacuum centrifugation.

Enzyme Reaction Conditions

After purification, 9.6 mg of crude FA-Glu was dissolved in 1.5 mL 10% water:methanol. Using LC/MS (liquid chromatography/mass spectrometry) to determine product peak area and using FA-Glu-Leu as the external mass standard, FA-Glu was determined to have an approximate concentration of 400 μM.

Acylase 1 from porcine kidney (PKA 1) was purchased from Sigma-Aldrich, product number A3010. The reaction buffer and enzyme diluent was 100 mM potassium phosphate buffer, pH 7.0, as suggested by Sigma-Aldrich (Sigma Quality Control Test Procedure: NI. A Mitz and R. J. Schlueter (1958) Biochimica Et Biophysica Acta 27, 168-172). Cobalt chloride ($CoCl_2$) was added to each reaction tube to a final concentration of 1 mM. (The online product description (www.sigmaaldrich.com) for porcine kidney acylase suggested including $Co^{2-}$ or $Zn^{2-}$ in the reaction buffer to activate porcine kidney acylase.)

Reaction conditions for the deacylation of FA-Glu by the porcine kidney acylase 1 (PKA 1) are described in Table 2. One hundred-microliters of FA-Glu corresponds to an approximate final substrate concentration of 79.8 μM (3.99 μg) per reaction sample. One hundred-microliters of acylase 1 corresponds to 100 μg of dried enzyme preparation per reaction sample. The digestions described in Table 1 were incubated at 25° C. for 96 hrs. Samples were placed at 4° C. prior to LC/MS analysis.

TABLE 2

Reaction conditions for digestion of FA-Glu with porcine kidney acylase I (PKA I)

| Reaction | Substrate | Enzyme | Buffer | Activator | Total volume $V_t$ |
|---|---|---|---|---|---|
| Reaction 1 | FA-Glu, 100 μL | PKA 1, 100 μL | 299 μL | 500 mM $CoCl_2$, 1 μL | 500 μL |
| Reaction 2 | No Substrate | PKA 1, 100 μL | 399 μL | 500 mM $CoCl_2$, 1 μL | 500 μL |
| Reaction 3 | FA-Glu, 100 μL | No Enzyme | 399 μL | 500 mM $CoCl_2$, 1 μL | 500 μL |

Analysis of Enzymatic Digestion Products by Liquid Chromatography-Mass Spectrometry (LC/MS)

Before injection into the LC/MS analyzer, enzymatic reactions were centrifuged at 10,000×g for 5 minutes, and precipitated $CoCl_2$ was pelleted. The reaction supernatant was then filtered through a Millipore Ultrafree-MC 0.45-μm column during centrifugation at 5,000×g for 5 minutes.

The LC system was comprised of a Thermo-Scientific Accela-autosampler, an Accela-pump, and an Accela-PDA detector. After digestion of FA-Glu with PKA 1, the Thermo Scientific C18-HPLC column Hypersil Gold was used to separate FA-Glu from beta-hydroxy fatty acids and glutamate. The mobile phase for the reverse phase LC separation of FA-Glu from beta-hydroxy fatty acids and glutamate was 100% water (supplemented with 1%-0 acetic acid) for 3 minutes, 100% water to 100% acetonitrile (supplemented with 1% acetic acid) in 4 minutes, 100% acetonitrile for 2 minutes, and 100% isopropanol for 4 minutes. The LC system was then re-equilibrated to 100% water for 2 minutes before the next LC/NS injection.

After LC separation, FA-Glu and beta-hydroxy fatty acids were detected using a Thermo Scientific LXQ in electrospray-negative mode. The mass spectrometer was programmed to capture from a first mass of m/z=100 to a last mass of m/z=1.200. Flow from the LC was diverted away from the MIS detector the first 2.5 minutes and into the MS detector for the remaining 12.5 minutes.

Glutamate was detected using a Thermo Scientific LXQ in positive mode. The mass spectrometer was programmed to capture from a first mass of m/z=130 to a last mass of m/z=160. Flow from the LC was diverted into the NIS detector for the first 3 minutes and away from the MS detector for the remaining 12 minutes.

Results

FIGS. 9, 10, 11, 12, and 13 depict the LC/MS chromatograms for the detection of beta-hydroxy fatty acid compounds and FA-Glu for m/z ratios (I) from 200 to 900, (2) from 190 to 300, (3) from 440 to 558, (4) from 320 to 430, and (5) from 682 to 848, respectively. Panel A in each figure depicts results from Reaction 1 (FA-Glu incubated with PKA 1), Panel B in each figure depicts results from Reaction 2 (PKAI incubated without substrate), and Panel C in each figure depicts results from Reaction 3 (FA-Glu incubated without enzyme).

Figure 9:
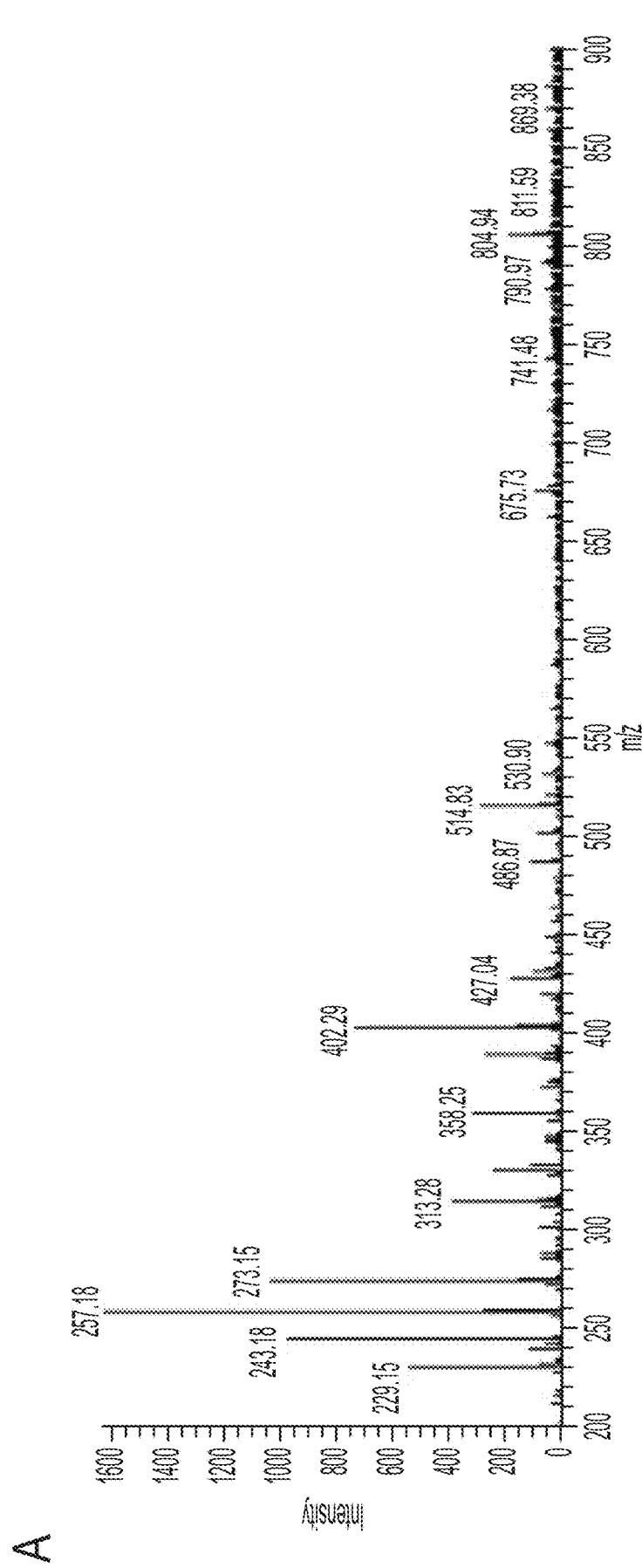
FIG. 9 (comprising panels A, B, C), FIG. 10 (comprising panels A, B, C), FIG. 11 (comprising panels A, B, C), FIG. 12 (comprising panels A, B, C), FIG. 13 (comprising panels A, B, C), and FIG. 14 (comprising panels A, B. and C) depict results from an LC/MS experiment described in Example 4 analyzing derivative products from FA-Glu treated with an acylase.
Figure 9:
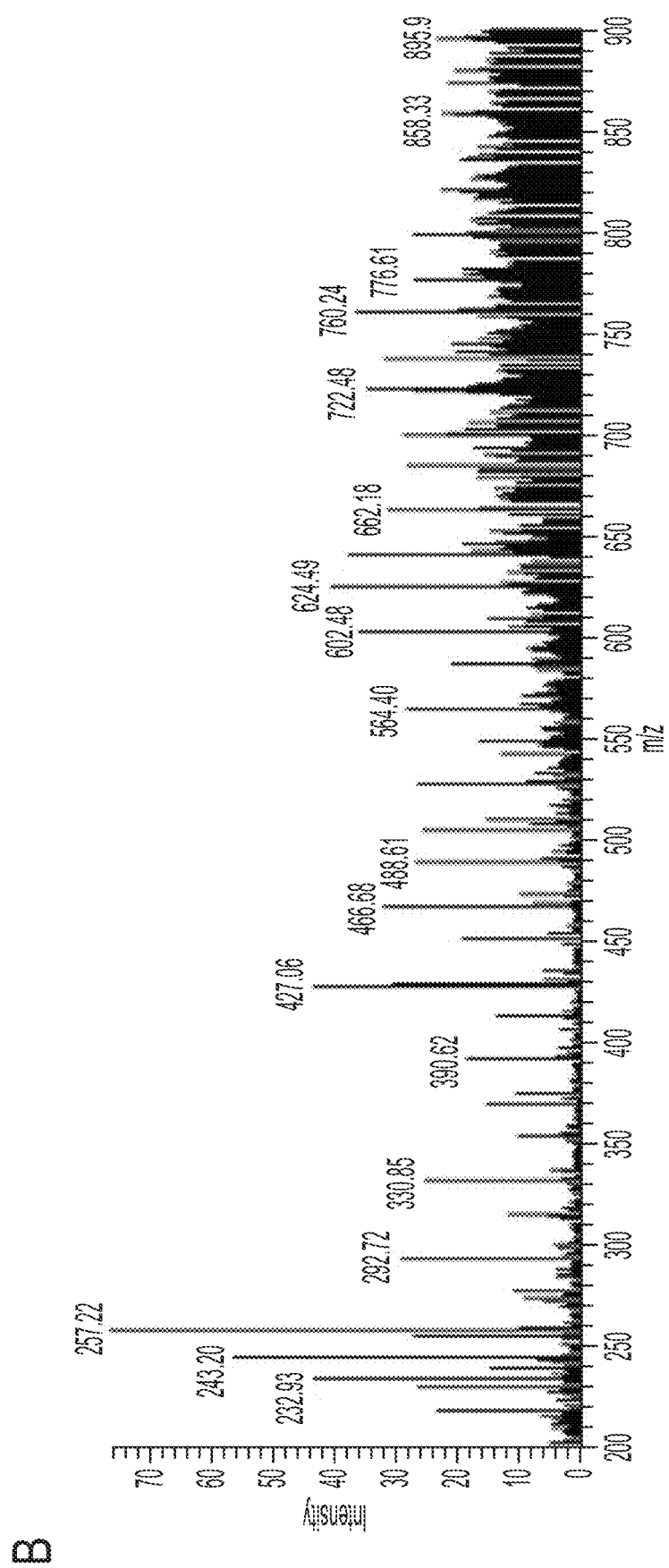
Figure 9:
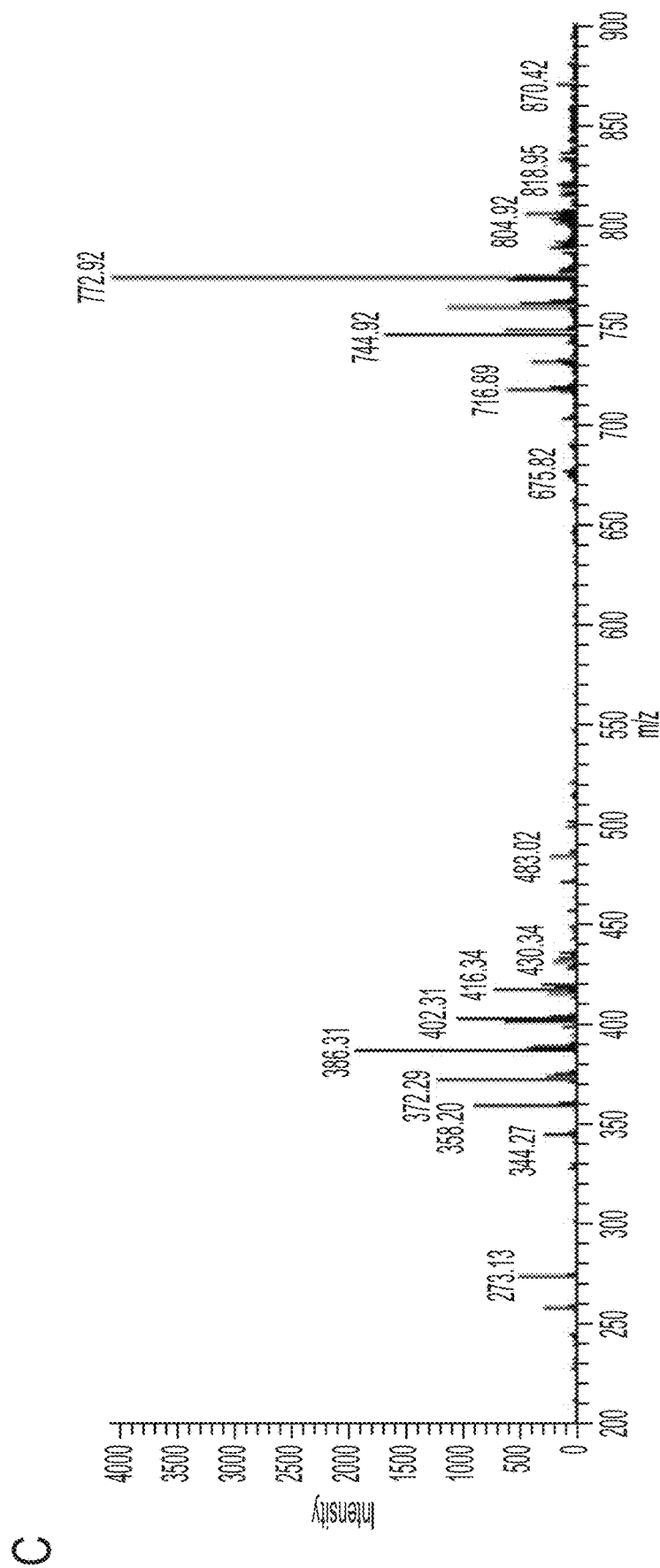
Figure 10:
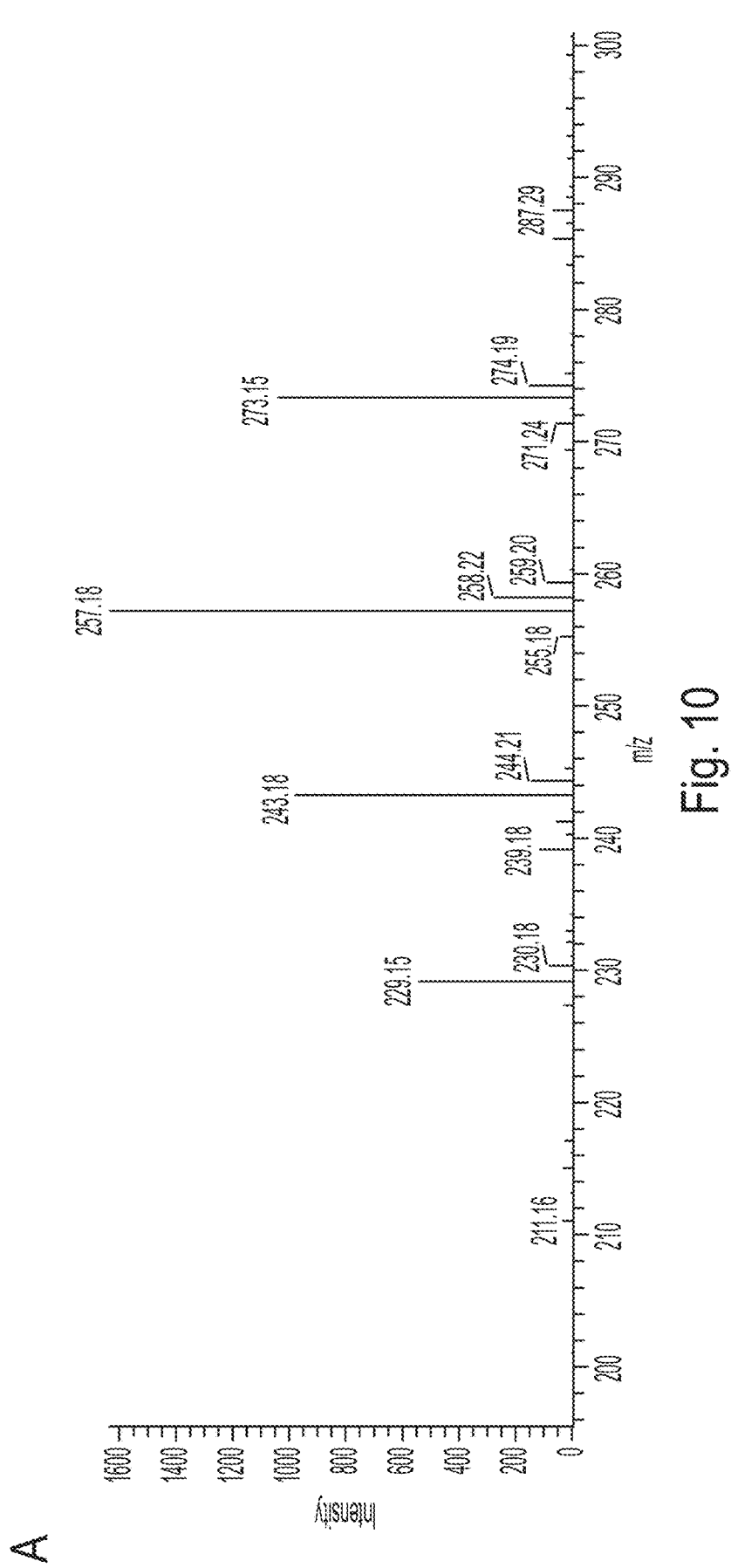
Figure 10:
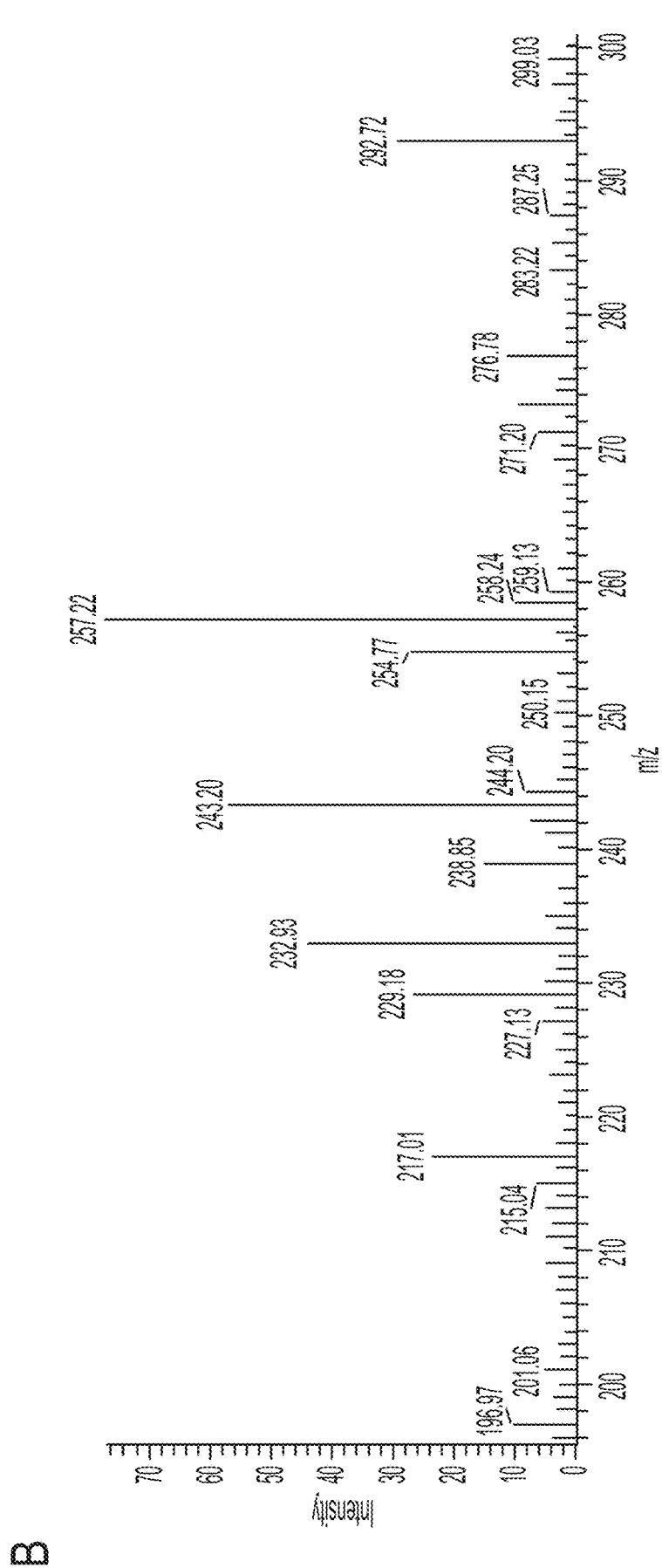
Figure 10:
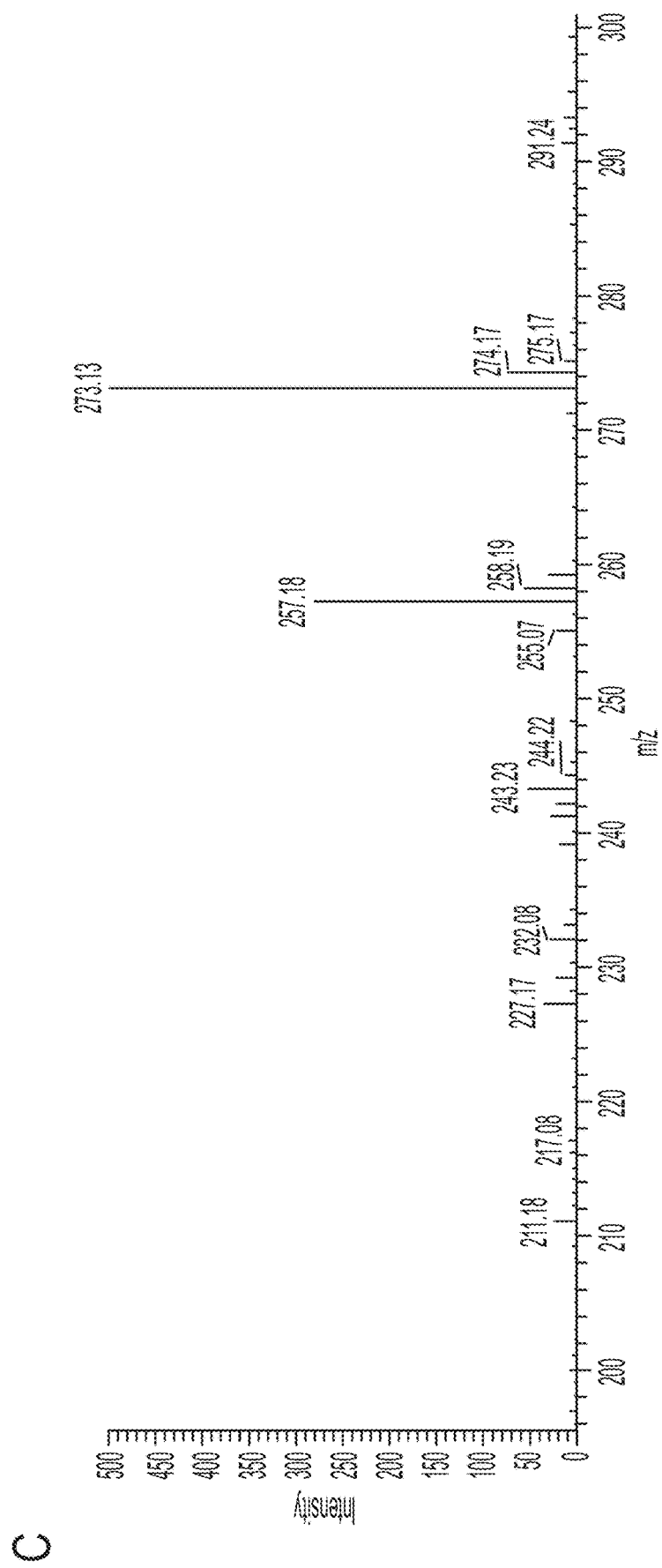

The LC/MS results confirm the formation of beta-hydroxy fatty acids from FA-Glu after incubation with PKA 1. As shown in in FIG. 9, panel A the monomer of the 14-carbon (C14) beta-hydroxy fatty acid was identified with the expected m/z ratio of 257.2, and the homodimer was identified with the expected m/z ratio of 514.8. The monomers for the C12-, C13-, C14-, and C15-beta-hydroxy fatty acids were identified with their expected m/z ratios of 229.2, 243.2, 257.2, and 273.2 respectively (FIG. 9, panel A and FIG. 10, panel A). The homodimers for the C13- and C14-beta-hydroxy fatty acids, and the heterodimer for the C14-/C5-beta-hydroxy fatty acids, were identified with m/z ratios of 486.9, 514.8, and 530.9 respectively (FIG. 9, panel A). The homodimers for the C13-, C14-, and the C15-beta-hydroxy fatty acids were identified with m/z ratios of 486.9, 514.8, and 546.8 respectively (FIG. 11, panel A), and the heterodimers for the C13-/C14-beta-hydroxy fatty acids and C14-/C15-beta-hydroxy fatty acids were identified with m/z ratios of 499.9 and 530.9, respectively (FIG. 11, panel A).

Figure 11:
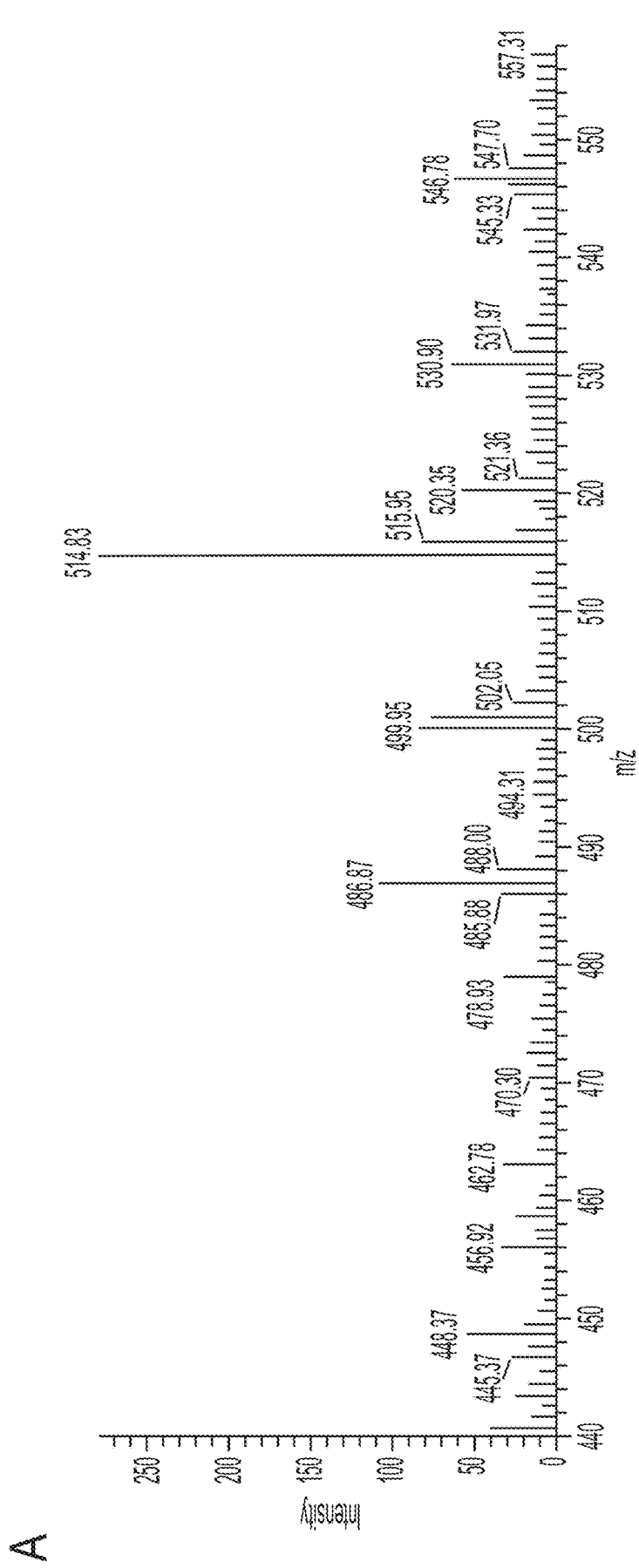
Figure 11:
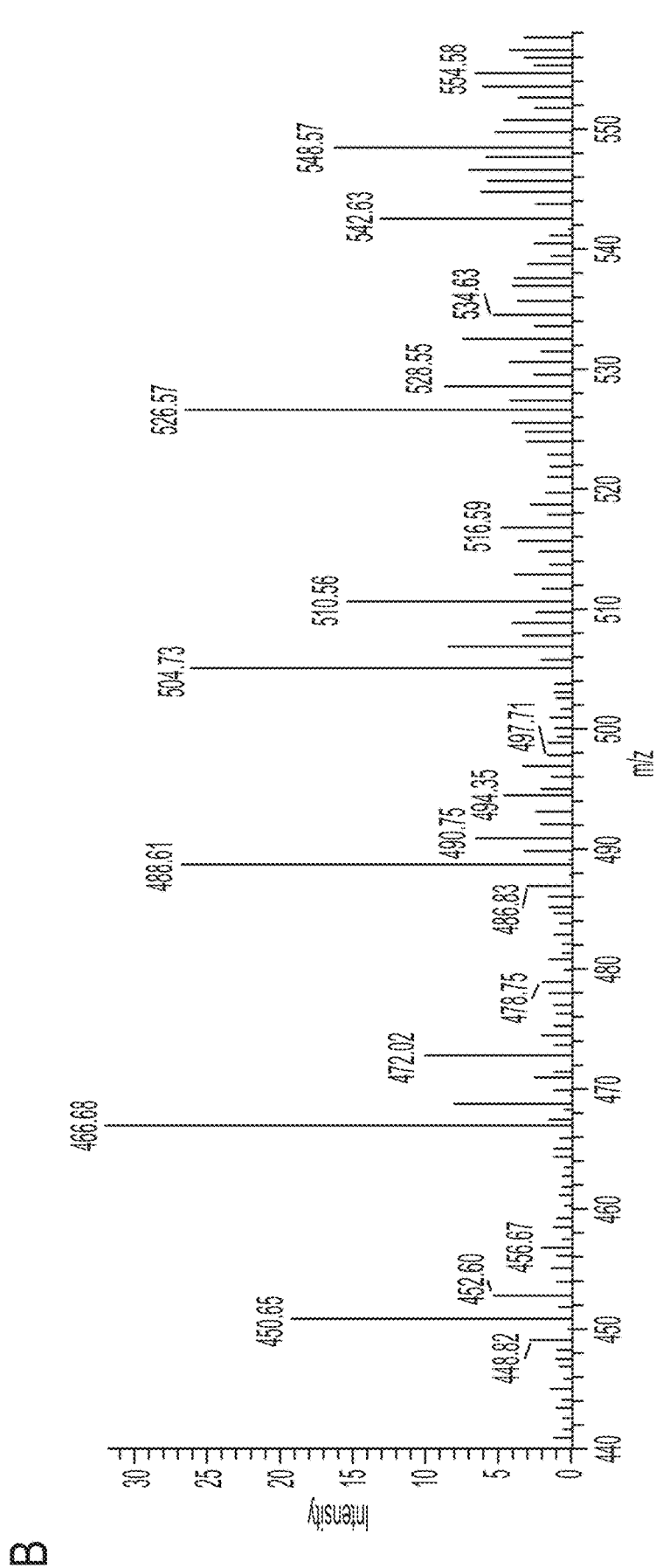
Figure 11:
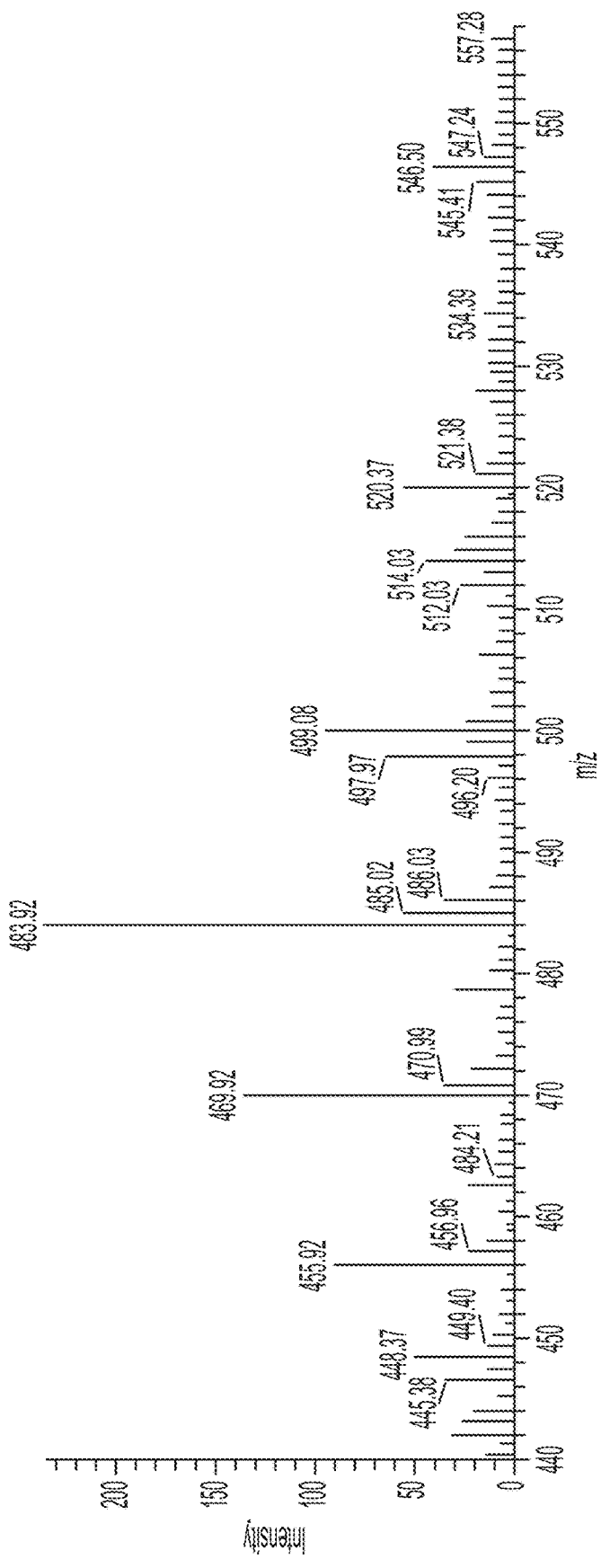

While the monomers of the beta-hydroxy fatty acids were detected with $\frac{1}{20}^{th}$ the intensity during the LC/MS analysis for the incubation of PKA 1 alone (FIG. 9, panel B and FIG. 10, panel B), and with $\frac{1}{5}^{th}$ to ½ the intensity for the incubation of FA-Glu alone (FIG. 10, panel C), none of the homodimers or heterodimers of the beta-hydroxy fatty acids compounds were accurately identified from either reaction sample (FIG. 11, panel B and FIG. 11, panel C). The compounds with m/z ratios of 455.9, 469.9, 483.9 and 499.9 (FIG. 11, panel C) are unknown compounds purified from the fermentation broth of the 27982-H1 culture.

This data suggests that the formation of variable carbon-chain length beta-hydroxy fatty acids from FA-Glu is catalyzed by PKA 1 and is not due to presence of other unknown compounds in the enzyme or substrate preparations. The presence of compound peaks with the expected m/z ratios for the C12-, C13-, and C14-beta-hydroxy fatty acids in electrospray negative mode indicate that the PKA 1 enzyme is capable of cleaving all carbon-chain lengths for FA-Glu.

Figure 12:
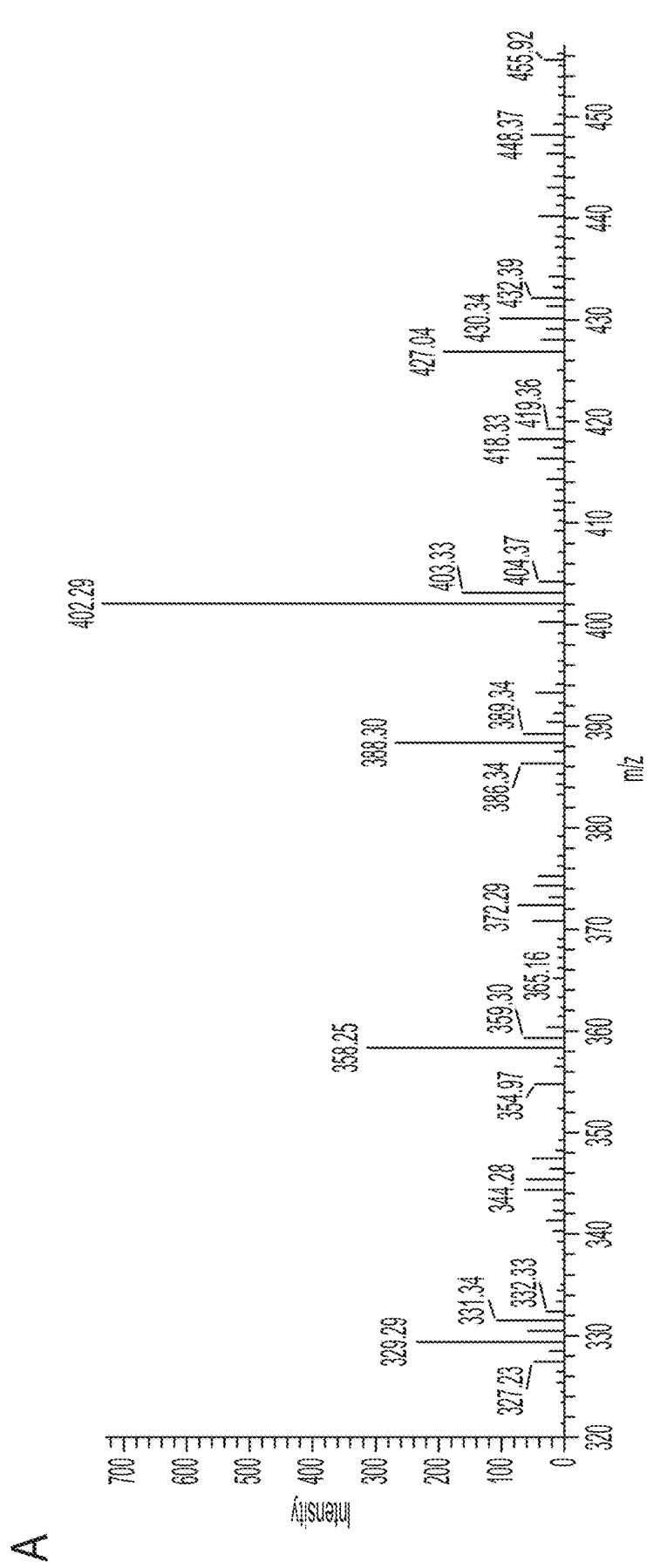
Figure 12:
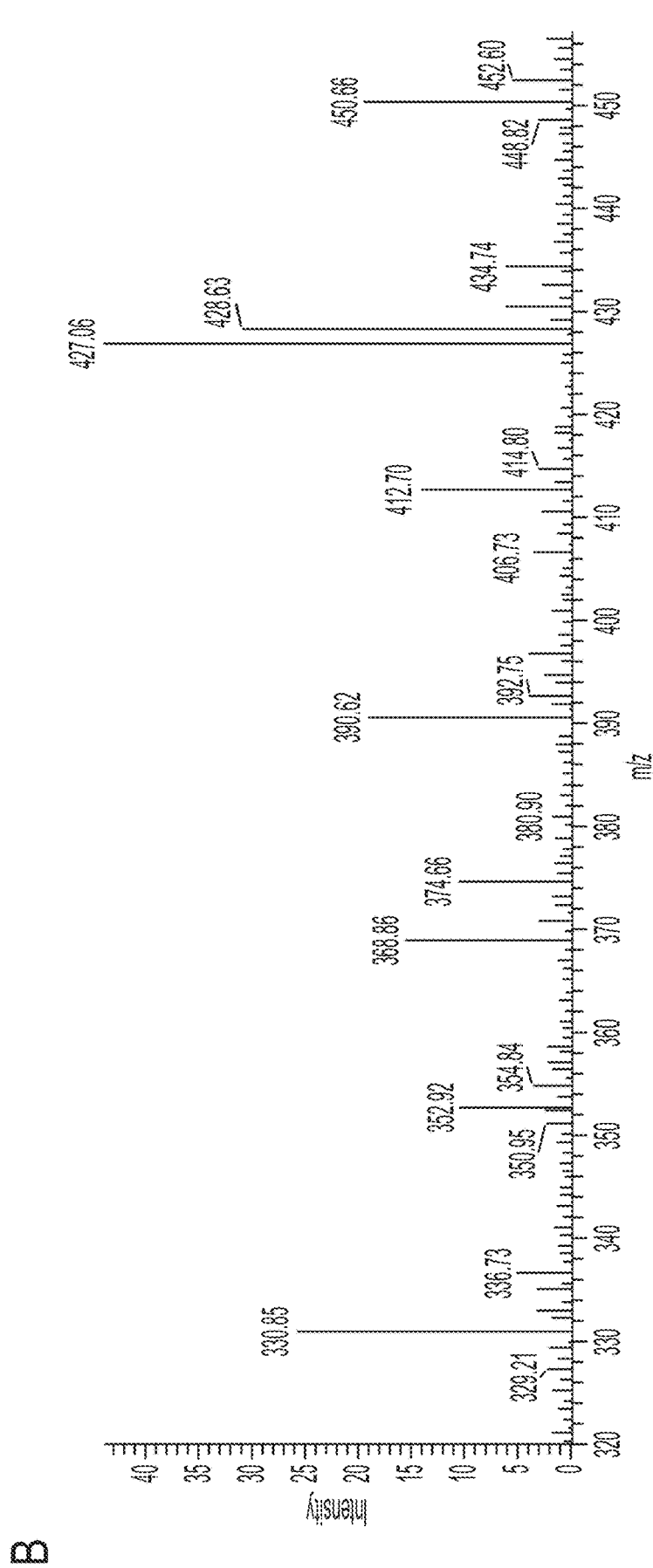
Figure 12:
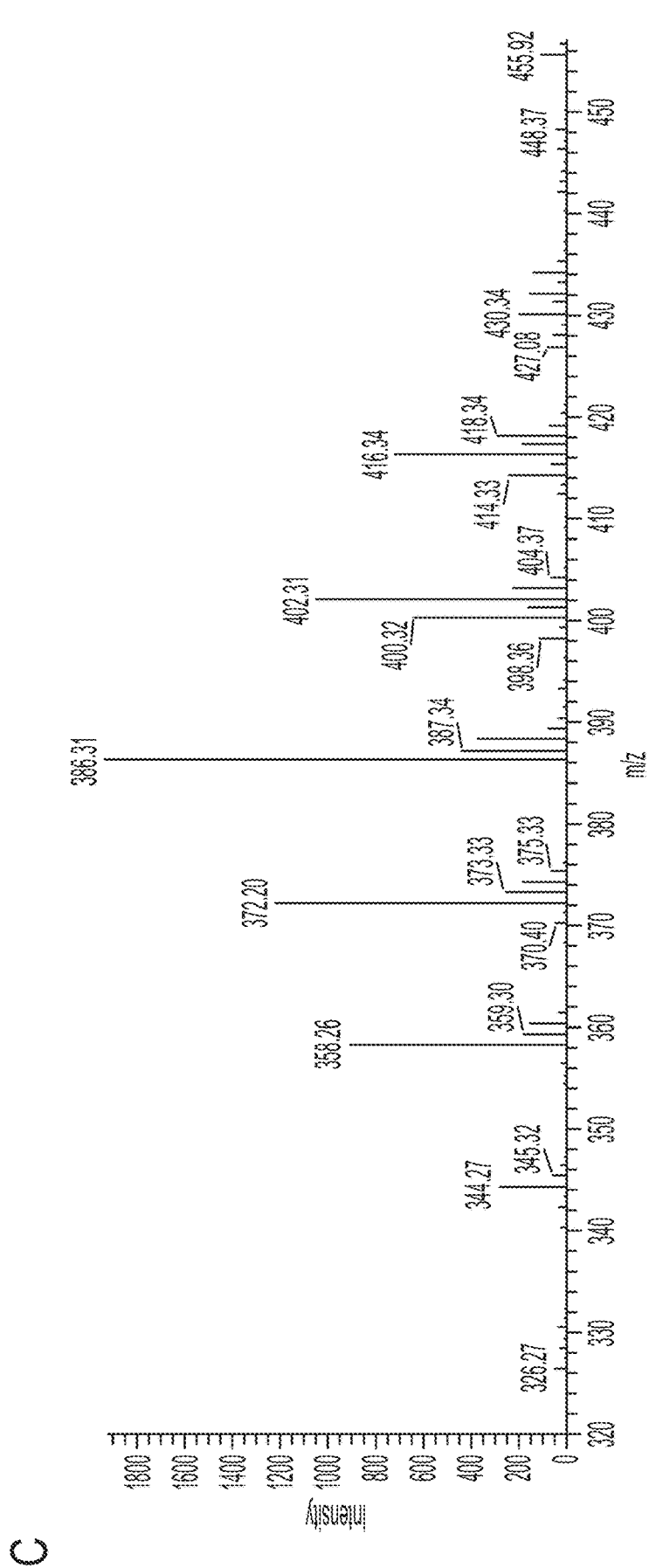
Figure 13:
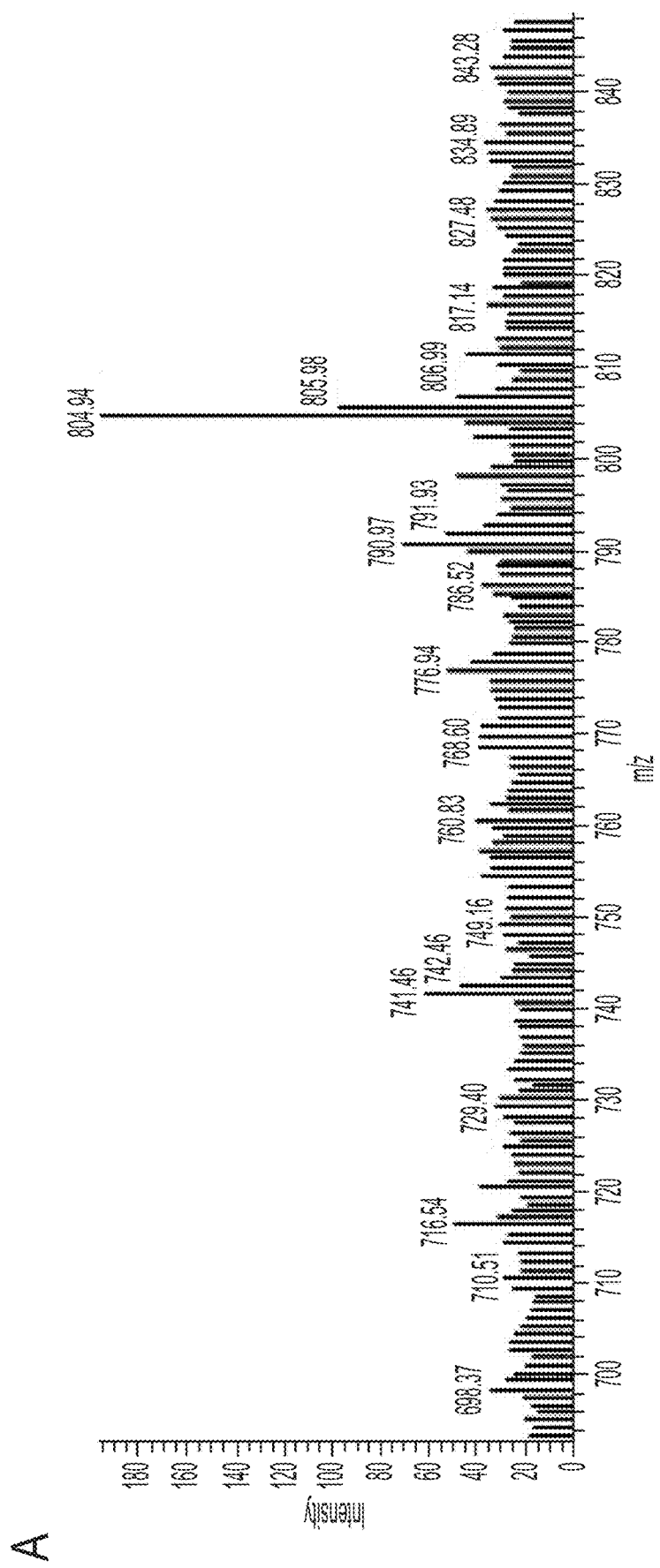
Figure 13:
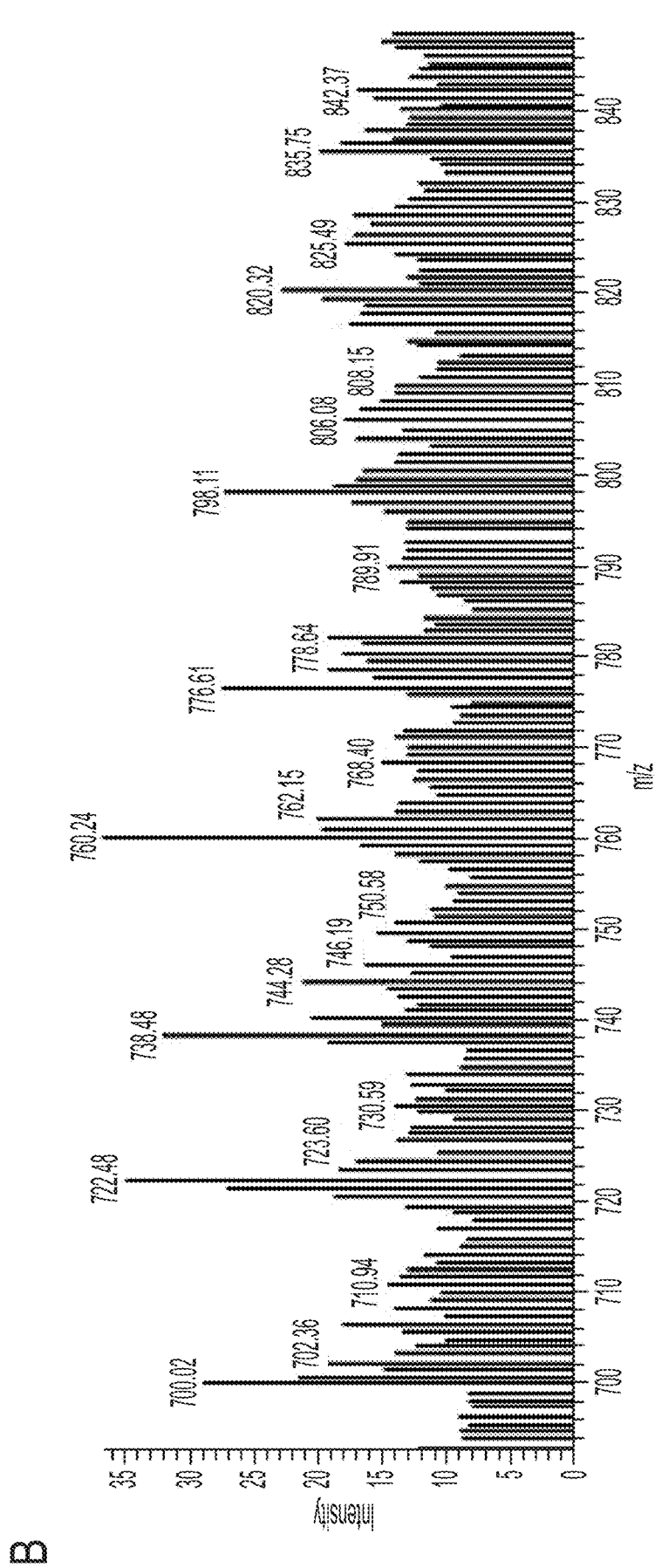
Figure 13:
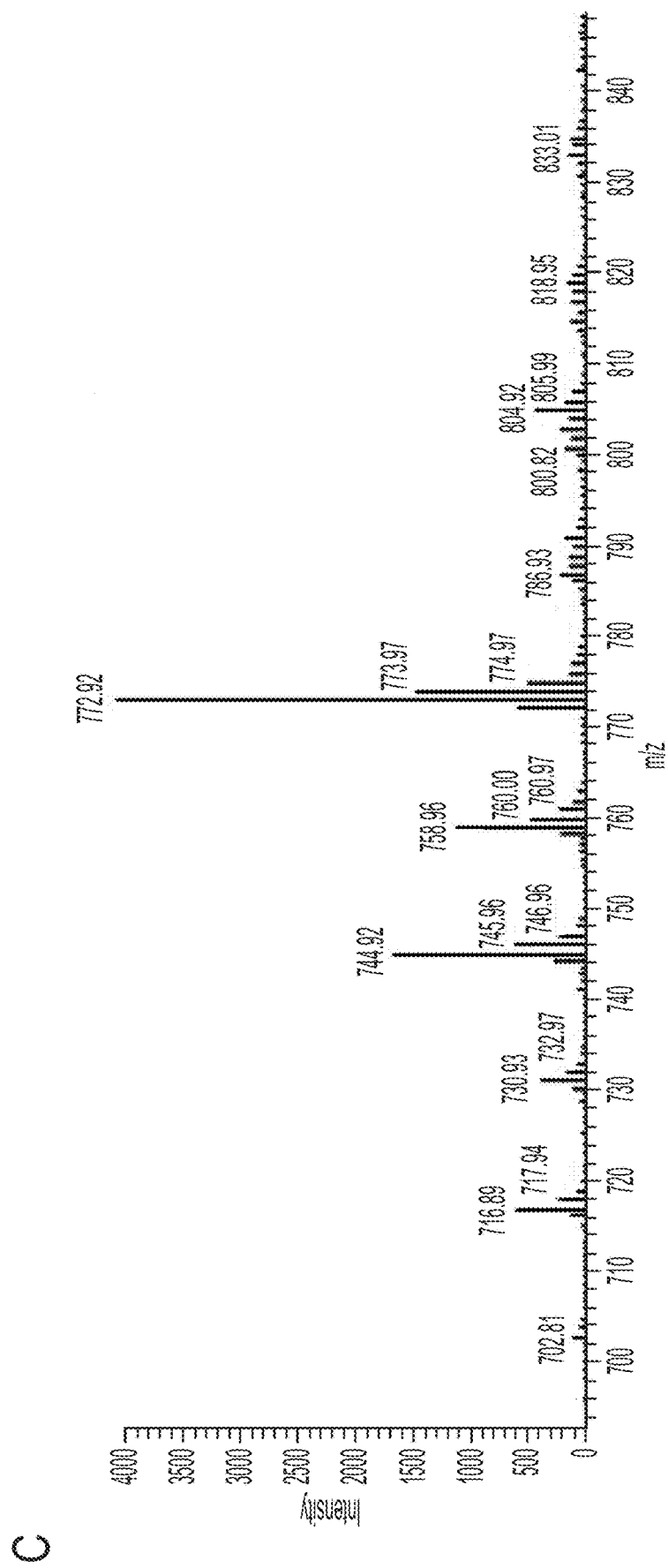

To determine the efficiency of the digestion of FA-Glu by PKA 1, substrate depletion was compared between Reaction 1 (FA-Glu and PKA 1) and Reaction 3 (FA-Glu only). While only the C12-FA-Glu compound (m/z ratio=358.2, FIG. 9, panel A) was detected after incubating FA-Glu with PKA 1, all monomer peaks for the C12-, C13-, C14-FA-Glu substrates were detected after incubation of FA-Glu alone (m/z ratios=344.3, 358.3, 372.3, and 386.3, respectively, FIG. 9, panel C) Homodimers for C11-, C12-, C13-, and C14-FA-Glu substrates were detected with m/z ratios of 716.9, 744.9, and 772.9, respectively (FIG. 9, panel C). Monomers for C15- and C16-FA-Glu-Leu had m/z ratios of 400.3 and 414.3 respectively (FIG. 12, panel C), and the homodimer of C15-FA-Glu-Leu had an m/z ratio of 800.8 (FIG. 13, panel C). Heterodimers were also detected: C11-/C2-FA-Glu (m/z ratio=702.8), C12-/C13-FA-Glu (m/z ratio=730.9), C13-/C14-FA-Glu (m/z ratio=758.9), and C14-/C15-FA-Glu (m/z ratio=786.9) (FIG. 13, panel C).

Results of the substrate depletion analysis clearly indicate that digestion of FA-Glu by PKA 1 was nearly 100% complete after 96 hours of incubation. In addition to the C12-FA-Glu compound (m/z ratio=358.2, FIG. 9, panel A), the C11-, C12-, and C13-FA-Glu substrates were also detected with the m/z ratios=344.3, 372.3, and 386.3 respectively (FIG. 12, panel A). None of the expected homodimers or heterodimers of these FA-Glu substrates were detected when FA-Glu was incubated in PKA 1 (FIG. 13, panel A), showing that the concentration of FA-Glu was too low to cause dimer formation. As for the reaction sample that contained only PKA 1 (Reaction 2), no FA-Glu monomer, homodimer, or heterodimer peaks were detected (FIG. 9, panel B; FIG. 12, panel B: and FIG. 13, panel B).

To determine the relative amount of FA-Glu remaining after incubating FA-Glu with PKA 1, Xcalibur software was used to calculate the peak area for each of the FA-Glu compounds. Relative to the amounts observed when FA-Glu was incubated alone, the C11-, C12-, C13-, C14-, C15, and C16-FA-Glu substrates were 91%, 64%, 97%, 99%, 100%, and 100% digested, respectively, by PKA 1.

To further confirm that FA-Glu had been enzymatically digested by PKA 1, LC/MS was also used to detect glutamate. A standard preparation of glutamate was used to develop and optimize the LC/IS conditions needed to identify free glutamate generated from the digestion of FA-Glu. The standard preparation of glutamate was detected in electrospray positive mode with an expected m/z ratio of 148.1.

FIG. 14 depicts the LC/NIS chromatograms for the detection of glutamate. Panel A depicts results from Reaction 1 (FA-Glu incubated with PKA 1), Panel B depicts results from Reaction 2 (PKAI incubated without substrate), and Panel C depicts results from Reaction 3 (FA-Glu incubated without enzyme).

Glutamate was detected after incubation of FA-Glu with PKA 1 with an m/z ratio of 148.1 (FIG. 14, panel A). Glutamate was not detected in the sample containing only PKA 1 (FIG. 14, panel B) or in the sample containing only FA-Glu (FIG. 14, panel C). Several background peaks were observed. Compound peaks with m/z ratios of 145.1, 146.2, 147.2, and 149.2 were present in all three reaction samples; these peaks may represent compounds present in the 1× reaction buffer, Background peaks with m/z ratios of 148.2 (FIG. 14, panel B) and of 148.4 (FIG. 14, panel C) may be due to the presence of either PKA 1 or FA-Glu, respectively; these peaks are outside the acceptable deviation for glutamate detection, which is +/−0.1 mass units.

In summary, these results confirm that incubation of FA-Glu with PKA 1 results in cleavage of the FA-Glu into free beta-hydroxy fatty acids and glutamate.

The invention claimed is:

1. An engineered microbial cell comprising one or more polypeptides collectively comprising:
   a fatty acid linkage domain comprising a condensation domain of a SrfA subunit of *Bacillus subtilis*'s surfactin synthetase, a single peptide synthetase domain comprising an adenylation domain of a glycine module of *Bacillus brevis*'s gramicidin peptide synthetase, and one or more reductase polypeptides comprising an amino acid sequence that is at least 90% identical to the amino acid sequence of SEQ ID NO: 1,
   which fatty acid linkage domain is covalently linked to the single peptide synthetase domain,
   which fatty acid linkage domain and peptide synthetase domain collectively can produce an acyl amino acid,
   and which one or more reductase polypeptides are collectively capable of reducing the acyl amino acid to an acyl amino alcohol.

2. The engineered microbial cell of claim 1, wherein the one or more polypeptides or one or more components thereof lack a thioesterase domain.

3. The engineered microbial cell of claim 1, wherein the microbial cell is a bacterial cell.

4. The engineered microbial cell of claim 3, wherein the bacterial cell is a *Bacillus* cell.

5. The engineered microbial cell of claim 4, wherein the *Bacillus* cell is a *Bacillus subtilis* cell.

6. The engineered microbial cell of claim 1, wherein the one or more reductase polypeptides are covalently linked to the fatty acid linkage domain and the single peptide synthetase domain.

7. The engineered microbial cell of claim 1, wherein the fatty acid linkage domain is a beta-hydroxy fatty acid linkage domain.

8. The engineered microbial cell of claim 7, wherein the beta-hydroxy fatty acid linkage domain is a beta-hydroxy myristic acid linkage domain.

9. The engineered microbial cell of claim 1, wherein the peptide synthetase domain comprises an adenylation domain, and a thiolation domain, which the adenylation domain and the thiolation domain are covalently linked.

10. The engineered microbial cell of claim 9, wherein the adenylation domain is characterized by an amino acid sequence that is at least 90% identical to the amino acid sequence of the terminal adenylation domain of the gramicidin peptide synthetase from *Bacillus brevis*, wherein the adenylation domain of the gramicidin peptide synthetase from *Bacillus brevis* is set forth in SEQ ID NO: 4.

11. The engineered microbial cell of claim 10, wherein the one or more reductase polypeptides comprise a first reductase polypeptide characterized by an amino acid sequence that is at least 90% identical to the amino acid sequence of the reductase domain of the terminal peptide synthetase domain (module 16) of the gramicidin peptide synthetase from *Bacillus brevis*, wherein the terminal peptide synthetase domain (module 16) of the gramicidin peptide synthetase from *Bacillus brevis* having condensation, adenylation, and reductase domains is set forth in SEQ ID NO: 3.

12. The engineered microbial cell of claim 11, wherein the one or more reductase polypeptides comprise a second reductase polypeptide characterized by an amino acid sequence that is at least 90% identical to the amino acid sequence of the polypeptide produced from *Bacillus brevis* LgrE gene as set forth in SEQ ID NO: 6.

13. The engineered microbial cell of claim 12, wherein the acyl amino alcohol is acyl ethanolamine.

14. The engineered microbial cell of claim 13, wherein the acyl ethanolamine is β-hydroxy myristoyl ethanolamine.

15. The engineered microbial cell of claim 1, wherein the one or more reductase polypeptides comprises (i) a first reductase polypeptide that catalyzes reduction of an acyl amino acid synthesized by the engineered intact microbial cell or one or more components thereof to an acyl amino aldehyde; and (ii) a second reductase polypeptide that catalyzes reduction of the acyl amino aldehyde to an acyl amino alcohol.

* * * * *